US011134865B2

(12) United States Patent
Mizuochi et al.

(10) Patent No.: US 11,134,865 B2
(45) Date of Patent: Oct. 5, 2021

(54) MOTION ANALYSIS SYSTEM, MOTION ANALYSIS APPARATUS, MOTION ANALYSIS PROGRAM, AND MOTION ANALYSIS METHOD

(71) Applicant: SEIKO EPSON CORPORATION, Tokyo (JP)

(72) Inventors: Shunichi Mizuochi, Matsumoto (JP); Akinobu Sato, Matsumoto (JP); Daisuke Sugiya, Chino (JP); Masaaki Sugita, Kawasaki (JP)

(73) Assignee: SEIKO EPSON CORPORATION, Tokyo (JP)

( * ) Notice: Subject to any disclaimer, the term of this patent is extended or adjusted under 35 U.S.C. 154(b) by 456 days.

(21) Appl. No.: 15/888,469

(22) Filed: Feb. 5, 2018

(65) Prior Publication Data
US 2018/0220937 A1 Aug. 9, 2018

(30) Foreign Application Priority Data

Feb. 9, 2017 (JP) .............................. JP2017-022017

(51) Int. Cl.
*A61B 5/00* (2006.01)
*A61B 5/11* (2006.01)
*A61B 5/103* (2006.01)

(52) U.S. Cl.
CPC ............. *A61B 5/112* (2013.01); *A61B 5/1112* (2013.01); *A61B 5/1123* (2013.01); *A61B 5/7278* (2013.01); *A61B 5/1036* (2013.01); *A61B 5/1126* (2013.01); *A61B 2560/0247* (2013.01); *A61B 2562/0219* (2013.01)

(58) Field of Classification Search
CPC ............ A61B 1/00006; A61B 2503/10; A61B 2503/40; A61B 2562/0219; A61B 5/11; A61B 5/1118; A61B 5/112; A61B 5/1116; A61B 5/1126; A61B 5/1112; A61B 5/1123; A61B 5/7278; A61B 2560/0247; A61B 5/1036
USPC ................ 600/300, 301, 587, 595; 702/188; 434/247
See application file for complete search history.

(56) References Cited

U.S. PATENT DOCUMENTS

| 7,805,149 | B2 * | 9/2010 | Werner | .............. | A63B 24/0062 342/357.57 |
| 8,280,681 | B2 * | 10/2012 | Vock | ..................... | A61B 5/1118 702/173 |
| 8,686,862 | B2 * | 4/2014 | Dunham | .............. | A43B 3/0015 340/286.01 |
| 9,504,414 | B2 * | 11/2016 | Coza | ..................... | A61B 5/1112 |
| 9,642,415 | B2 * | 5/2017 | Pease | .................. | G01C 22/006 |

(Continued)

FOREIGN PATENT DOCUMENTS

| JP | 2007-125368 A | 5/2007 |
| JP | 2010-264246 A | 11/2010 |
| JP | 2016-034482 A | 3/2016 |

*Primary Examiner* — May A Abouelela
(74) *Attorney, Agent, or Firm* — Oliff PLC

(57) ABSTRACT

A motion analysis apparatus includes a motion analysis unit that analyzes motion information in walking or running of a user by using a detection result in an inertial sensor, and an output unit that outputs information regarding a propulsion force generated in the body of the user within one cycle of a motion related to the walking or the running for each action of the user within the one cycle on the basis of the motion information.

16 Claims, 24 Drawing Sheets

(56) References Cited

U.S. PATENT DOCUMENTS

| | | | |
|---|---|---|---|
| 10,363,453 B2* | 7/2019 | Fitzgerald | A61B 5/486 |
| 2003/0139692 A1* | 7/2003 | Barrey | A61B 5/061 |
| | | | 600/595 |
| 2007/0006489 A1* | 1/2007 | Case, Jr. | A43B 5/06 |
| | | | 36/132 |
| 2007/0073514 A1 | 3/2007 | Nogimori et al. | |
| 2007/0247306 A1* | 10/2007 | Case, Jr. | A43B 3/0005 |
| | | | 340/539.11 |
| 2008/0214360 A1* | 9/2008 | Stirling | A61B 5/1118 |
| | | | 482/9 |
| 2008/0285805 A1* | 11/2008 | Luinge | A61B 5/1122 |
| | | | 382/107 |
| 2008/0287832 A1* | 11/2008 | Collins | A43B 13/00 |
| | | | 600/587 |
| 2009/0047645 A1* | 2/2009 | Dibenedetto | A61B 5/11 |
| | | | 434/258 |
| 2009/0048044 A1* | 2/2009 | Oleson | A43B 5/06 |
| | | | 473/570 |
| 2009/0240171 A1* | 9/2009 | Morris Bamberg | A43B 3/0005 |
| | | | 600/595 |
| 2010/0063779 A1* | 3/2010 | Schrock | A43B 17/02 |
| | | | 702/188 |
| 2010/0184564 A1* | 7/2010 | Molyneux | A63B 71/0605 |
| | | | 482/1 |
| 2010/0292050 A1 | 11/2010 | DiBenedetto et al. | |
| 2011/0054359 A1* | 3/2011 | Sazonov | A61B 5/4866 |
| | | | 600/595 |
| 2012/0092169 A1* | 4/2012 | Kaiser | A61B 5/6807 |
| | | | 340/573.1 |
| 2012/0253234 A1* | 10/2012 | Yang | A61B 5/1038 |
| | | | 600/595 |
| 2014/0148931 A1* | 5/2014 | Watanabe | A63B 71/06 |
| | | | 700/92 |
| 2014/0228712 A1* | 8/2014 | Elliott | A63B 71/06 |
| | | | 600/587 |
| 2014/0288680 A1* | 9/2014 | Hoffman | A43C 19/00 |
| | | | 700/91 |
| 2014/0336003 A1* | 11/2014 | Franz | A63B 71/0622 |
| | | | 482/8 |
| 2014/0343460 A1* | 11/2014 | Evans, III | A61B 5/6829 |
| | | | 600/595 |
| 2015/0142329 A1* | 5/2015 | Ostman | A61B 5/222 |
| | | | 702/19 |
| 2015/0196821 A1* | 7/2015 | Kang | A63G 19/20 |
| | | | 434/247 |
| 2016/0029954 A1* | 2/2016 | Sato | A61B 5/6804 |
| | | | 702/141 |
| 2016/0030804 A1 | 2/2016 | Mizuochi et al. | |
| 2016/0030808 A1* | 2/2016 | Uchida | G09B 19/0038 |
| | | | 482/8 |
| 2016/0030823 A1* | 2/2016 | Sato | G06K 9/00342 |
| | | | 434/255 |
| 2016/0035229 A1* | 2/2016 | Uchida | G09B 19/0038 |
| | | | 434/247 |
| 2016/0058326 A1* | 3/2016 | Winfree | A61B 5/7278 |
| | | | 600/592 |
| 2016/0081614 A1* | 3/2016 | Aibara | A61B 5/1112 |
| | | | 600/595 |
| 2016/0114213 A1* | 4/2016 | Lee | A61B 5/1118 |
| | | | 434/255 |
| 2017/0042467 A1* | 2/2017 | Herr | A61B 5/486 |
| 2017/0211997 A1* | 7/2017 | Kulach | A63C 11/228 |
| 2018/0221239 A1* | 8/2018 | Kuchenbecker | A61B 5/4836 |
| 2018/0280761 A1* | 10/2018 | Izuru | A63B 24/0062 |
| 2018/0373926 A1 | 12/2018 | Mizuochi et al. | |

\* cited by examiner

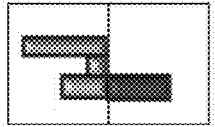
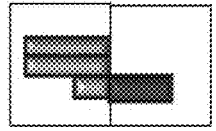
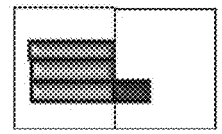

- YOU RAN IN WAY OF SLOW TURNOVER OF LEGS
- YOUR RUN TYPE MAY CAUSE LEGS TO BE TIRED IN SECOND HALF OF MARATHON
- LET'S PERFORM EXERCISE NOT CAUSING SLOW TURNOVER OF LEGS
- EXERCISE SUCH AS SCISSORS OR MARCHING IS BEST

- IN YOUR RUN TYPE, BRAKE IS CONSIDERABLE, AND PROPULSION FORCE CANNOT BE OBTAINED DUE TO BRAKE. THERE IS PROBABILITY OF OVERSTRIDE.
- NOTE INJURIES OF WAIST, KNEES, THIGHS, AND THE LIKE
- PERFORM EXERCISE OF BEING AWARE OF DIRECTLY-BELOW LANDING IN ORDER TO IMPROVE OVERSTRIDE
- EXERCISE SUCH AS BOUNDING IS BEST

- IN YOUR RUN TYPE, PROPULSION FORCE DUE TO KICKING OF LEGS IS CONSIDERABLE
- PERFORM EXERCISE OF USING ANKLES IN FIXED STATE ASSUMING THAT LEGS ARE RODS
- YOU WILL BE ABLE TO BE CONSCIOUS OF PROPULSION FORCE BY CHECKING PROPULSION FORCE DUE TO KICKING OF LEGS IN REAL TIME DURING RUNNING

FIG. 27

- YOU HAVE PROPULSION FORCE OF DEVELOPMENT AGENCY LEVEL. AN EFFICIENT PROPULSION FORCE IS OBTAINED
- TRY TO FURTHER IMPROVE PROPULSION FORCE DUE TO BRAKE
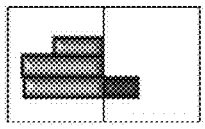
- YOU HAVE PROPULSION FORCE OF WORLD LEVEL. QUITE EFFICIENT PROPULSION FORCE IS OBTAINED.
- PERFORM EXERCISE SUCH THAT THE SAME POWER RATIO IS OBTAINED EVEN IF VELOCITY IS INCREASED
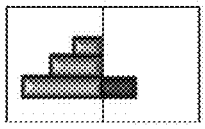
FIG. 28

MOTION ANALYSIS SYSTEM, MOTION ANALYSIS APPARATUS, MOTION ANALYSIS PROGRAM, AND MOTION ANALYSIS METHOD

BACKGROUND

1. Technical Field

The present invention relates to a motion analysis system, a motion analysis apparatus, a motion analysis program, and a motion analysis method.

2. Related Art

For example, JP-A-2010-264246 discloses a portable fitness monitoring device which provides various pieces of biological information or motion information to a user during training. The portable fitness monitoring device measures various performance parameters such as a heart rate, a distance, a speed, the number of steps, and calorie consumption of a user during motion, mounted with various sensors such as a heart rate meter, an accelerometer, and a GPS receiver, and provides the information to the user as information at the present time.

However, the device only detects biological information or motion information of the user during motion and merely provides the information or an analysis result thereof to the user, and does not provide information regarding an attitude of the user during motion or a use method for the body thereof.

SUMMARY

An advantage of some aspects of the invention is to provide a motion analysis system, a motion analysis apparatus, a motion analysis program, and a motion analysis method, capable of providing information in which an attitude of a walking or running user or a use method for the body of the user is reflected.

The invention can be implemented as the following forms or application examples.

Application Example 1

A motion analysis apparatus according to this application example includes a motion analysis unit that analyzes motion information in walking or running of a user by using a detection result in an inertial sensor; and an output unit that outputs information regarding a propulsion force generated in the body of the user within one cycle of a motion related to the walking or the running for each action of the user within the one cycle on the basis of the motion information.

The motion analysis unit analyzes motion information (for example, a temporal change in a propulsion force generated in the body of a user) in walking or running of the user by using the inertial sensor (for example, an acceleration sensor or an angular velocity sensor). The output unit outputs information regarding a propulsion force generated in the body of the user within one cycle (that is, a section corresponding to one step) of a motion related to the walking or the running for each action (for example, for each of an action using at least one of an inertial force and the gravity, an action using rotation of at least a part of the body, and an action using muscle strength of the body) of the user within the one cycle on the basis of the motion information. Since a walking or running form of the user is reflected in the information regarding each action in detail, the user (a walking or running user or a manager thereof) analyzes the magnitude relationship among propulsion forces of the respective actions or a temporal change in the propulsion force of each action so as to easily find out a habit of the walking or running form or to derive a measure for improvement of the form.

Application Example 2

In the motion analysis apparatus according to the application example, the one cycle may be a section from landing to the next landing in a motion related to the walking or the running.

As mentioned above, since one cycle is set to a section from landing to landing, a motion related to walking or running can be output to be easily understood by a user.

Application Example 3

In the motion analysis apparatus according to the application example, the action of the user may include at least one of (i) an action using at least one of an inertial force and the gravity, (ii) an action using rotation of at least a part of the body, and (iii) an action using muscle strength of the body.

According to the configuration, the user can recognize a propulsion force related to at least one of the actions (i), (ii) and (iii) separately from other propulsion forces. The "action using at least one of an inertial force and the gravity" is, for example, a brake action in landing, the "action using rotation of at least a part of the body" is, for example, an action of returning the leg, and the "action using muscle strength of the body" is, for example, an action of stretching the leg, for example, stretching the ankle.

Application Example 4

In the motion analysis apparatus according to the application example, the information output from the output unit may include information regarding the propulsion force caused by the right foot of the user, and information regarding a propulsion force caused by the left foot of the user.

According to the configuration, the user can separately recognize a propulsion force related to the left foot and a propulsion force related to the right foot.

Application Example 5

In the motion analysis apparatus according to the application example, the output unit may output information regarding a brake within the one cycle along with the information regarding the propulsion force.

According to the configuration, the user can recognize a propulsion force through comparison with the brake (corresponding to a negative propulsion force). For example, the user can analyze the magnitude relationship between a propulsion force and the brake, or a temporal change in the magnitude relationship.

Application Example 6

In the motion analysis apparatus according to the application example, the output unit may output the information regarding the propulsion force at each predetermined distance within a movement path of the user.

According to the configuration, the user can recognize a propulsion force at each distance, and can thus compare, for example, propulsion forces between a first half and a second half of a movement path, or analyze a relationship between a movement distance and a propulsion force.

Application Example 7

In the motion analysis apparatus according to the application example, the output unit may output the information regarding the propulsion force for each predetermined time within a movement period of the user.

According to the configuration, the user can recognize a propulsion force for each time, and can thus compare, for example, propulsion forces between a first half and a second half of a movement period, or analyze a relationship between a movement time and a propulsion force.

Application Example 8

A motion analysis method according to this application example includes analyzing motion information in walking or running of a user by using a detection result in an inertial sensor; and outputting information regarding a propulsion force generated in the body of the user within one cycle of a motion related to the walking or the running for each action of the user within the one cycle on the basis of the motion information.

In the analysis step, motion information (for example, a temporal change in a propulsion force generated in the body of a user) in walking or running of the user is analyzed by using the inertial sensor (for example, an acceleration sensor or an angular velocity sensor). In the output step, information regarding a propulsion force generated in the body of the user within one cycle (that is, a section corresponding to one step) of a motion related to the walking or the running is output for each action (for example, for each of an action using at least one of an inertial force and the gravity, an action using rotation of at least a part of the body, and an action using muscle strength of the body) of the user within the one cycle on the basis of the motion information (for example, a temporal change in a propulsion force generated in the user's body). Since a walking or running form of the user is reflected in the information regarding each action in detail, the user (a walking or running user or a manager thereof) analyzes the magnitude relationship among propulsion forces of the respective actions or a temporal change in the propulsion force of each action so as to easily find out a habit of the walking or running form or to derive a measure for improvement of the form.

Application Example 9

A motion analysis system according to this application example includes the motion analysis apparatus according to any one of the application examples; and the inertial sensor.

Application Example 10

A motion analysis program according to this application example causes a computer to execute analyzing motion information in walking or running of a user by using a detection result in an inertial sensor; and outputting information regarding a propulsion force generated in the body of the user within one cycle of a motion related to the walking or the running for each action of the user within the one cycle on the basis of the motion information.

In the analysis step, motion information (for example, a temporal change in a propulsion force generated in the body of a user) in walking or running of the user is analyzed by using the inertial sensor (for example, an acceleration sensor or an angular velocity sensor). In the output step, information regarding a propulsion force generated in the body of the user within one cycle (that is, a section corresponding to one step) of a motion related to the walking or the running is output for each action (for example, for each of an action using at least one of an inertial force and the gravity, an action using rotation of at least a part of the body, and an action using muscle strength of the body) of the user within the one cycle on the basis of the motion information (for example, a temporal change in a propulsion force generated in the user's body). Since a walking or running form of the user is reflected in the information regarding each action in detail, the user (a walking or running user or a manager thereof) analyzes the magnitude relationship among propulsion forces of the respective actions or a temporal change in the propulsion force of each action so as to easily find out a habit of the walking or running form or to derive a measure for improvement of the form.

Application Example 11

A motion analysis apparatus according to this application example analyzes motion information in walking or running of a user by using a detection result in an inertial sensor, and outputs information regarding a propulsion force generated in the body of the user within one cycle of a motion related to the walking or the running for each action of the user within the one cycle on the basis of the motion information.

The motion analysis apparatus analyzes motion information (for example, a temporal change in a propulsion force generated in the body of a user) in walking or running of the user by using the inertial sensor (for example, an acceleration sensor or an angular velocity sensor), and outputs information regarding a propulsion force generated in the body of the user within one cycle (that is, a section corresponding to one step) of a motion related to the walking or the running for each action (for example, for each of an action using at least one of an inertial force and the gravity, an action using rotation of at least a part of the body, and an action using muscle strength of the body) of the user within the one cycle on the basis of the motion information (for example, a temporal change in a propulsion force generated in the user's body). Since a walking or running form of the user is reflected in the information regarding each action in detail, the user (a walking or running user or a manager thereof) analyzes the magnitude relationship among propulsion forces of the respective actions or a temporal change in the propulsion force of each action so as to easily find out a habit of the walking or running form or to derive a measure for improvement of the form.

BRIEF DESCRIPTION OF THE DRAWINGS

The invention will be described with reference to the accompanying drawings, wherein like numbers reference like elements.

FIG. 27 is still another example (an example of an evaluation result) of a screen displayed on the display of the information analysis apparatus during the user's running.

FIG. 28 is a diagram subsequent to FIG. 27.

DESCRIPTION OF EXEMPLARY EMBODIMENTS

Hereinafter, preferred embodiments of the invention will be described in detail with reference to the drawings. The drawings are used for convenience of description. The embodiments described below are not intended to improperly limit the configuration of the invention disclosed in the appended claims. It cannot be said that all constituent elements described below are essential constituent elements of the invention.

1. Motion Analysis System 1-1. Configuration of System

Figure 1:
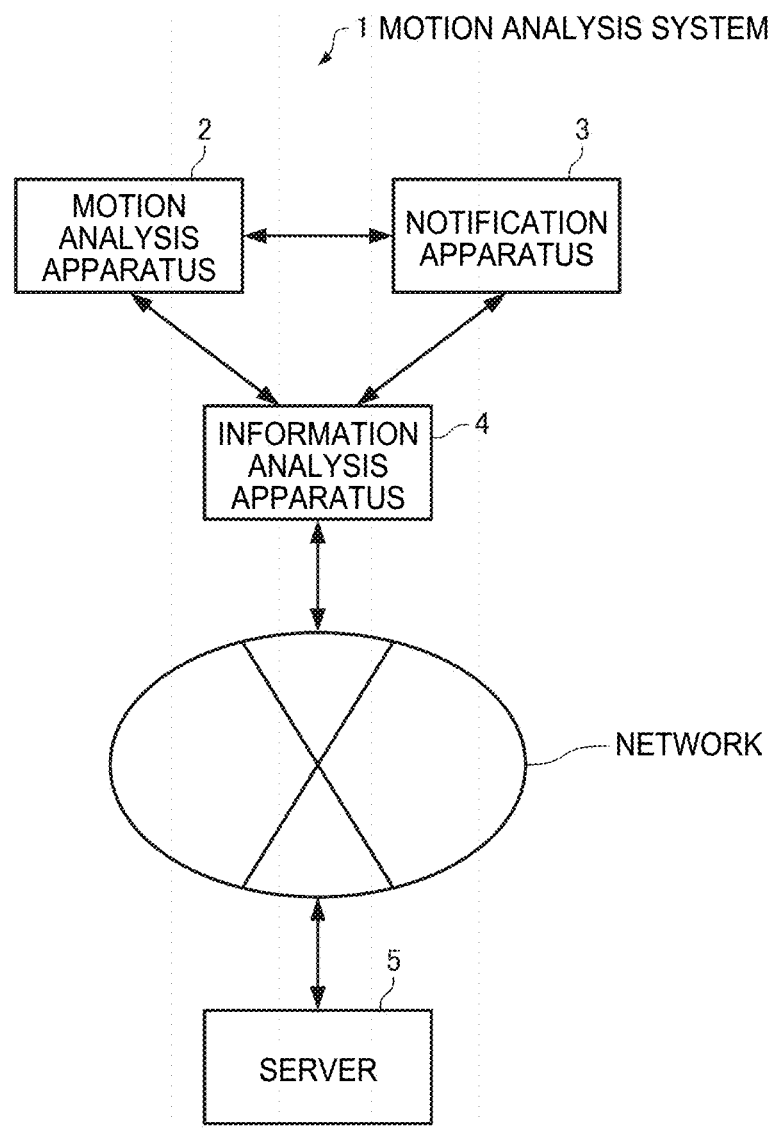
FIG. 1 is a diagram illustrating a configuration example of a motion analysis system of the present embodiment.
Figure 2:
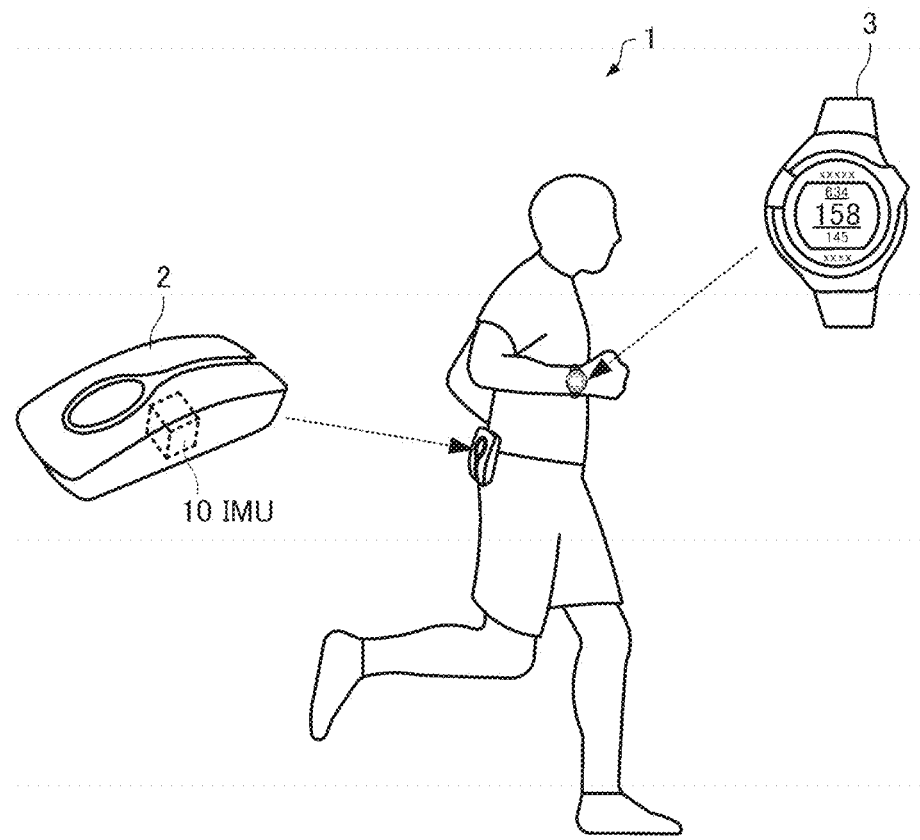
FIG. 2 is a diagram illustrating an overview of the motion analysis system of the present embodiment.

Hereinafter, as an example, a description will be made of a motion analysis system 1 of analyzing motion in a user's running (including walking), but the motion analysis system of the present embodiment is similarly applicable to a motion analysis system analyzing motions other than running. FIG. 1 is a diagram illustrating a configuration example of the motion analysis system 1 of the present embodiment. As illustrated in FIG. 1, the motion analysis system 1 of the present embodiment is configured to include a motion analysis apparatus 2, a notification apparatus 3, and an information analysis apparatus 4. The motion analysis apparatus 2 is an apparatus analyzing motion of a user during running, and the notification apparatus 3 is an apparatus notifying the user of a motion state during running or information regarding a running result. The information analysis apparatus 4 is an apparatus which analyzes and presents a running result after the user's running is finished. In the present embodiment, as illustrated in FIG. 2, the motion analysis apparatus 2 has an inertial measurement unit (IMU) 10 built thereinto, and is mounted on a body part (for example, a right waist, a left waist, or a central part of the waist) of the user such that one detection axis (hereinafter, referred to as a z axis) of the inertial measurement unit (IMU) 10 substantially matches the gravitational acceleration direction (vertically downward direction) in a state in which the user stands still. The notification apparatus 3 is a wrist type (wristwatch type) portable information apparatus and is mounted on the user's wrist or the like. However, the notification apparatus 3 may be a portable information apparatus such as a head mounted display (HMD) or a smart phone.

The user operates the notification apparatus 3 at the time of starting running, so as to instruct the motion analysis apparatus 2 to start measurement (an inertial navigation calculation process or a motion analysis process which will be described later), and operates the notification apparatus 3 at the time of finishing the running, so as to instruct the motion analysis apparatus 2 to start or finish a running analysis process (which will be described later). The notification apparatus 3 transmits a command for instructing measurement to be started or finished to the motion analysis apparatus 2 in response to the user's operation.

If a command for starting measurement is received, the motion analysis apparatus 2 causes the inertial measurement unit (IMU) 10 to start measurement, computes values of various motion indexes which are indexes related to the user's running performance (an example of motion performance) by using a measurement result, and generates motion analysis information 350 including the values of various motion indexes as information regarding an analysis result of the user's running motion. The motion analysis apparatus 2 generates information (output information during running) which is output during the user's running by using the generated motion analysis information 350, and transmits the information to the notification apparatus 3. The notification apparatus 3 receives the output information during running from the motion analysis apparatus 2, compares each value of the various motion indexes included in the output information during running with each target value which is set in advance, and notifies the user of goodness and badness of each motion index by using sounds or vibration. Consequently, the user can run while recognizing goodness and badness of each motion index.

If a command for finishing the measurement is received, the motion analysis apparatus 2 causes the inertial measurement unit (IMU) 10 to finish the measurement, generates information regarding a running result of the user (running result information: a running distance and a running speed), and transmits the running result information to the notification apparatus 3. The notification apparatus 3 receives the running result information from the motion analysis apparatus 2, and notifies the user of the running result information as text or images. Consequently, the user can immediately recognize the running result information after the running is finished.

Data communication between the motion analysis apparatus 2 and the notification apparatus 3 may be wireless communication or wired communication.

As illustrated in FIG. 1, in the present embodiment, the motion analysis system 1 is configured to include a server 5 connected to a network such as the Internet or a local area network (LAN). The information analysis apparatus 4 is, for example, an information apparatus such as a personal computer or a smart phone, and can perform data communication with the server 5 via the network. The information analysis apparatus 4 acquires the motion analysis information 350 in the past running of the user from the motion analysis apparatus 2, and transmits the motion analysis information 350 to the server 5 via the network. However, an apparatus which is different from the information analysis apparatus 4 may acquire the motion analysis information 350 from the motion analysis apparatus 2, and transmit the motion analysis information to the server 5, and the motion analysis apparatus 2 may directly transmit the motion analysis information to the server 5. The server 5 receives the motion analysis information 350, and preserves the motion analysis information in a database built in a storage unit (not illustrated). In the present embodiment, a plurality of users wear the same or different motion analysis apparatuses 2, and the motion analysis information 350 of each user is preserved in the database of the server 5.

The information analysis apparatus 4 acquires the motion analysis information 350 of a plurality of users from the database of the server 5 via the network, generates analysis information in which running performances of the plurality of users can be compared with each other, and displays the analysis information on a display (not illustrated in FIG. 1). The running performance of a specific user can be compared with that of another user for relative evaluation, or a target value of each motion index can be appropriately set, on the basis of the analysis information displayed on the display of the information analysis apparatus 4. In a case where a user sets a target value of each motion index, the information analysis apparatus 4 transmits target value set information of each motion index to the notification apparatus 3. The notification apparatus 3 receives the target value set information of each motion index from the information analysis apparatus 4, and updates each target value used to be compared with the above-described value of each motion index.

The motion analysis system 1 may have a configuration in which the motion analysis apparatus 2, the notification apparatus 3, and the information analysis apparatus 4 are provided separately from each other; the motion analysis apparatus 2 and the notification apparatus 3 are integrally provided, and the information analysis apparatus 4 is separately provided; the notification apparatus 3 and the information analysis apparatus 4 are integrally provided, and the motion analysis apparatus 2 is separately provided; the motion analysis apparatus 2 and the information analysis apparatus 4 are integrally provided, and the notification apparatus 3 is separately provided; or the motion analysis apparatus 2, the notification apparatus 3, and the information analysis apparatus 4 are integrally provided. The motion analysis apparatus 2, the notification apparatus 3, and the information analysis apparatus 4 may be provided according to any combination.

1-2. Coordinate System

Coordinate systems necessary in the following description are defined.

Figure 3:
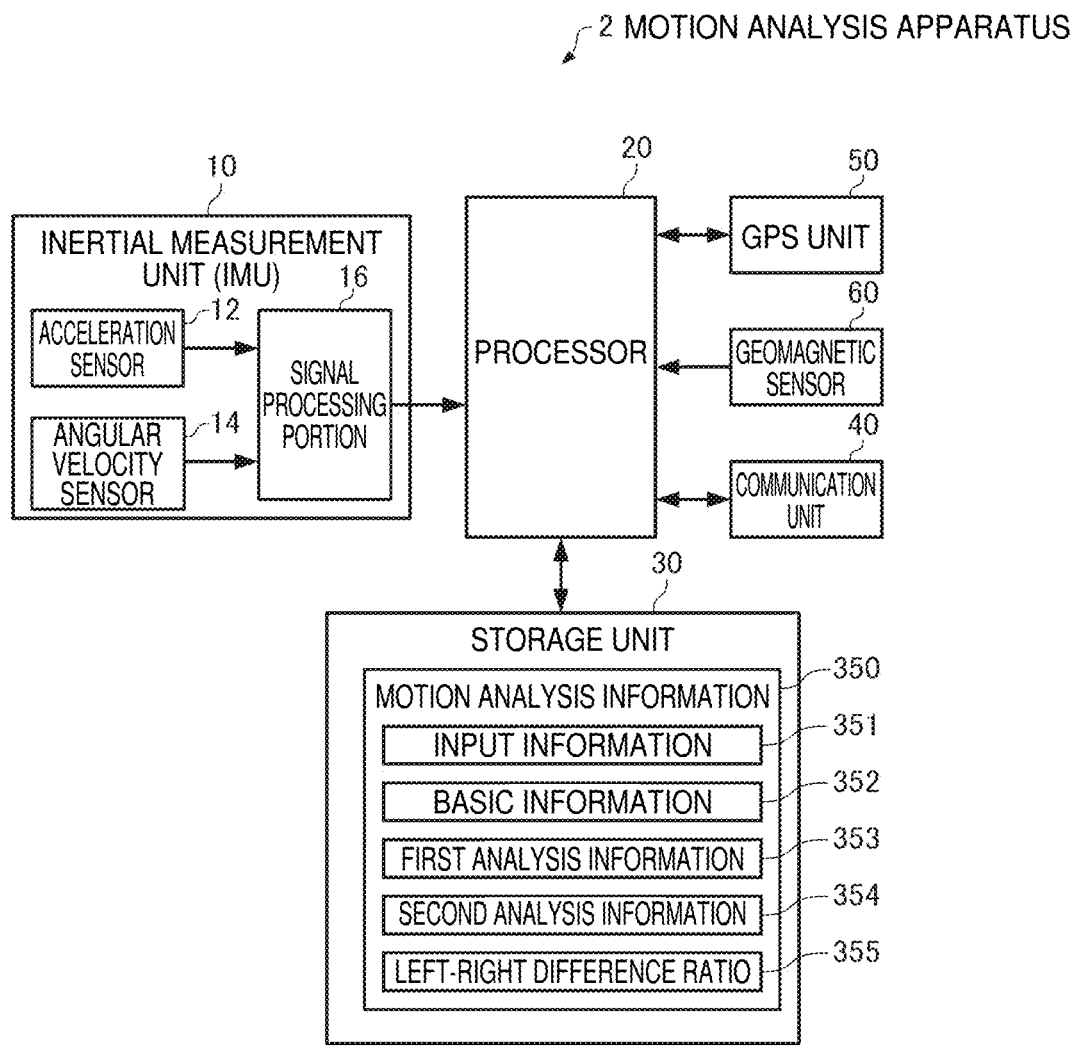
FIG. 3 is a functional block diagram illustrating a configuration example of a motion analysis apparatus.

Earth centered earth fixed frame (e frame): right handed three-dimensional orthogonal coordinate system in which the center of the earth is set as an origin, and a z axis is taken so as to be parallel to the axis of the earth Navigation frame (n frame): three-dimensional orthogonal coordinate system in which a moving object (user) is set as an origin, and an x axis is set to the north, a y axis is set to the east, and a z axis is set to the gravitational direction Body frame (b frame): three-dimensional orthogonal coordinate system using a sensor (the inertial measurement unit (IMU) 10) as a reference Moving frame (m frame): right handed three-dimensional orthogonal coordinate system in which a moving object (user) is set as an origin, and an advancing direction of the moving object (user) is set as an x axis 1-3. Motion Analysis Apparatus 1-3-1. Configuration of Motion Analysis Apparatus FIG. 3 is a functional block diagram illustrating a configuration example of the motion analysis apparatus 2. As illustrated in FIG. 3, the motion analysis apparatus 2 is configured to include the inertial measurement unit (IMU) 10, a processor 20, a storage unit 30, a communication unit 40, a global positioning system (GPS) unit 50, and a geomagnetic sensor 60. However, the motion analysis apparatus 2 of the present embodiment may have a configuration in which some of the constituent elements are deleted or changed, or other constituent elements may be added thereto.

The inertial measurement unit 10 (an example of an inertial sensor) includes an acceleration sensor 12, an angular velocity sensor 14, and a signal processing portion 16.

The acceleration sensor 12 detects respective accelerations in the three-axis directions which intersect each other (ideally, orthogonal to each other), and outputs a digital signal (acceleration data) corresponding to magnitudes and directions of the detected three-axis accelerations.

The angular velocity sensor 14 detects respective angular velocities in the three-axis directions which intersect each other (ideally, orthogonal to each other), and outputs a digital signal (angular velocity data) corresponding to magnitudes and directions of the detected three-axis angular velocities.

The signal processing portion 16 receives the acceleration data and the angular velocity data from the acceleration sensor 12 and the angular velocity sensor 14, respectively, adds time information thereto, stores the data and the time information in a storage unit (not illustrated), generates sensing data in which the stored acceleration data, angular velocity data and time information conform to a predetermined format, and outputs the sensing data to the processor 20.

The acceleration sensor 12 and the angular velocity sensor 14 are ideally installed so as to match three axes of a sensor coordinate system (b frame) with the inertial measurement unit 10 as a reference, but, in practice, an error occurs in an installation angle. Therefore, the signal processing portion 16 performs a process of converting acceleration data and the angular velocity data into data of the sensor coordinate system (b frame) by using a correction parameter which is calculated in advance according to the installation angle error. Instead of the signal processing portion 16, the processor 20 to be described later may perform the process.

The signal processing portion 16 may perform a temperature correction process on the acceleration sensor 12 and the angular velocity sensor 14. Instead of the signal processing portion 16, the processor 20 to be described later may perform the temperature correction process, and a temperature correction function may be incorporated into the acceleration sensor 12 and the angular velocity sensor 14.

The acceleration sensor 12 and the angular velocity sensor 14 may output analog signals, and, in this case, the signal processing portion 16 may A/D convert an output signal from the acceleration sensor 12 and an output signal from the angular velocity sensor 14 so as to generate sensing data.

The GPS unit 50 receives a GPS satellite signal which is transmitted from a GPS satellite which is one type of positioning satellite, performs positioning computation by using the GPS satellite signal so as to calculate a position and velocity (which is a vector including a magnitude and a direction) of the user in n frames, and outputs GPS data in which time information or positioning accuracy information is added to the calculated results to the processor 20. A method of calculating a position or velocity or a method of generating by using GPS is well known, and thus detailed description thereof will be omitted.

The geomagnetic sensor 60 detects respective geomagnetisms in the three-axis directions which intersect each other (ideally, perpendicular to each other), and outputs a digital signal (geomagnetic data) corresponding to magnitudes and directions of the detected three-axis geomagnetisms. Here, the geomagnetic sensor 60 may output an analog signal, and, in this case, the processor 20 may A/D converts an output signal from the geomagnetic sensor 60 so as to generate geomagnetic data.

The communication unit 40 performs data communication with a communication unit 140 (refer to FIG. 10) of the notification apparatus 3 or a communication unit 440 (refer to FIG. 11) of the information analysis apparatus 4. The communication unit 40 performs a process receiving a command (a command for starting or finishing measurement) transmitted from the communication unit 140 of the notification apparatus 3, and sending the command to the processor 20, a process of receiving output information during running or running result information generated by the processor 20 and transmitting the information to the communication unit 140 of the notification apparatus 3, and a process of receiving a transmission request command of the motion analysis information 350 from the communication unit 440 of the information analysis apparatus 4, sending the command to the processor 20, receiving the motion analysis information from the processor 20, and transmitting the motion analysis information to the communication unit 440 of the information analysis apparatus 4.

The processor 20 is formed of, for example, a central processing unit (CPU), a digital signal processor (DSP), or an application specific integrated circuit (ASIC), and performs various calculation processes or control processes according to various programs stored in the storage unit 30. Particularly, if a command for starting measurement is received from the notification apparatus 3 via the communication unit 40, the processor 20 receives sensing data, GPS data, and geomagnetic data from the inertial measurement unit 10, the GPS unit 50, and the geomagnetic sensor 60, respectively, and calculates a velocity, a position, an attitude angle, and the like of the user by using the data until a command for finishing the measurement. The processor 20 performs various calculation processes by using the calculated information so as to analyze motion of the user and to generate various pieces of various pieces of motion analysis information 350 which will be described later, and stores the information in the storage unit 30. The processor 20 performs a process of generating output information during running or running result information by using the generated motion analysis information 350, and sending the information to the communication unit 40.

If a transmission request command of the motion analysis information 350 is received from the information analysis apparatus 4 via the communication unit 40, the processor 20 performs a process of reading motion analysis information designated by the transmission request command from the storage unit 30, and sending the motion analysis information to the communication unit 440 of the information analysis apparatus 4 via the communication unit 40.

The storage unit 30 is formed of, for example, recording media such as a read only memory (ROM), a flash ROM, a hard disk, a hard disk, and a memory card, storing programs or data, and a random access memory (RAM) serving as a work area of the processor 20. The storage unit 30 (any recording medium) stores a motion analysis program which is read by the processor 20 and is used to perform a motion analysis process (an example of a motion analysis method or an example of analysis step). The motion analysis program includes an inertial navigation calculation program for performing an inertial navigation calculation process, and a motion analysis information generation program for performing a motion analysis information generation process.

The storage unit 30 stores a sensing data table, a GPS data table, a geomagnetic data table, a calculated data table, motion analysis information, and the like.

The sensing data table is a data table in which sensing data (a detection result in the inertial measurement unit 10) received by the processor 20 from the inertial measurement unit 10 is stored in a time series. If measurement is started, the processor 20 adds new sensing data to the sensing data table whenever a sampling cycle Δt (for example, 20 ms or 10 ms) elapses. The processor 20 corrects an acceleration bias and an angular velocity bias which are estimated according to error estimation (which will be described later) using the extended Karman filter, and updates the sensing data table by overwriting the corrected acceleration and angular velocity to the sensing data table.

The GPS data table is a data table in which GPS data (a detection result in the GPS unit (GPS sensor) 50) received by the processor 20 from the GPS unit 50 is stored in a time series. If measurement is started, the processor 20 adds GPS data whenever the GPS data is acquired (for example, every second in an asynchronous manner with acquisition timing of sensing data) so as to update the GPS data table.

The geomagnetic data table is a data table in which geomagnetic data (a detection result in the geomagnetic sensor) received by the processor 20 from the geomagnetic sensor 60 is stored in a time series. If measurement is started, the processor 20 adds new geomagnetic data to the geomagnetic data table 330 whenever the sampling cycle Δt (for example, 10 ms) elapses.

The calculated data table is a data table in which a velocity, a position, and an attitude angle calculated by the processor 20 by using the sensing data are stored in a time series. If measurement is started, the processor 20 calculates a velocity, a position, and an attitude angle whenever new sensing data is acquired, that is, the sampling cycle Δt elapses, and adds new calculated data to the calculated data table. The processor 20 corrects a velocity, a position, and an attitude angle by using a velocity error, a position error, and an attitude angle error which are estimated according to error estimation using the extended Karman filter, and updates the calculated data table by overwriting the corrected velocity, position and attitude angle to the calculated data table.

The motion analysis information 350 is various pieces of information regarding the motion of the user, and includes each item of input information 351, each item of basic information 352, each item of first analysis information 353, each item of second analysis information 354, each item of left-right difference ratio 355, and the like, generated by the processor 20. Details of the various information pieces will be described later.

1-3-2. Functional Configuration of Processor

Figure 4:
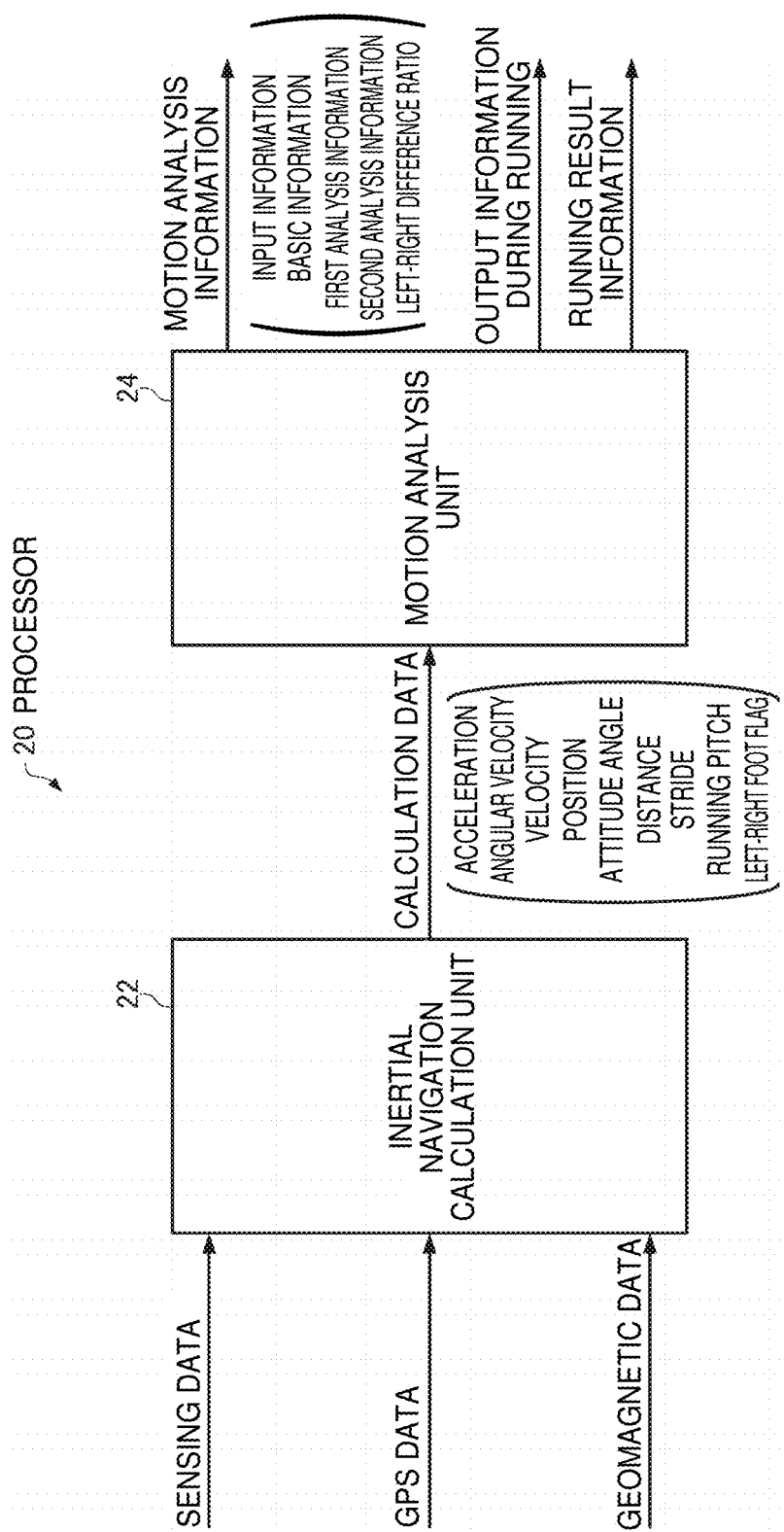
FIG. 4 is a functional block diagram illustrating a configuration example of a processor of the motion analysis apparatus.

FIG. 4 is a functional block diagram illustrating a configuration example of the processor 20 of the motion analysis apparatus 2. In the present embodiment, the processor 20 functions as an inertial navigation calculation unit 22 and a motion analysis unit 24 by executing the motion analysis program stored in the storage unit 30. However, the processor 20 may receive the motion analysis program stored in any storage device (recording medium) via a network or the like, and execute the motion analysis information.

The inertial navigation calculation unit 22 performs inertial navigation calculation by using sensing data (a detection result in the inertial measurement unit 10), GPS data (a detection result in the GPS unit 50), and geomagnetic data (a detection result in the geomagnetic sensor 60), so as to calculate an acceleration, an angular velocity, a velocity, a position, an attitude angle, a distance, a stride, and a running pitch, and outputs calculation data including the calculation results. The calculation data output from the inertial navigation calculation unit 22 is stored in the storage unit 30 in time order. Details of the inertial navigation calculation unit 22 will be described later.

The motion analysis unit 24 analyzes motion of the user during running by using the calculation data (the calculation data stored in the storage unit 30) output from the inertial navigation calculation unit 22, and generates the motion analysis information 350 (the input information 351, the basic information 352, the first analysis information 353, the second analysis information 354, a left-right difference ratio, and the like which will be described later) which is analysis result information. The motion analysis information 350 generated by the motion analysis unit 24 is stored in the storage unit 30 in time order.

The motion analysis unit 24 generates output information during running which is output during the user's running (specifically, until the inertial measurement unit 10 finishes measurement from starting of the measurement) by using the generated motion analysis information 350. The output information during running generated by the motion analysis unit 24 is transmitted to the notification apparatus 3 via the communication unit 40.

The motion analysis unit 24 generates running result information which is information regarding a running result when the user's running is finished (specifically, when the inertial measurement unit 10 finishes measurement) by using the motion analysis information 350 generated during running. The running result information generated by the motion analysis unit 24 is transmitted to the notification apparatus 3 via the communication unit 40.

1-3-3. Functional Configuration of Inertial Navigation Calculation Unit

Figure 5:
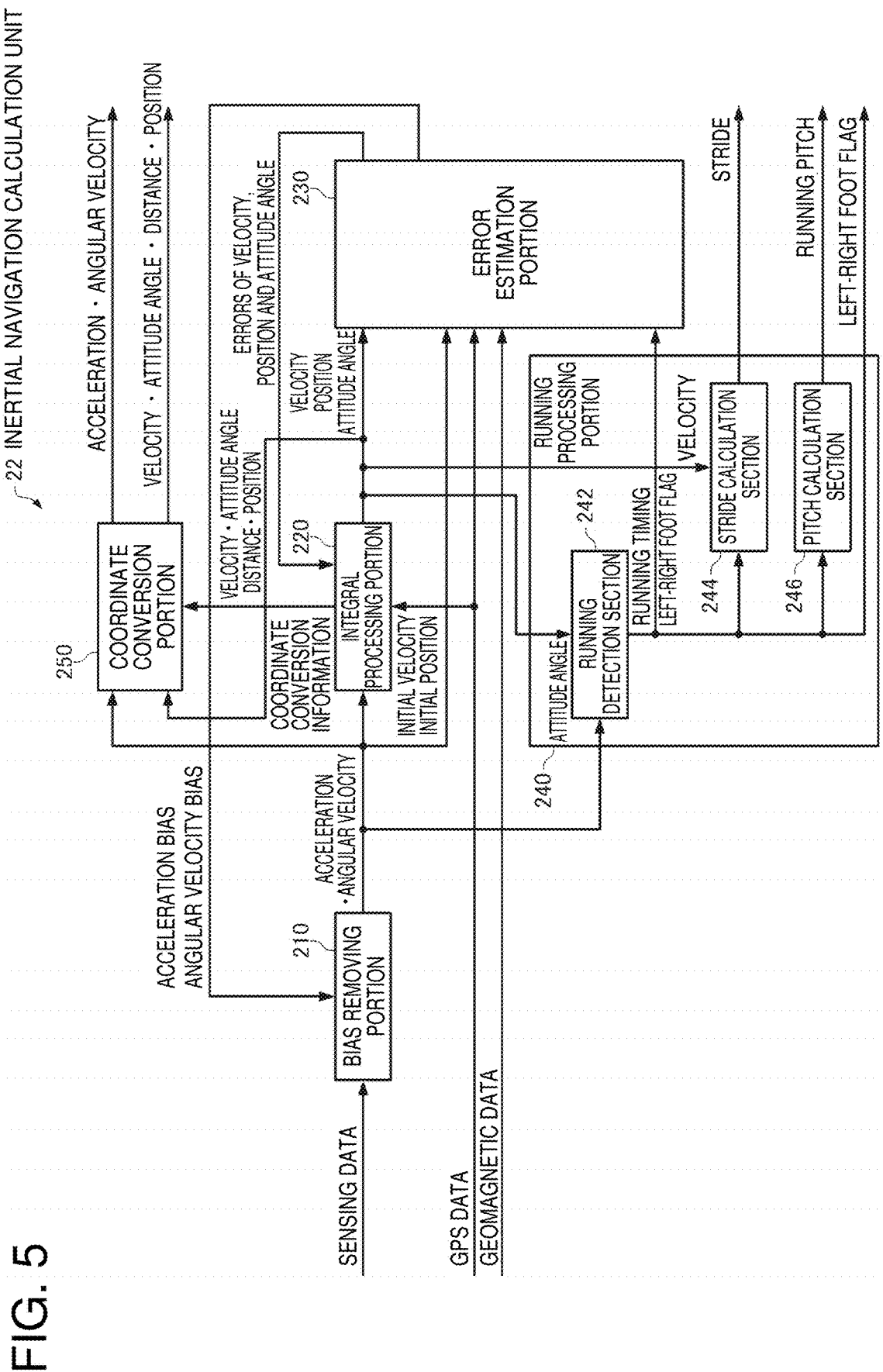
FIG. 5 is a functional block diagram illustrating a configuration example of an inertial navigation calculation unit.

FIG. 5 is a functional block diagram illustrating a configuration example of the inertial navigation calculation unit 22. In the present embodiment, the inertial navigation calculation unit 22 includes a bias removing portion 210, an integral processing portion 220, an error estimation portion 230, a running processing portion 240, and a coordinate conversion portion 250. However, the inertial navigation calculation unit 22 of the present embodiment may have a configuration in which some of the constituent elements are deleted or changed, or other constituent elements may be added thereto.

The bias removing portion 210 subtracts an acceleration bias $b_a$ and an angular velocity bias $b_\omega$ estimated by the error estimation portion 230 from three-axis accelerations and three-axis angular velocities included newly acquired sensing data, so as to perform a process of correcting the three-axis accelerations and the three-axis angular velocities. Since estimated values of the acceleration bias $b_a$ and the angular velocity bias $b_\omega$ are not present in an initial state right after measurement is started, the bias removing portion 210 computes initial biases by using sensing data from the inertial measurement unit assuming that an initial state of the user is a stoppage state.

The integral processing portion 220 performs a process of calculating a velocity $v^e$, a position $p^e$, and attitude angles (a roll angle $\phi_{be}$, a pitch angle $\theta_{be}$, and a yaw angle $\psi_{be}$) of the e frame on the basis of the accelerations and the angular velocities corrected by the bias removing portion 210. Specifically, first, the integral processing portion 220 sets an initial velocity to zero assuming that an initial state of the user is a stoppage state, or calculates an initial velocity by using the velocity included in the GPS data and also calculates an initial position by using the position included in the GPS data. The integral processing portion 220 specifies a gravitational acceleration direction on the basis of the three-axis accelerations of the b frame corrected by the bias removing portion 210 so as to calculate initial values of the roll angle $\phi_{be}$ and the pitch angle $\theta_{be}$, also calculates an initial value of the yaw angle $\psi_{be}$ on the basis of the velocity including the GPS data, and sets the calculated initial values as initial attitude angles. In a case where the GPS data cannot be obtained, an initial value of the yaw angle $\psi_{be}$ is set to, for example, zero. The integral processing portion 220 calculates an initial value of a coordinate conversion matrix (rotation matrix) $C_b^e$ from the b frame into the e frame, expressed by Equation (1) on the basis of the calculated initial attitude angles.

$$C_b^e = \begin{bmatrix} \cos\theta_{be}\cdot\cos\varphi_{be} & \cos\theta_{be}\cdot\sin\varphi_{be} & -\sin\theta_{be} \\ \sin\phi_{be}\cdot\sin\theta_{be}\cdot\cos\varphi_{be} - \cos\phi_{be}\cdot\sin\varphi_{be} & \sin\phi_{be}\cdot\sin\theta_{be}\cdot\sin\varphi_{be} + \cos\phi_{be}\cdot\cos\varphi_{be} & \sin\phi_{be}\cdot\cos\theta_{be} \\ \cos\phi_{be}\cdot\sin\theta_{be}\cdot\cos\varphi_{be} + \sin\phi_{be}\cdot\sin\varphi_{be} & \cos\phi_{be}\cdot\sin\theta_{be}\cdot\sin\varphi_{be} - \sin\phi_{be}\cdot\cos\varphi_{be} & \cos\phi_{be}\cdot\cos\theta_{be} \end{bmatrix} \quad (1)$$

Then, the integral processing portion 220 integrates the three-axis angular velocities corrected by the bias removing portion 210 so as to calculate the coordinate conversion matrix $C_b^e$, and calculates attitude angles by using Equation (2).

$$\begin{bmatrix} \phi_{be} \\ \theta_{be} \\ \varphi_{be} \end{bmatrix} = \begin{bmatrix} \arctan2(C_b^e(2,3), C_b^e(3,3)) \\ -\arcsin C_b^e(1,3) \\ \arctan2(C_b^e(1,2), C_b^e(1,1)) \end{bmatrix} \quad (2)$$

The integral processing portion 220 converts the three-axis accelerations of the b frame corrected by the bias removing portion 210 into three-axis accelerations of the e frame by using the coordinate conversion matrix $C_b^e$, and removes an gravitational acceleration component therefrom for integration so as to calculate the velocity $v^e$ of the e frame. The integral processing portion 220 integrates the velocity $v^e$ of the e frame so as to calculate the position $p^e$ of the e frame.

The integral processing portion 220 performs a process of correcting the velocity $v^e$, the position $p^e$, and the attitude angles by using a velocity error $\delta v^e$, a position error $\delta p^e$, and attitude angle errors $\varepsilon^e$ estimated by the error estimation portion 230, and also performs a process of computing a distance by integrating the corrected velocity $v^e$.

The integral processing portion 220 also calculates a coordinate conversion matrix $C_b^m$ from the b frame into the m frame, a coordinate conversion matrix $C_e^m$ from the e frame into the m frame, and a coordinate conversion matrix $C_e^n$ from the e frame into the n frame. The coordinate conversion matrices are used for a coordinate conversion process in the coordinate conversion portion 250 which will be described later as coordinate conversion information.

The error estimation portion 230 estimates an error of an index indicating a state of the user by using the velocity and/or the position, and the attitude angles calculated by the integral processing portion 220, the acceleration or the angular velocity corrected by the bias removing portion 210, the GPS data, the geomagnetic data, and the like. In the present embodiment, the error estimation portion 230 estimates errors of the velocity, the attitude angles, the acceleration, the angular velocity, and the position by using the extended Karman filter. In other words, the error estimation portion 230 uses an error (velocity error) $\delta v^e$ of the velocity $v^e$ calculated by the integral processing portion 220, errors (attitude angle errors) $\varepsilon^e$ of the attitude angles calculated by the integral processing portion 220, the acceleration bias $b_a$, the angular velocity bias $b_\omega$, and an error (position error) $\delta p^e$ of the position $p^e$ calculated by the integral processing portion 220, as state variables of the extended Karman filter, and a state vector X is defined as in Equation (3).

$$x = \begin{bmatrix} \delta v^e \\ \varepsilon^e \\ b_a \\ b_\omega \\ \delta p^e \end{bmatrix} \quad (3)$$

The error estimation portion 230 predicts state variables included in the state vector X by using a predication formula of the extended Karman filter. The predication formulae of the extended Karman filter are expressed as in Equation (4). In Equation (4), the matrix $\Phi$ is a matrix which associates the previous state vector X with the present state vector X, and is designed so that some elements thereof change every moment while reflecting attitude angles, a position, and the like. Q is a matrix indicating process noise, and each element thereof is set to an appropriate value. P is an error covariance matrix of the state variables.

$$X = \Phi X$$

$$P = \Phi P \Phi^T + Q \quad (4)$$

The error estimation portion 230 updates (corrects) the predicted state variables by update formulae of the extended Karman filter. The update formulae of the extended Karman filter are expressed as in Equation (5). Z and H are respectively an observation vector and an observation matrix, and the update formulae (5) indicate that the state vector X is corrected by using a difference between the actual observation vector Z and a vector HX predicted from the state vector X. R is a covariance matrix of observation errors, and may have predefined constant values, and may be dynamically changed. K is a Karman gain, and K increases as R decreases. From. Equation (5), as K increases (R decreases), a correction amount of the state vector X increases, and thus P decreases.

$$K = PH^T(HPH^T + R)^{-1}$$

$$X = X + K(Z - HX)$$

$$P = (I - KH)P \quad (5)$$

An error estimation method (a method of estimating the state vector X) may include, for example, the following methods.

Figure 6:
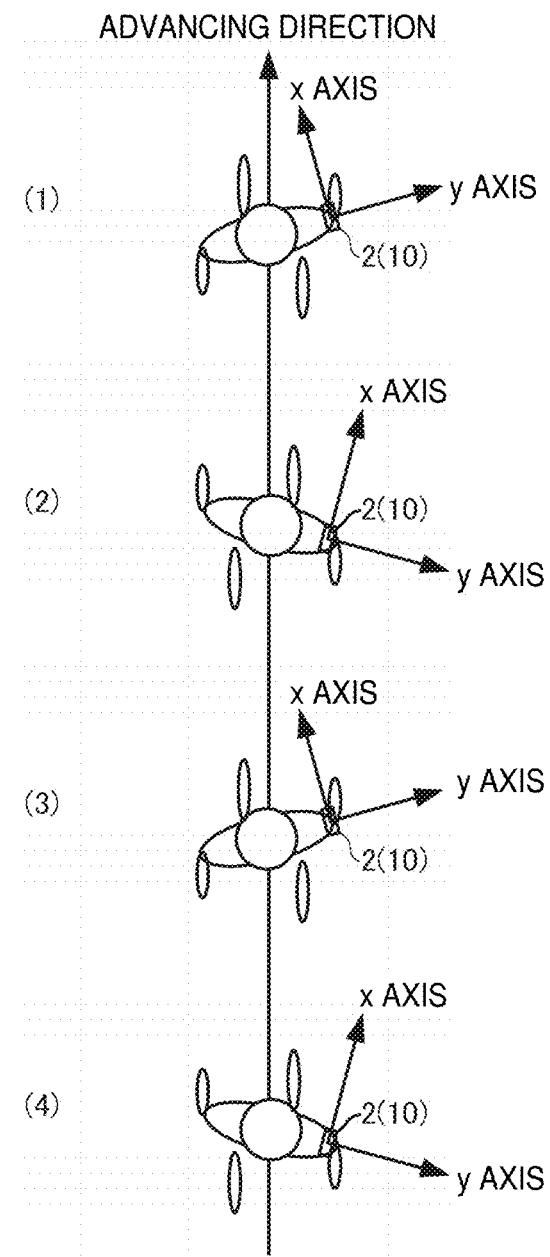
FIG. 6 is a diagram illustrating an attitude of a user during running.
Figure 7:
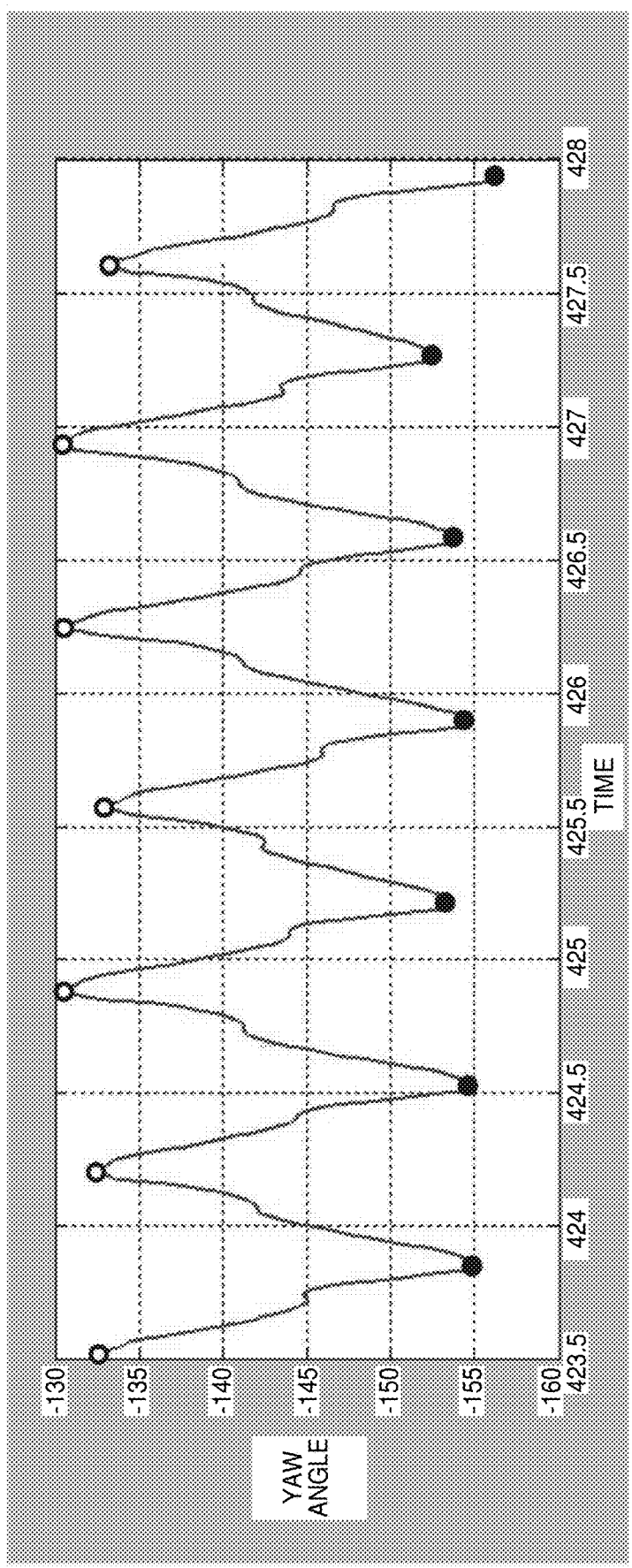
FIG. 7 is a diagram illustrating a yaw angle of the user during running.

An Error Estimation Method Using Correction on the Basis of Attitude Angle Errors:

FIG. 6 is an overhead view of movement of the user in a case where the user wearing the motion analysis apparatus 2 on the user's right waist performs a running action (going straight). FIG. 7 is a diagram illustrating an example of a yaw angle (azimuth angle) calculated by using a detection result in the inertial measurement unit 10 in a case where the user performs the running action (going straight), in which a transverse axis expresses time, and a longitudinal axis expresses a yaw angle (azimuth angle).

An attitude of the inertial measurement unit 10 relative to the user changes at any time due to the running action of the user. In a state in which the user takes a step forward with the left foot, as illustrated in (1) or (3) of FIG. 6, the inertial measurement unit 10 is tilted to the left side with respect to the advancing direction (the x axis of the m frame). In contrast, in a state in which the user takes a step forward with the right foot, as illustrated in (2) or (4) of FIG. 6, the inertial measurement unit 10 is tilted to the right side with respect to the advancing direction (the x axis of the m frame). In other words, the attitude of the inertial measurement unit 10 periodically changes every two left and right steps due to the running action of the user. In FIG. 7, for example, the yaw angle is the maximum in a state in which the user takes a step forward with the right foot (O in FIG. 7), and is the minimum in a state in which the user takes a step forward with the left foot (● in FIG. 7). Therefore, an error can be estimated assuming that the previous (two steps before) attitude angle is the same as the present attitude angle, and the previous attitude angle is a true attitude angle. In this method, the observation vector Z of Equation (5) is a difference between the previous attitude angle and the present attitude angle calculated by the integral processing portion 220, and the state vector X is corrected on the basis of a difference between the attitude angle error $\varepsilon^e$ and an observed value according to the update formulae (5) so that an error is estimated.

An Error Estimation Method Using Correction Based on the Angular Velocity Bias:

This method is a method of estimating an error assuming that the previous (two steps before) attitude angle is the same as the present attitude angle, and the previous attitude angle is not required to be a true attitude angle. In this method, the observation vector Z of Equation (5) is an angular velocity bias by using the previous attitude angle and the present attitude angle calculated by the integral processing portion 220, and the state vector X is corrected on the basis of a difference between the angular velocity bias $b_\omega$ and an observed value according to the update formulae (5).

An Error Estimation Method Using Correction Based on Azimuth Angle Error:

This method is a method of estimating an error assuming that the previous (two steps before) yaw angle (azimuth angle) is the same as the present yaw angle (azimuth angle), and the previous yaw angle (azimuth angle) is a true yaw angle (azimuth angle). In this method, the observation vector Z of Equation (5) is a difference between the previous yaw angle and the present yaw angle calculated by the integral processing portion 220, and the state vector X is corrected on the basis of a difference between an azimuth angle error $\varepsilon_z^e$ and an observed value according to the update formulae (5) so that an error is estimated.

An Error Estimation Method Using Correction Based on Stoppage:

This method is a method of estimating an error assuming that a velocity is zero when the user stops. In this method, the observation vector Z is a difference between a velocity $v^e$ calculated by the integral processing portion 220 and zero, and the state vector X is corrected on the basis of the velocity error $\delta v^e$ according to the update formulae (5) so that an error is estimated.

An Error Estimation Method Using Correction Based on Stoppage:

This method is a method of estimating an error assuming that a velocity is zero and an attitude change is also zero when the user stops. In this method, the observation vector Z is an error of the velocity $v^e$ calculated by the integral processing portion 220 and a difference between the previous attitude angle and the present attitude angle calculated by the integral processing portion 220, and the state vector X is corrected on the basis of the velocity error $\delta v^e$ and the attitude angle error $\varepsilon^e$ according to the update formulae (5) so that an error is estimated.

An Error Estimation Method Using Correction Based on an Observed Value of GPS:

This method is a method of estimating an error assuming that the velocity $v^e$, the position $p^e$, or the yaw angle $\psi_{be}$ calculated by the integral processing portion 220 is the same as a velocity, a position, or an azimuth angle (a velocity, a position, or an azimuth angle after being converted into the e frame) which is calculated by using GPS data. In this method, the observation vector Z is a difference between a velocity, a position, or a yaw angle calculated by the integral processing portion 220 and a velocity, a positional velocity, or an azimuth angle calculated by using the GPS data, and the state vector X is corrected on the basis of a difference between the velocity error $\delta v^e$, the position error $\delta p^e$, or the azimuth angle errors $\varepsilon_z^e$, and an observed value according to the update formulae (5) so that an error is estimated.

An Error Estimation Method Using Correction Based on an Observed Value in Geomagnetic Sensor:

This method is a method of estimating an error assuming that the yaw angle $\psi_{be}$ calculated by the integral processing portion 220 is the same as an azimuth angle (an azimuth angle after being converted into the e frame) calculated from the geomagnetic sensor 60. In this method, the observation vector Z is a difference between a yaw angle calculated by the integral processing portion 220 and an azimuth angle calculated by using geomagnetic data, and the state vector X is corrected on the basis of a difference between the azimuth angle errors $\varepsilon_z^e$ and an observed value according to the update formulae (5) so that an error is estimated.

Figure 8:
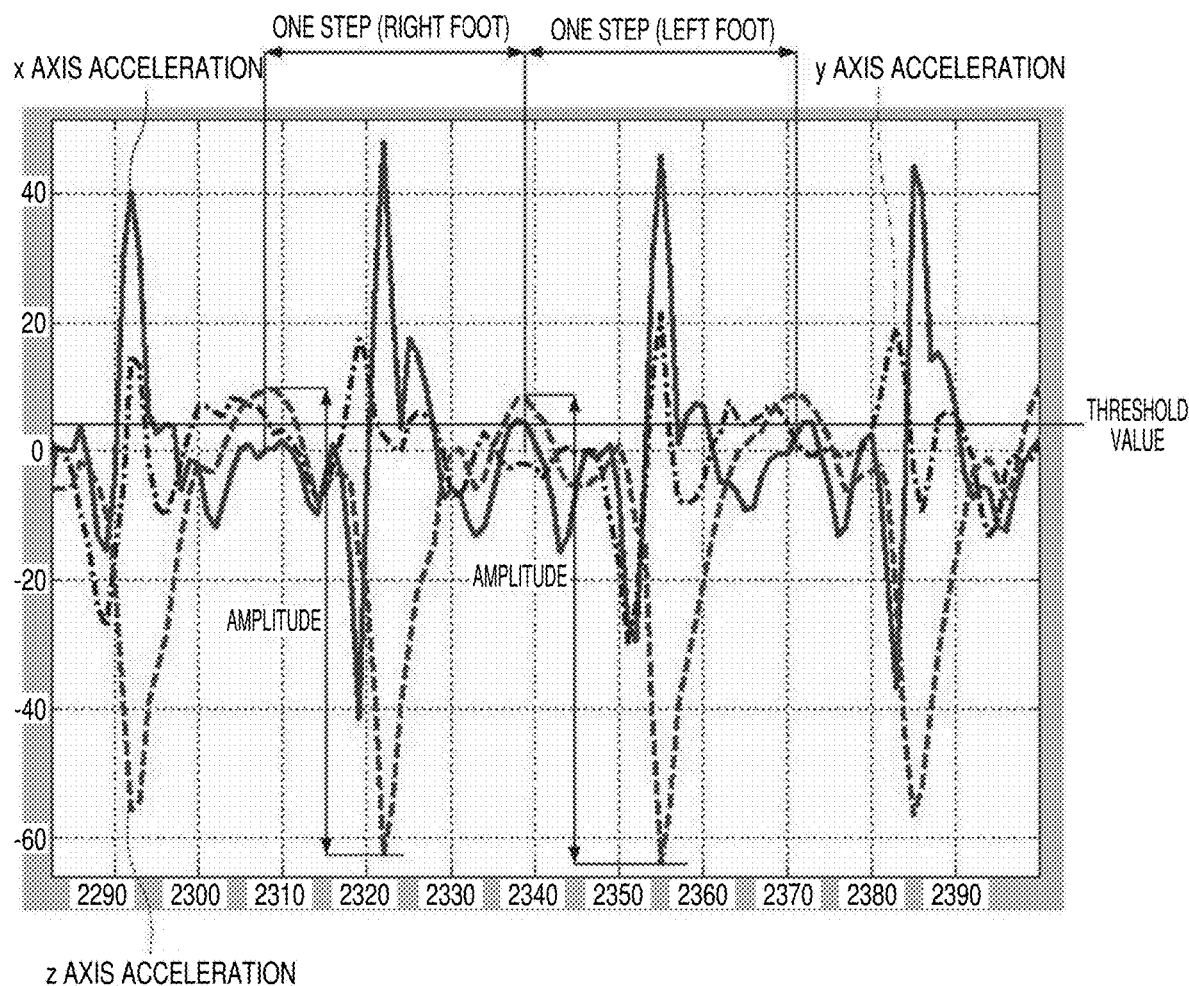
FIG. 8 is a diagram illustrating examples of three-axis accelerations of the user during running.

Referring to FIG. 5 again, the running processing portion 240 includes a running detection section 242, a stride calculation section 244, and a pitch calculation section 246. The running detection section 242 performs a process of detecting a running cycle (running timing) of the user by using a detection result (specifically, sensing data corrected by the bias removing portion 210) in the inertial measurement unit 10. As described with reference to FIGS. 6 and 7, since the user's attitude periodically changes (every two left and right steps) while the user is running, an acceleration detected by the inertial measurement unit 10 also periodically changes. FIG. 8 is a diagram illustrating an example of three-axis accelerations detected by the inertial measurement unit 10 during the user's running. In FIG. 8, a transverse axis expresses time, and a longitudinal axis expresses an acceleration value. As illustrated in FIG. 8, the three-axis accelerations periodically change, and, particularly, it can be seen that the z axis (the axis in the gravitational direction) acceleration changes periodically and regularly. The z axis acceleration reflects an acceleration obtained when the user moves vertically, and a time period from the time when the z axis acceleration becomes the maximum value which is equal to or greater than a predetermined threshold value to the time when the z axis acceleration becomes the maximum value which is equal to or greater than the predetermined threshold value next corresponds to a time period of one step.

Therefore, in the present embodiment, the running detection section 242 detects a running cycle whenever the z axis acceleration (corresponding to an acceleration obtained when the user moves vertically) detected by the inertial measurement unit 10 becomes the maximum value which is equal to or greater than the predetermined threshold value. In other words, the running detection section 242 outputs a timing signal indicating that a running cycle is detected whenever the z axis acceleration detected by the inertial measurement unit 10 becomes the maximum value which is equal to or greater than the predetermined threshold value. In practice, since a high frequency noise component is included in the three-axis accelerations detected by the inertial measurement unit 10, the running detection section 242 applies a low-pass filter to the three-axis accelerations, and detects a running cycle by using a z axis acceleration from which noise is removed.

The running detection section 242 determines which one of the left and right running cycles corresponds to the detected running cycle, and outputs a left-right foot flag (for example, an ON flag for the right foot, and an OFF flag for the left foot) indicating the corresponding running cycle. For example, as illustrated in FIG. 7, since the yaw angle is the maximum in a state in which the user takes a step forward with the right foot (O in FIG. 7), and is the minimum in a state in which the user takes a step forward with the left foot (● in FIG. 7), the running detection section 242 can determine a corresponding running cycle by using attitude angles (especially, a yaw angle) calculated by the integral processing portion 220. As illustrated in FIG. 6, when viewed from the head of the user, the inertial measurement unit 10 is rotated in a clockwise direction from a state in which the user takes a step forward with the left foot (the state (1) or (3) in FIG. 6) to a state in which the user takes a step forward with the right foot (the state (2) or (4) in FIG. 6). In contrast, the inertial measurement unit 10 is rotated in a counter-clockwise direction from a state in which the user takes a step forward with the right foot to a state in which the user takes a step forward with the left foot. Therefore, for example, the running detection section 242 may determine a corresponding running cycle on the basis of a polarity of the z axis angular velocity. In this case, in practice, since a high frequency noise component is included in the three-axis angular velocities detected by the inertial measurement unit 10, the running detection section 242 applies a low-pass filter to the three-axis angular velocities, and detects a running cycle by using a z axis angular velocity from which noise is removed.

The stride calculation section 244 calculates a stride for each of the left and right foots by using a timing signal for the running cycle and the left-right foot flag output from the running detection section 242, and a velocity or a position calculated by the integral processing portion 220, and outputs the stride for each of the left and right foots. In other words, the stride calculation section 244 integrates a velocity for each sampling cycle Δt in a time period from the start of the running cycle to the start of the next running cycle (alternatively, computes a difference between a position at the time when the running cycle is started and a position at the time when the next running cycle is started) so as to calculate and output a stride.

The pitch calculation section 246 performs a process of calculating the number of steps for one minute by using the timing signal for the running cycle output from the running detection section 242, and outputting the number of steps as a running pitch. In other words, the pitch calculation section 246 computes the number of steps per second by taking an inverse number of the running cycle, and calculates the number of steps for one minute (running pitch) by multiplying the number of steps per second by 60.

The coordinate conversion portion 250 performs a coordinate conversion process of converting the three-axis accelerations and the three-axis angular velocities of the b frame corrected by the bias removing portion 210 into three-axis accelerations and three-axis angular velocities of them frame, respectively, by using the coordinate conversion information (coordinate conversion matrix $C_b^m$) from the b frame into them frame, calculated by the integral processing portion 220. The coordinate conversion portion 250 performs a coordinate conversion process of converting the velocities in the three-axis directions, the attitude angles about the three axes, and the distances in the three-axis directions of the e frame calculated by the integral processing portion 220 into velocities in the three-axis directions, attitude angles about the three axes, and distances in the three-axis directions of them frame, respectively, by using the coordinate conversion information (coordinate conversion matrix $C_e^m$) from the e frame into them frame, calculated by the integral processing portion 220. The coordinate conversion portion 250 performs a coordinate conversion process of converting the position of the e frame calculated by the integral processing portion 220 into a position of the n frame, respectively, by using the coordinate conversion information (coordinate conversion matrix $C_e^n$) from the e frame into the n frame, calculated by the integral processing portion 220.

The inertial navigation calculation unit 22 outputs calculation data (stores the calculation data in the storage unit 30) including information regarding the accelerations, the angular velocities, the velocities, the position, the attitude angles, and the distances having undergone the coordinate conversion in the coordinate conversion portion 250, and the stride, the running pitch, and the left-right foot flag calculated by the running processing portion 240.

1-3-4. Functional Configuration of Motion Analysis Unit

Figure 9:
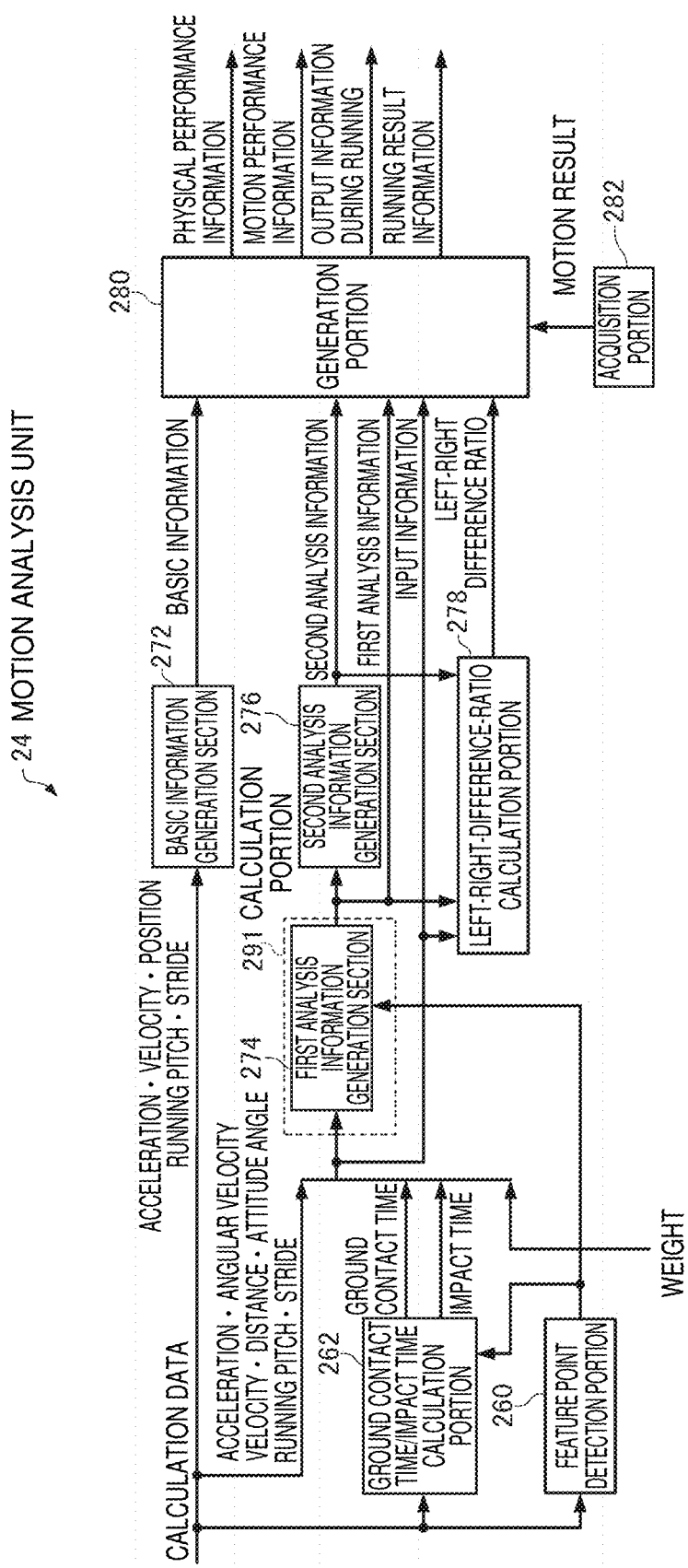
FIG. 9 is a functional block diagram illustrating a configuration example of a motion analysis unit.

FIG. 9 is a functional block diagram illustrating a configuration example of the motion analysis unit 24. In the present embodiment, the motion analysis unit 24 includes a feature point detection portion 260, a ground contact time/impact time calculation portion 262, a basic information generation portion 272, a calculation portion 291, a left-right-difference-ratio calculation portion 278, and a generation portion 280. However, the motion analysis unit 24 of the present embodiment may have a configuration in which some of the constituent elements are deleted or changed, or other constituent elements may be added thereto.

The feature point detection portion 260 performs a process of detecting a feature point in the running motion of the user by using the calculation data. The feature point in the running motion of the user is, for example, landing (which may be set as appropriate such as a time point at which a part of the sole contacts the ground, a time point at which the entire sole contacts the ground, any time point between the time at which the toe of the foot contact the ground and the time at which the heel of the foot leaves the ground, any time point between the time when the heel of the foot contact the ground and the time when the toe of the foot leaves the ground, any time point between the time when the heel of the foot contact the ground and the time when the toe of the foot leaves the ground, or a time period in which the entire sole is contacting the ground). Alternatively, a feature point in the running motion of the user is, for example, stepping (a state in which the user's weight is applied to the foot most), or taking-off (which may be set as appropriate such as a time point at which a part of the sole leaves the ground, a time point at which the entire sole leaves the ground, any time point between the time when the heel of the foot contact the ground and the time when the toe of the fool leaves the ground, or any time point between the time when the heel of the foot contact the ground and the time when the toe of the foot leaves the ground). Specifically, the feature point detection portion 260 separately detects a feature point at the running cycle for the right foot and a feature point at the running cycle for the left foot by using the left-right foot flag included in the calculation data. For example, the feature point detection portion 260 may detect landing at a timing at which the vertical acceleration (a detected value on the z axis in the acceleration sensor 12) changes from a positive value to a negative value, may detect stepping at a time point at which the acceleration in the advancing direction has a peak after the vertical acceleration has a peak in the negative direction from the landing, and may detect taking-off at a time point at which the vertical acceleration changes from a negative value to a positive value.

The ground contact time/impact time calculation portion 262 performs a process of calculating each value of a ground contact time and an impact time with the timing at which the feature point is detected by the feature point detection portion 260 as a reference, by using the calculation data. For example, the ground contact time/impact time calculation portion 262 determines whether the present calculation data corresponds to calculation data for the right foot running cycle or calculation data for the left foot running cycle on the basis of the left-right foot flag included in the calculation data, and calculates each value of the ground contact time and the impact time with the timing at which the feature point is detected by the feature point detection portion 260 as a reference, for each of the right foot running cycle and the left foot running cycle. Details of definition and a calculation method of the ground contact time and the impact time will be described later.

The basic information generation portion 272 performs a process of generating basic information regarding the motion of the user by using the information regarding the acceleration, the velocity, the position, the stride, and the running pitch included in the calculation data. Here, the basic information 352 includes respective items such as the running pitch, the stride, the running velocity, the elevation, the running distance, and the running time (lap time). Specifically, the basic information generation portion 272 outputs the running pitch and the stride included in the calculation data as a running pitch and a stride of the basic information. The basic information generation portion 272 calculates the present value or an average value during running of the running velocity, the elevation, the running velocity, and the running time (lap time) by using some or all of the acceleration, the velocity, the position, the running pitch, and the stride included in the calculation data.

The calculation portion 291 calculates kinetic energy of the user on the basis of an output from an inertial sensor (inertial measurement unit 10) attached to the user. In the example illustrated in FIG. 9, the calculation portion 291 is configured to include a first analysis information generation section 274. The first analysis information generation section 274 performs a process of analyzing the motion of the user with the timing at which the feature point is detected by the feature point detection portion 260 as a reference, by using the input information 351, so as to generate first analysis information.

The input information 351 includes respective items such as the advancing direction acceleration, the advancing direction velocity, the advancing direction distance, the vertical acceleration, the vertical velocity, the vertical distance, the horizontal acceleration, the horizontal velocity, the horizontal distance, the attitude angles (a roll angle, a pitch angle, and a yaw angle), the angular velocities (in a roll direction, a pitch direction, and a yaw direction), the running pitch, the stride, the ground contact time, the impact time, and the weight. The weight is input by the user, and the ground contact time and the impact time are calculated by the ground contact time/impact time calculation portion 262, and the other items are included in the calculation data.

The first analysis information 353 includes respective items such as brake amounts in landing (a brake amount 1 in landing and a brake amount 2 in landing), directly-below landing ratios (a directly-below landing ratio 1, a directly-below landing ratio 2, and a directly-below landing ratio 3), propulsion efficiency (propulsion efficiency 1, propulsion efficiency 2, propulsion efficiency 3, and propulsion efficiency 4), kinetic energy, a landing impact, running performance, a forward tilt angle, timing coincidence, and the slow turnover. Each item of the first analysis information 353 indicates a running state of the user. Details of the content of each item and a computation method of the first analysis information 353 will be described later.

The first analysis information generation section 274 calculates a value of each item of the first analysis information for the respective left and right sides of the user's body. Specifically, the first analysis information generation section 274 calculates each item included in the first analysis information for the right foot running cycle and the left foot running cycle depending on whether the feature point detection portion 260 has detected the feature point at the right foot running cycle or the feature point at the left foot running cycle. The first analysis information generation section 274 calculates an average value or a total value of the left and right sides for each item included in the first analysis information.

The second analysis information generation section 276 performs a process of generating second analysis information by using the first analysis information generated by the first analysis information generation section 274. Here, the second analysis information 354 includes respective items such as energy loss, energy efficiency, and a burden on the body. Details of the content of each item and a calculation method of the second analysis information 354 will be described later. The second analysis information generation section 276 calculates a value of each item of the second analysis information 354 for the right foot running cycle and the left foot running cycle. The second analysis information generation section 276 calculates an average value or a total value of the left and right sides for each item included in the second analysis information.

The left-right-difference-ratio calculation portion 278 performs a process of calculating a left-right difference ratio which is an index indicating a balance between the left and right sides of the user's body by using values at the right foot running cycle and values at the left foot running cycle with respect to the running pitch, the stride, the ground contact time, and the impact time included in the input information 351, all the items of the first analysis information 353, and all the items of the second analysis information 354. Details of the content and a computation method of the left-right difference ratio 355 will be described later.

The generation portion 280 generates motion performance information which is information regarding motion performance of the user on the basis of the kinetic energy of the second analysis information 354 and the running distance and the running time (lap time) which are motion results (running results). In the example illustrated in FIG. 9, the motion analysis unit 24 is configured to include an acquisition portion 282 which acquires the running distance and the running time. The generation portion 280 generates the motion performance information on the basis of the running distance and the running time acquired by the acquisition portion 282.

The generation portion 280 generates physical performance information which is information regarding physical performance of the user on the basis of the kinetic energy of the second analysis information 354 and the running distance and the running time (lap time) which are motion results (running results). The generation portion 280 generates the physical performance information on the basis of the running distance and the running time acquired by the acquisition portion 282.

The generation portion 280 performs a process of generating output information during running which is information output during the user's running by using the basic information 352, the input information 351, the first analysis information 353, the second analysis information 354, the left-right difference ratio 355, and the like. The "running pitch", the "stride", the "ground contact time", and the "impact time" included in the input information 351, all of the items of the first analysis information 353, and all of the items of the second analysis information 354 and the left-right difference ratio 355 are motion indexes used to evaluate a running technique of the user, and the output information during running includes information regarding values of some or all of the motion indexes. The motion indexes included in the output information during running may be set in advance, and may be selected by the user operating the notification apparatus 3. The output information during running may include some or all of the running velocity, the elevation, the running distance, and the running time (lap time) included in the basic information 352.

The generation portion 280 generates running result information which is information regarding a running result of the user by using the basic information 352, the input information 351, the first analysis information 353, the second analysis information 354, the left-right difference ratio 355, and the like. For example, the generation portion 280 may generate running result information including information regarding an average value of each motion index during the user's running (during measurement in the inertial measurement unit 10). The running result information may include some or all of the running velocity, the elevation, the running distance, and the running time (lap time). The generation portion 280 transmits the output information during running to the notification apparatus 3 via the communication unit 40 during the user's running, and transmits the running result information to the notification apparatus 3 when the user's running is finished.

1-3-5. Input Information

Hereinafter, a description will be made of details of each item of the input information 351.

Advancing Direction Acceleration, Vertical Acceleration, and Horizontal Acceleration The "advancing direction" is an advancing direction (the x axis direction of them frame) of the user, the "vertical direction" is a perpendicular direction (the z axis direction of the m frame), and the "horizontal direction" is a direction (the y axis direction of the m frame) orthogonal to both the advancing direction and the vertical direction. The advancing direction acceleration, the vertical acceleration, and the horizontal acceleration are respectively an acceleration in the x axis direction of the m frame, an acceleration in the z axis direction thereof, and an acceleration in the y axis direction thereof, and are calculated by the coordinate conversion portion 250.

Advancing Direction Velocity, Vertical Velocity, and Horizontal Velocity

The advancing direction velocity, the vertical velocity, and the horizontal velocity are respectively a velocity in the x axis direction of the m frame, a velocity in the z axis direction thereof, and a velocity in the y axis direction thereof, and are calculated by the coordinate conversion portion 250. Alternatively, the advancing direction velocity, the vertical velocity, and the horizontal velocity may be respectively calculated by integrating the advancing direction acceleration, the vertical acceleration, and the horizontal acceleration.

Angular Velocities (in Roll Direction, Pitch Direction, and Yaw Direction)

The angular velocity in the roll direction, the angular velocity in the pitch direction, and the angular velocity in the yaw direction are respectively an angular velocity about the x axis of the m frame, an angular velocity about the y axis thereof, and an angular velocity about the z axis thereof, and are calculated by the coordinate conversion portion 250.

Attitude Angles (Roll Angle, Pitch Angle, and Yaw Angle)

The roll angle, the pitch angle, and the yaw angle are respectively an attitude angle about the x axis of the m frame, an attitude angle about the y axis thereof, and an attitude angle about the z axis thereof, output from the coordinate conversion portion 250, and are calculated by the coordinate conversion portion 250. Alternatively, the roll angle, the pitch angle, and the yaw angle may be respectively calculated by integrating (by performing rotation calculation on) the angular velocity in the roll direction, the angular velocity in the pitch direction, and the angular velocity in the yaw direction.

Advancing Direction Distance, Vertical Distance, and Horizontal Distance

The advancing direction distance, the vertical distance, and the horizontal distance are respectively a movement distance in the x axis direction of the m frame, a movement distance in the y axis direction thereof, and a movement distance in the z direction thereof from a desired position (for example, a position right before the user's running), and are calculated by the coordinate conversion portion 250.

Running Pitch

The running pitch is a motion index defined as the number of steps per one minute, and is calculated by the pitch calculation section 246. Alternatively, the running pitch may be calculated by dividing an advancing direction distance for one minute by the number of steps.

Stride

The stride is a motion index defined as one step, and is calculated by the stride calculation section 244. Alternatively, the stride may be calculated by dividing an advancing direction distance for one minute by the running pitch.

Ground Contact Time

The ground contact time is a motion index defined as time taken from landing to taking-off (kicking), and is calculated by the ground contact time/impact time calculation portion 262. The taking-off (kicking) indicates the time when the toe leaves the ground. The ground contact time has a high correlation with a running speed, and may thus be used as running performance of the first analysis information 353.

Impact Time

The impact time is a motion index defined as time when an impact caused by landing is being applied to the body, and is calculated by the ground contact time/impact time calculation portion 262. The impact time may be computed as the impact time=(time point at which advancing direction acceleration is the minimum during one step–a time point of landing).

Weight

The weight is a user's weight, and a numerical value thereof is input by the user operating the operation unit 150 (refer to FIG. 10) before running.

1-3-6. First Analysis Information

Hereinafter, a description will be made of details of each item of the first analysis information calculated by the first analysis information generation section 274.

Brake Amount 1 in Landing

The brake amount 1 in landing is a motion index defined as an amount of velocity which is reduced due to landing, and the brake amount 1 in landing may be computed as (advancing direction velocity before landing)−(advancing direction lowest velocity after landing). The velocity in the advancing direction is reduced due to landing, and the lowest point in the advancing direction velocity after the landing during one step is the advancing direction lowest velocity.

Brake Amount 2 in Landing

The brake amount 2 in landing is a motion index defined as an amount of the lowest acceleration in the advancing direction, caused by landing, and matches the advancing direction lowest acceleration after landing during one step. The lowest point of the advancing direction acceleration after landing during one step is the advancing direction lowest acceleration.

Directly-Below Landing Ratio 1

The directly-below landing ratio 1 is a motion index which expresses whether landing is performed directly below the body. If the landing is performed directly under the body, a brake amount is reduced at the time of landing, and thus efficient running can be performed. Typically, since a brake amount increases according to velocity, only the brake amount is not sufficient as indexes, but the directly-below landing ratio 1 is an index which can be expressed in a ratio, and thus the same evaluation can be performed even if velocity changes by using the directly-below landing ratio 1. If the advancing direction acceleration (negative acceleration) and the vertical acceleration in landing are used, and $\alpha$ is set as $\alpha$=arctan (advancing direction acceleration in landing/vertical acceleration in landing), the directly-below landing ratio 1 may be computed as the directly-below landing ratio 1=cos $\alpha \times 100(\%)$. Alternatively, an ideal angle $\alpha'$ may be calculated by using data of a plurality of people who run fast, and the directly-below landing ratio 1 may be computed as the directly-below landing ratio 1=$\{1-|(\alpha'-\alpha)/\alpha'|\}\times 100(\%)$.

Directly-Below Landing Ratio 2

The directly-below landing ratio 2 is a motion index which expresses whether or not landing is performed directly below the body as the extent in which velocity is reduced in landing, and is computed as the directly-below landing ratio 2=(advancing direction lowest velocity after landing/advancing direction velocity right before landing)$\times 100(\%)$.

Directly-Below Landing Ratio 3

The directly-below landing ratio 3 is a motion index which expresses whether or not landing is performed directly below the body as a distance or time until the foot comes directly under the body from landing. The directly-below landing ratio 3 may be computed as the directly-below landing ratio 3=(advancing direction distance when the foot comes directly below the body)−(advancing direction distance in landing), or the directly-below landing ratio 3=(time point when the foot comes directly below the body)−(time point in landing). There is a timing at which the vertical acceleration has a peak in the negative direction after landing (a point where the vertical acceleration changes from a positive value to a negative value), and this timing may be determined as being a timing (time point) at which the foot comes directly below the body.

The directly-below landing ratio 3 may be defined as the directly-below landing ratio 3=arctan(the distance until the foot comes directly below the body/the height of the waist). Alternatively, the directly-below landing ratio 3 may be defined as the directly-below landing ratio 3=(1−the distance until the foot comes directly below the body/a movement distance from landing to kicking)$\times 100(\%)$ (a ratio occupied by the distance until the foot comes directly below the body in the movement distance during the foot's contact on the ground). Alternatively, the directly-below landing ratio 3 may be defined as the directly-below landing ratio 3=(1−the time until the foot comes directly below the body/movement time from landing to kicking)$\times 100(\%)$ (a ratio occupied by the time until the foot comes directly below the body in the movement time during the foot's contact on the ground).

Propulsion Efficiency 1

The propulsion efficiency 1 is a motion index indicating whether or not a kicking force is efficiently converted into a propulsion force. If a useless vertical movement and a useless horizontal movement are removed, efficient running is possible. Generally, since the vertical movement and the horizontal movement increase according to velocity, only the vertical movement and the horizontal movement are not sufficient, but the propulsion efficiency 1 is an index which can be expressed in a ratio, and thus the same evaluation can be performed even if velocity changes by using the propulsion efficiency 1. The propulsion efficiency 1 is computed for each of the vertical direction and the horizontal direction. If the vertical acceleration and the advancing direction acceleration in kicking are used, and $\gamma$ is set as $\gamma$=arctan (vertical acceleration in kicking/advancing direction acceleration in kicking), the vertical propulsion efficiency 1 may be computed as the propulsion efficiency 1=cos $\gamma \times 100(\%)$. Alternatively, an ideal angle $\gamma'$ may be calculated by using data of a plurality of people who run fast, and the vertical propulsion efficiency 1 may be computed as the vertical propulsion efficiency 1=$\{1-|(\gamma'-\gamma)/\gamma'|\}\times 100(\%)$. Similarly, if the horizontal acceleration and the advancing direction acceleration in kicking are used, and $\delta$ is set as $\delta$=arctan (horizontal acceleration in kicking/advancing direction acceleration in kicking), the horizontal propulsion efficiency 1 may be computed as the propulsion efficiency 1=cos $\delta \times 100(\%)$. Alternatively, an ideal angle $\delta'$ may be calculated by using data of a plurality of people who run fast, and the horizontal propulsion efficiency 1 may be computed as the horizontal propulsion efficiency 1=$\{1-|(\delta'-\delta)/\delta'|\}\times 100(\%)$.

In addition, the vertical propulsion efficiency 1 may be calculated by replacing $\gamma$ with arctan (vertical velocity in kicking/advancing direction velocity in kicking). Similarly, the horizontal propulsion efficiency 1 may be calculated by replacing $\delta$ with arctan(horizontal velocity in kicking/advancing direction velocity in kicking).

Propulsion Efficiency 2

The propulsion efficiency 2 is a motion index indicating whether or not a kicking force is efficiently converted into a propulsion force by using an angle of acceleration in stepping. If the vertical acceleration and the advancing direction acceleration in stepping are used, and $\xi$ is set as $\xi$=arctan (vertical acceleration in stepping/advancing direction acceleration in stepping), the vertical propulsion efficiency 2 may be computed as the propulsion efficiency 2=cos $\xi \times 100(\%)$. Alternatively, an ideal angle $\xi'$ may be calculated by using data of a plurality of people who run fast, and the vertical propulsion efficiency 1 may be computed as the vertical propulsion efficiency 1=$\{1-|(\xi'-\xi)/'\xi\}\times 100(\%)$. Similarly, if the horizontal acceleration and the advancing direction acceleration in kicking are used, and $\eta$ is set as $\eta$=arctan (horizontal acceleration in stepping/advancing direction acceleration in stepping), the horizontal propulsion efficiency 2 may be computed as the propulsion efficiency 2=cos $\eta \times 100(\%)$. Alternatively, an ideal angle $\eta'$ may be calculated by using data of a plurality of people who run fast, and the horizontal propulsion efficiency 2 may be computed as the horizontal propulsion efficiency 2=$\{1-|(\eta'-\eta)/\eta'|\} \times 100(\%)$.

In addition, the vertical propulsion efficiency 2 may be calculated by replacing $\xi$ with arctan (vertical velocity in stepping/advancing direction velocity in stepping). Similarly, the horizontal propulsion efficiency 2 may be calculated by replacing $\eta$ with arctan(horizontal velocity in stepping/advancing direction velocity in stepping).

Propulsion Efficiency 3

The propulsion efficiency 3 is a motion index indicating whether or not a kicking force is efficiently converted into a propulsion force by using an angle of rushing. If the highest arrival point (½ of the amplitude of the vertical distance) in the vertical direction during one step is denoted by H, and an advancing direction distance from kicking to landing is denoted by X, the propulsion efficiency 3 may be computed by using Equation (6).

$$\text{Propulsion efficiency 3}=\arcsin(\sqrt{(16H^2)/(X^2+16H^2)}) \qquad (6)$$

Propulsion Efficiency 4

The propulsion efficiency 4 is a motion index indicating whether or not a kicking force is efficiently converted into a propulsion force by using a ratio of energy used to go forward in the advancing direction to total energy which is generated during one step, and is computed as the propulsion efficiency 4=(energy used to go forward in the advancing direction/energy used for one step)×100(%). This energy is a sum of potential energy and kinetic energy.

Kinetic Energy

The kinetic energy is a motion index defined as an amount of energy which is consumed for one-step advancing, and also indicates a result obtained by integrating an amount of energy consumed for one-step advancing for a running period. The amount of energy consumption is computed as the kinetic energy=(an amount of energy consumption in the vertical direction)+(an amount of energy consumption in the advancing direction)+(an amount of energy consumption in the horizontal direction). Here, the amount of energy consumption in the vertical direction is computed as the amount of energy consumption in the vertical direction=(weight×gravity×vertical distance). The amount of energy consumption in the advancing direction is computed as the amount of energy consumption in the advancing direction=[weight×{(advancing direction highest velocity after kicking)²−(advancing direction lowest conversion after landing)²}/2]. The amount of energy consumption in the horizontal direction is computed as the amount of energy consumption in the advancing direction=[weight×{(horizontal highest velocity after kicking)²−(horizontal lowest conversion after landing)²}/2].

Landing Impact

The landing impact is a motion index indicating to what extent an impact is applied to the body due to landing, and is computed as the landing impact=(an impact force in the vertical direction+an impact force in the advancing direction+an impact force in the horizontal direction). Here, the impact force in the vertical direction is computed as the impact force in the vertical direction=(weight×vertical velocity in landing/impact time). The impact force in the advancing direction is computed as the impact force in the advancing direction={weight×(advancing direction velocity before landing−advancing direction lowest velocity after landing)/impact time}. The impact force in the horizontal direction is computed as the impact force in the horizontal direction={weight×(horizontal velocity before landing−horizontal lowest velocity after landing)/impact time}.

Running Performance

The running performance is a motion index indicating a user's running force. For example, it is known that there is a correlation between a ratio of a stride and ground contact time, and a running record (time) ("As for Ground Contact Time and Taking-Off Time in Race on 100 m Track", Journal of Research and Development for Future Athletics. 3(1):1-4, 2004.), and is computed as the running performance=(stride/ground contact time).

Forward Tilt Angle

The forward tilt angle is a motion index indicating to what extent the user's body is tilted with respect to the ground.

If the forward tilt angle is set to 0 degrees when the user stands vertically to the ground, the forward tilt angle has a positive value when the user bends forward, and the forward tilt angle has a negative value when the user bends backward. The forward tilt angle is obtained by converting a pitch angle of them frame so as to cause the same specification. Since the motion analysis apparatus 2 (inertial measurement unit 10) is mounted on the user, and may be already tilted at this time, the forward tilt angle is assumed to be 0 degrees during stoppage, and may be computed by using an amount of change therefrom.

Timing Coincidence

The timing coincidence is a motion index indicating how close to a good timing a timing of a user's feature point is. For example, a motion index indicating how close to a kicking timing a timing of waist rotation is. In the way of the slow turnover of the legs, since, when one leg reaches the ground, the other leg remains behind the body still, a case where a waist rotation timing comes after kicking may be determined as being the slow turnover of the legs. If a waist rotation timing substantially matches a kicking timing, this can be said to be good running. On the other hand, if a waist rotation timing is later than a kicking timing, this can be said to be in the way of the slow turnover of the legs.

Slow Turnover of Legs

The slow turnover of the legs is a motion index indicating to what extent a leg remains behind at the next landing point of the kicking leg. The slow turnover of the legs is computed as an angle of the femur of the hind leg when the user lands. For example, an index correlated with the slow turnover of the legs may be computed, and an angle of the femur of the hind leg when the user's leg contacts the ground may be estimated by using a correlation which is obtained in advance on the basis of the index.

The index correlated with the slow turnover of the legs is computed as (a difference between a time point at which the user's waist rotates to the maximum in the yaw direction and a time point in landing). The "time point at which the user's waist rotates to the maximum in the yaw direction" is the time of starting the next one-step action. In a case where a time from landing to the next action is long, it can be said that time is required to return the leg, and thus a phenomenon of the slow turnover of the legs occurs.

Alternatively, the index correlated with the slow turnover of the legs is computed as (a difference between a yaw angle when the user's waist rotates to the maximum in the yaw direction and the yaw angle in landing). In a case where a change in the yaw angle from landing to the next action is great, an action of returning the leg after landing is performed, and this appears in the change in the yaw angle. Thus, a phenomenon of the slow turnover of the legs occurs.

Alternatively, a pitch angle in landing may be used as the index correlated with the slow turnover of the legs. In a case where the leg lies high backward, the body is tilted forward. Thus, a pitch angle of the sensor attached to the waist increases. If a pitch angle in landing is large, a phenomenon of the slow turnover of the legs occurs.

1-3-7. Second Analysis Information

Hereinafter, a description will be made of details of each item of the second analysis information calculated by the second analysis information generation section 276.

Energy Loss

The energy loss is a motion index indicating an amount of energy which is wastefully used with respect to an amount of energy consumed for one-step advancing, and also indicates a result obtained by integrating an amount of energy which is wastefully used with respect to an amount of energy consumed for one-step advancing for a running period. The energy loss is computed as the energy loss={amount of energy consumption×(100−directly-below landing ratio)×(100−propulsion efficiency}. Here, the directly-below landing ratio is any one of the directly-below landing ratios 1 to 3, and the propulsion efficiency is any one of the propulsion efficiency 1 to the propulsion efficiency 4.

Energy Efficiency

The energy efficiency is a motion index indicating whether or not the energy consumed for one-step advancing is efficiently used as energy for going forward in the advancing direction, and also indicates a result obtained by integrating the energy for a running period. The energy efficiency is computed as the energy efficiency={(amount of energy consumption−energy loss)/(amount of energy consumption)}.

Burden on Body

The burden on the body is a motion index indicating to what extent impacts are accumulated in the body by accumulating a landing impact. An injury occurs due to accumulation of impacts, and thus likelihood of an injury can be determined by evaluating the burden on the body. The burden on the body is computed as the burden on the body=(burden on right leg+burden on left leg). The burden on the right leg may be computed by integrating landing impacts on the right leg. The burden on the left leg may be computed by integrating landing impacts on the left leg. Here, as the integration, both integration during running and integration from the past are performed.

1-3-8. Left-Right Difference Ratio (Left-Right Balance)

The left-right difference ratio 355 is a motion index indicating to what extent there is a difference between the left and right sides of the body for the running pitch, the stride, the ground contact time, the impact time, each item of the first analysis information 353, and each item of the second analysis information 354, and is assumed to indicate to what extent the left leg is deviated relative to the right leg. The left-right difference ratio is computed as the left-right difference ratio=(numerical value for left leg/numerical value for right leg×100(%)). The numerical value is a numerical value of each of the running pitch, the stride, the ground contact time, the impact time, the brake amount, the propulsion force, the directly-below landing ratio, the propulsion efficiency, the velocity, the acceleration, the movement distance, the forward tilt angle, the waist rotation angle, the waist rotation angular velocity, the amount of being tilted toward the left and right sides, the impact time, the running performance, the amount of energy consumption, the energy loss, the energy efficiency, the landing impact, and the burden on the body. The left-right difference ratio 355 also includes an average value or a variance of the respective numerical values.

1-3-9. Motion Performance Information

If the same extent of kinetic energy is used for the same motion, it can be estimated that the user has the same extent of physical performance. Even if the same extent of kinetic energy is used for the same motion, there may be a difference in a running distance and a running time depending on a difference in motion performance. Therefore, as the motion performance information, for example, a running distance and a running time for kinetic energy measured this time may be output as deviation values, and a difference from an average value may be output, on the basis of statistical data of a correspondence relationship among the kinetic energy, the running distance, and the running time.

1-4. Notification Apparatus 1-4-1. Configuration of Notification Apparatus

Figure 10:
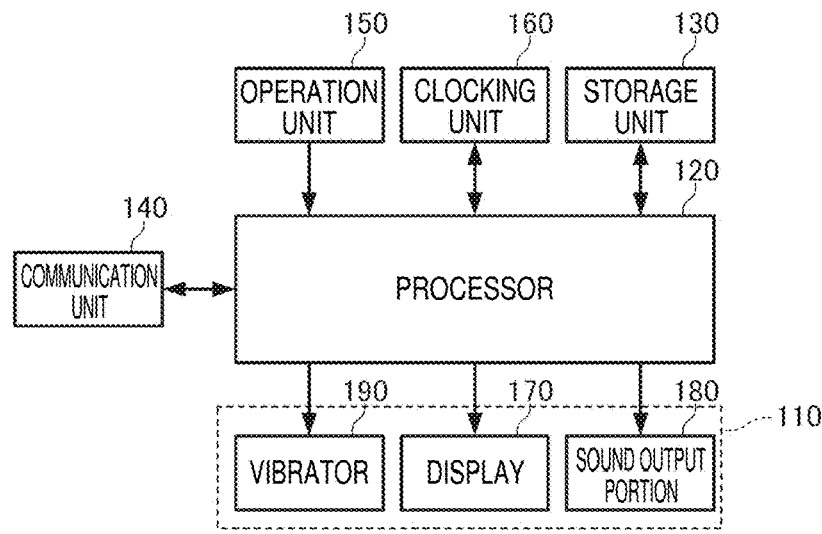
FIG. 10 is a functional block diagram illustrating a configuration example of a notification apparatus.

FIG. 10 is a functional block diagram illustrating a configuration example of the notification apparatus 3. As illustrated in FIG. 10, the notification apparatus 3 is configured to include an output unit 110, a processor 120, a storage unit 130, the communication unit 140, an operation unit 150, and a clocking unit 160. However, the notification apparatus 3 of the present embodiment may have a configuration in which some of the constituent elements are deleted or changed, or other constituent elements may be added thereto.

The storage unit 130 is formed of, for example, recording media such as a ROM, a flash ROM, a hard disk, a hard disk, and a memory card, storing programs or data, and a RAM serving as a work area of the processor 120.

The communication unit 140 performs data communication with the communication unit 40 (refer to FIG. 3) of the motion analysis apparatus 2 or the communication unit 440 (refer to FIG. 11) of the information analysis apparatus 4, and performs a process of receiving a command (a command for starting or finishing measurement or the like) corresponding to operation data from the processor 120 and transmitting the command to the communication unit 40 of the motion analysis apparatus 2, a process of receiving output information during running or running result information transmitted from the communication unit 40 of the motion analysis apparatus 2 and sending the information to the processor 120, a process of information regarding a target value of each motion index transmitted from the communication unit 440 of the information analysis apparatus 4 and sending the information to the processor 120, and the like.

The operation unit 150 performs a process of acquiring operation data (operation data such as starting or finishing of measurement or selection of display content) from the user and sending the operation data to the processor 120. The operation unit 150 may be, for example, a touch panel type display, a button key, or a microphone.

The clocking unit 160 performs a process of generating time information such as year, month, day, hour, minute, and second. The clocking unit 160 is implemented by, for example, a real time clock (RTC) IC.

The output unit 110 outputs motion performance information of the user. The output unit 110 outputs physical performance information of the user. The output unit 110 may output the motion performance information of the user in comparison with motion performance information of another user. The output unit 110 may output the physical performance information of the user in comparison with physical performance information of another user. Specific examples of outputs of motion performance information and the physical performance information will be described later. The output unit 110 may output an evaluation result which will be described later. In the example illustrated in FIG. 10, the output unit 110 is configured to include a display 170, a sound output portion 180, and a vibrator 190.

The display 170 displays image data or text data sent from the processor 120 as text, a graph, a table, animation, or other images. The display 170 is implemented by, for example, a display such as a liquid crystal display (LCD), an organic electroluminescence (EL) display, or an electrophoretic display (EPD), and may be a touch panel type display. A single touch panel type display may realize functions of the operation unit 150 and the display 170.

The sound output portion 180 outputs sound data sent from the processor 120 as a sound such as a voice or a buzzer sound. The sound output portion 180 is implemented by, for example, a speaker or a buzzer.

The vibrator 190 vibrates in response to vibration data sent from the processor 120. This vibration is transmitted to the notification apparatus 3, and the user wearing the notification apparatus 3 can feel the vibration. The vibrator 190 is implemented by, for example, a vibration motor.

The processor 120 is constituted of, for example, a CPU, a DSP, or an ASIC, and performs various calculation processes or control processes according to a program stored in the storage unit 130 (recording medium). For example, the processor 120 performs various processes (a process of sending a command for starting or finishing measurement or a command for starting or finishing the running analysis process to the communication unit 140, a process of performing display or outputting sound corresponding to the operation data, and the like) corresponding to operation data received from the operation unit 150. For example, the processor 120 performs a process of receiving output information during running from the communication unit 140 and generating text data or image data corresponding to the motion analysis information 350 and sending the data to the display 170, a process of generating sound data corresponding to the motion analysis information and sending the data to the sound output portion 180, and a process of generating vibration data corresponding to the motion analysis information and sending the data to the vibrator 190. The processor 120 performs a process of generating time image data corresponding to time information received from the clocking unit 160 and sending the time image data to the display 170, and the like.

For example, in a case where there is a motion index which is worse than a reference value, the processor 120 performs a notification with sounds or vibration, and also displays a value of the motion index worse than the reference value on the display 170. The processor 120 may generate different types of sounds or vibration according to the type of motion index worse than the reference value, and may change the type of sound or vibration according to the extent to which each motion index is worse than the reference value. In a case where there are a plurality of motion indexes worse than reference values, the processor 120 may generate sounds or vibration of the type corresponding to the worst motion index, and may also display information regarding values of all motion indexes worse than the reference values and information regarding the reference values on the display 170.

A motion index compared with a reference value may be all motion indexes included in output information during running, may be only a specific motion index set in advance, and may be selected by the user operating the operation unit 150 or the like.

Even if the user does not view the information displayed on the display 170, the user can continuously run while recognizing the worst motion index and the extent of being worse on the basis of the type of sound or vibration. When viewing the information displayed on the display 170, the user can accurately recognize differences between values of all motion indexes worse than reference values, and the target values.

A motion index which is a sound or vibration generation target may be selected from among motion indexes compared with reference values by the user operating the operation unit 150 or the like. Also in this case, for example, information regarding all motion indexes worse than the reference values and information regarding the reference values may be displayed on the display 170.

The user may set a notification cycle via the operation unit 150 (for example, setting such as generation of sounds or vibration for five seconds every minute), and the processor 120 may send a notification to the user according to the set notification cycle.

In the present embodiment, the processor 120 acquires running result information transmitted from the motion analysis apparatus 2 via the communication unit 140, and displays the running result information on the display 170. The processor 120 displays an average value of each motion index in the user's running, included in the running result information, on the display 170. The user can immediately recognize goodness and badness of each motion index while viewing the display 170 after the running is finished (after a measurement finishing operation is performed).

Figure 11:
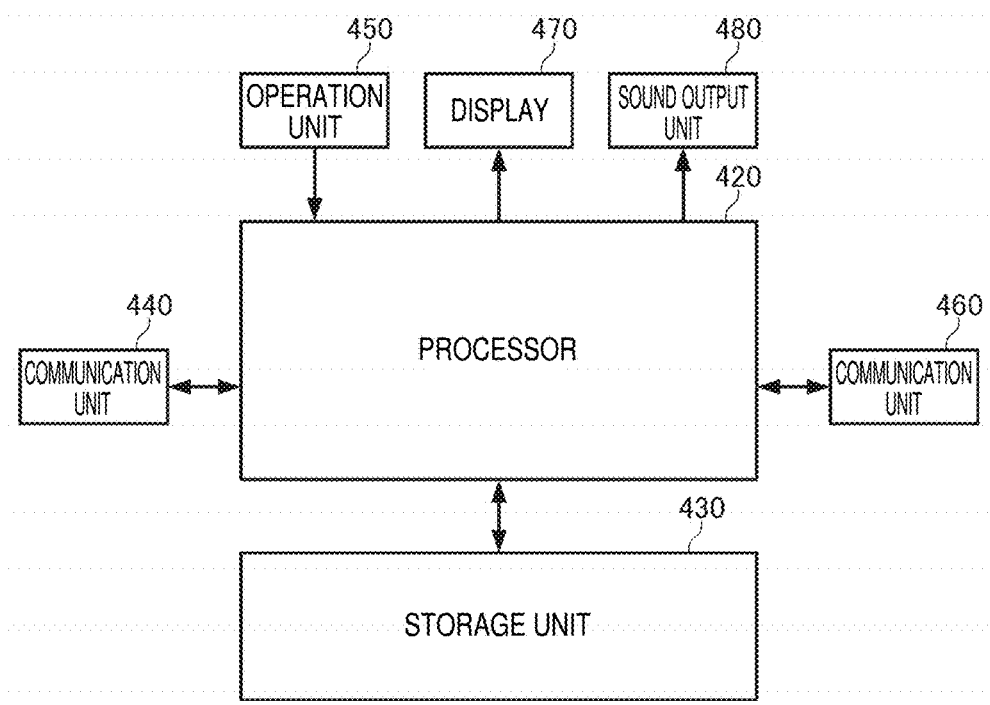
FIG. 11 is a functional block diagram illustrating a configuration example of an information analysis apparatus.

1-5. Information Analysis Apparatus 1-5-1. Configuration of Information Analysis Apparatus FIG. 11 is a functional block diagram illustrating a configuration example of the information analysis apparatus 4. As illustrated in FIG. 11, the information analysis apparatus 4 includes a processor 420, a storage unit 430, the communication unit 440, an operation unit 450, a communication unit 460, a display 470, and a sound output unit 480. However, the information analysis apparatus 4 of the present embodiment may have a configuration in which some of the constituent elements are deleted or changed, or other constituent elements may be added thereto.

The communication unit 440 performs data communication with the communication unit 40 (refer to FIG. 3) of the motion analysis apparatus 2 or the communication unit 140 (refer to FIG. 10) of the notification apparatus 3. The communication unit 440 performs a process of receiving a transmission request command for requesting transmission of motion analysis information 350 (motion analysis information included in running data to be registered) which is designated in response to operation data from the processor 420, transmitting the command to the communication unit 40 of the motion analysis apparatus 2, receiving the motion analysis information from the communication unit 40 of the motion analysis apparatus 2, and sending the motion analysis information to the processor 420.

The communication unit 460 performs data communication with the server 5, and performs a process of receiving running data to be registered from the processor 420 and transmitting the running data to the server 5 (a process of registering the running data), and a process of receiving management information corresponding to operation data such as editing, deleting, and changing of running data from the processor 420, and transmitting the management information to the server 5.

The operation unit 450 performs a process of acquiring operation data (operation data such as registration, editing, deleting, and changing of running data) from the user, and sending the operation data to the processor 420. The operation unit 450 may be, for example, a touch panel type display, a button, a key, and a microphone.

The display 470 displays image data or text data sent from the processor 420 by using text, a graph, a table, animation, and other images. The display 470 is implemented by a display such as an LCD, an organic EL display, and an EPD, and may be a touch panel type display. The functions of the operation unit 450 and the display 470 may be realized by a single touch panel type display.

The sound output unit 480 outputs sound data sent from the processor 420 as sounds such as voices or buzzer sounds. The sound output unit 480 is implemented by, for example, a speaker or a buzzer.

The storage unit 430 is constituted of, for example, recording media including a ROM, a flash ROM, a hard disk, and a memory card which store a program or data, and a RAM serving as a work area of the processor 420. The storage unit 430 (any one of recording media) stores an evaluation program which is read by the processor 420 and is used to perform a process related to evaluation.

The processor 420 is constituted of, for example, a CPU, a DSP, or an ASIC, and performs various calculation processes or control processes according to a program stored in the storage unit 430 (recording medium). For example, the processor 420 performs a process of transmitting a transmission request command for requesting transmission of motion analysis information 350 which is designated in response to operation data received from the operation unit 450, to the motion analysis apparatus 2 via the communication unit 440, and receiving the motion analysis information from the motion analysis apparatus 2 via the communication unit 440. For example, the processor 420 performs a process of generating running data including the motion analysis information received from the motion analysis apparatus 2 in response to operation data received from the operation unit 450, and transmitting the running data to the server 5 via the communication unit 460. The processor 420 performs a process of transmitting management information corresponding to operation data received from the operation unit 450, to the server 5 via the communication unit 460. The processor 420 performs a process of transmitting a transmission request of evaluation target running data which is selected in response to operation data received from the operation unit 450, to the server 5 via the communication unit 460, and receiving the evaluation target running data from the server 5 via the communication unit 460. The processor 420 performs a process of evaluating the evaluation target running data which is selected in response to operation data received from the operation unit 450 so as to generate evaluation information which is information regarding an evaluation result, and sending the evaluation information to the display 470 or the sound output unit 480 as text data, image data, or sound data.

Particularly, in the present embodiment, the processor 420 executes the evaluation program stored in the storage unit 430. However, the processor 420 may receive the evaluation program stored in any storage device (recording medium) via the network and may execute the evaluation program.

The processor 420 performs a process of acquiring motion performance information and physical performance information which are information regarding an analysis result of a motion of the analysis target user, from the database of the server 5 (or from the motion analysis apparatus 2). The motion performance information and the physical performance information acquired by the processor 420 are stored in the storage unit 430. The motion performance information and the physical performance information may be generated by the same motion analysis apparatus 2, and may be generated by any one of a plurality of different motion analysis apparatuses 2. A plurality of different pieces of motion performance information and physical performance information acquired by the processor 420 may include values of various motion indexes (for example, the above-described motion indexes) of the user.

The processor 420 evaluates motion performance of the user on the basis of the acquired motion performance information. The processor 420 evaluates physical performance of the user on the basis of the acquired physical performance information. The processor 420 may evaluate motion performance of the user on the basis of the motion performance information and the physical performance information. The processor 420 may evaluate physical performance of the user on the basis of the motion performance information and the physical performance information. A specific example of evaluation in the processor 420 will be described later.

The processor 420 generates display data such as text or an image or sound data such as voice by using the generated evaluation result, and outputs the display data or the sound data to the display 470 or the sound output unit 480. Consequently, the evaluation result of the evaluation target user is presented from the display 470 or the sound output unit 480.

1-6. Overview of Present Embodiment

In the present embodiment, the first analysis information 353 includes a first propulsion force, a second propulsion force, and a third propulsion force. Hereinafter, among operations of the motion analysis apparatus 2, an operation related to the first propulsion force, the second propulsion force, and the third propulsion force will be focused. Herein, a description will be made of an example of analyzing a user's running, but, similarly, walking may be analyzed.

The motion analysis apparatus 2 according to the present embodiment includes the processor 20 (an example of a motion analysis unit) which analyzes the input information 351 (example of motion information) in a user's running by using a detection result in the inertial measurement unit 10 (an example of an inertial sensor), and the communication unit 40 which outputs information regarding propulsion forces generated in the user's body within one cycle of motion related to walking or running, for each action of the user in a section on the basis of the input information 351. The processor 20 analyzes the input information 351 (for example, a temporal change in a propulsion force generated in the user's body) in the user's running by using the inertial measurement unit 10 (for example, the acceleration sensor 12 and the angular velocity sensor 14). The communication unit 40 outputs information regarding a propulsion force generated in the user's body within one cycle of motion related to walking or running, for example, information regarding a propulsion force generated in the user's body in a section (that is, a section corresponding to one step) from landing of walking or running to the next landing (from landing of one foot to landing of the other foot; for example, from landing of the right foot to landing of the left foot) to at least one of the notification apparatus 3 and the information analysis apparatus 4 for each action of the user (for example, for each of an action using at least one of an inertial force and the gravity, an action using rotation of at least a part of the body, and an action using muscle strength of the body) in the section, on the basis of the input information 351 (for example, a temporal change in the propulsion force generated in the user's body). Since a running form of the user is reflected in the information regarding each action in detail, the user (a running user or a manager thereof) analyzes the magnitude relationship among propulsion forces of the respective actions or a temporal change in the propulsion force of each action so as to easily find out a habit of the running form or to derive a measure for improvement of the form. As the information regarding a propulsion force generated in the user's body within one cycle of motion related to walking or running, information regarding a propulsion force generated in the user's body may be output not only within the section from landing of walking or running to the next landing, but also within a section from taking-off (a timing at which the foot leaves the ground) to the next taking-off, from a location where the user's position is highest (for example, a position where a location of the waist is farthest from the ground) to the next location where the user's position is highest, and from a location where the user's position is lowest (for example, a position where a location of the waist is closest to the ground) to the next location where the user's position is lowest.

1-7. Description of Propulsion Force

Figure 22:
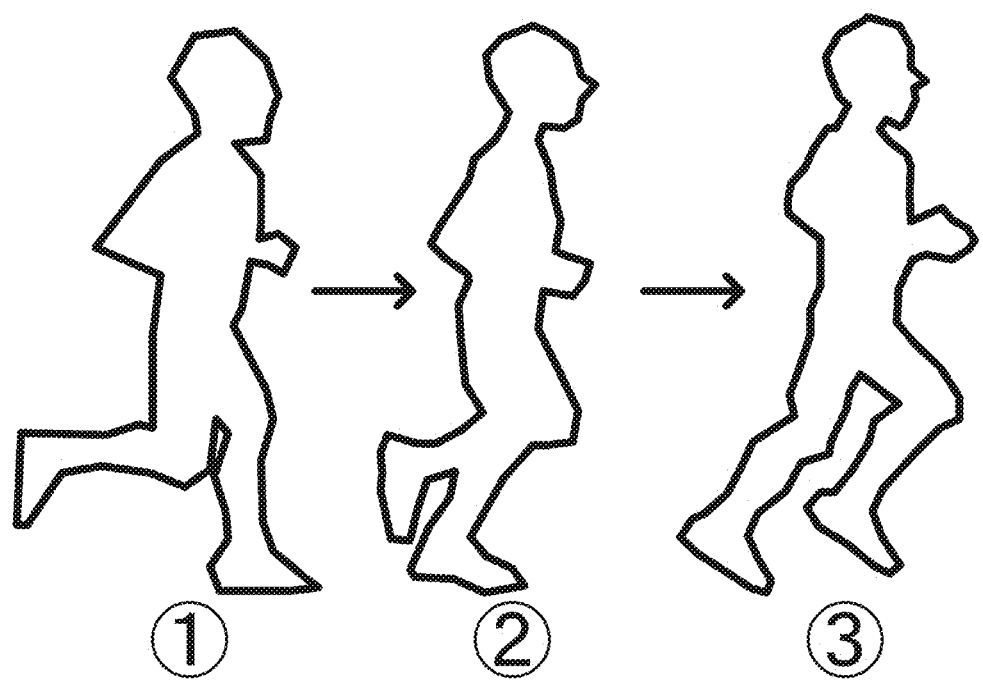
FIG. 22 is a diagram for explaining each action during the user's running.

In the motion analysis apparatus 2 according to the present embodiment, the user's actions include at least one of (i) an action using at least one of an inertial force and the gravity, (ii) an action using rotation of at least a part of the body, and (iii) an action using muscle strength of the body. According to the configuration, the user can recognize a propulsion force related to at least one of the actions (i), (ii) and (iii) separately from other propulsion forces. The "action using at least one of an inertial force and the gravity" is, for example, a brake action in landing ((1) of FIG. 22 which will be described later), the "action using rotation of at least a part of the body" is, for example, an action of returning the leg ((2) of FIG. 22 which will be described later), and the "action using muscle strength of the body" is, for example, an action of stretching the leg, for example, stretching the ankle ((3) of FIG. 22 which will be described later). In FIG. 22, circled numbers ((1), (2), (3), . . . ) are used instead of numbers in parentheses (this is also the same for other drawings). In the drawings, a circled number corresponds to a number in a parenthesis in the specification.

Therefore, the processor 20 of the present embodiment analyzes the input information 351 in the section from landing to the next landing during the user's running, so as to separately calculate the following three types of propulsion forces. Each of the following three types of propulsion forces is one kind of motion analysis information 350.

First Propulsion Force

Figure 12:
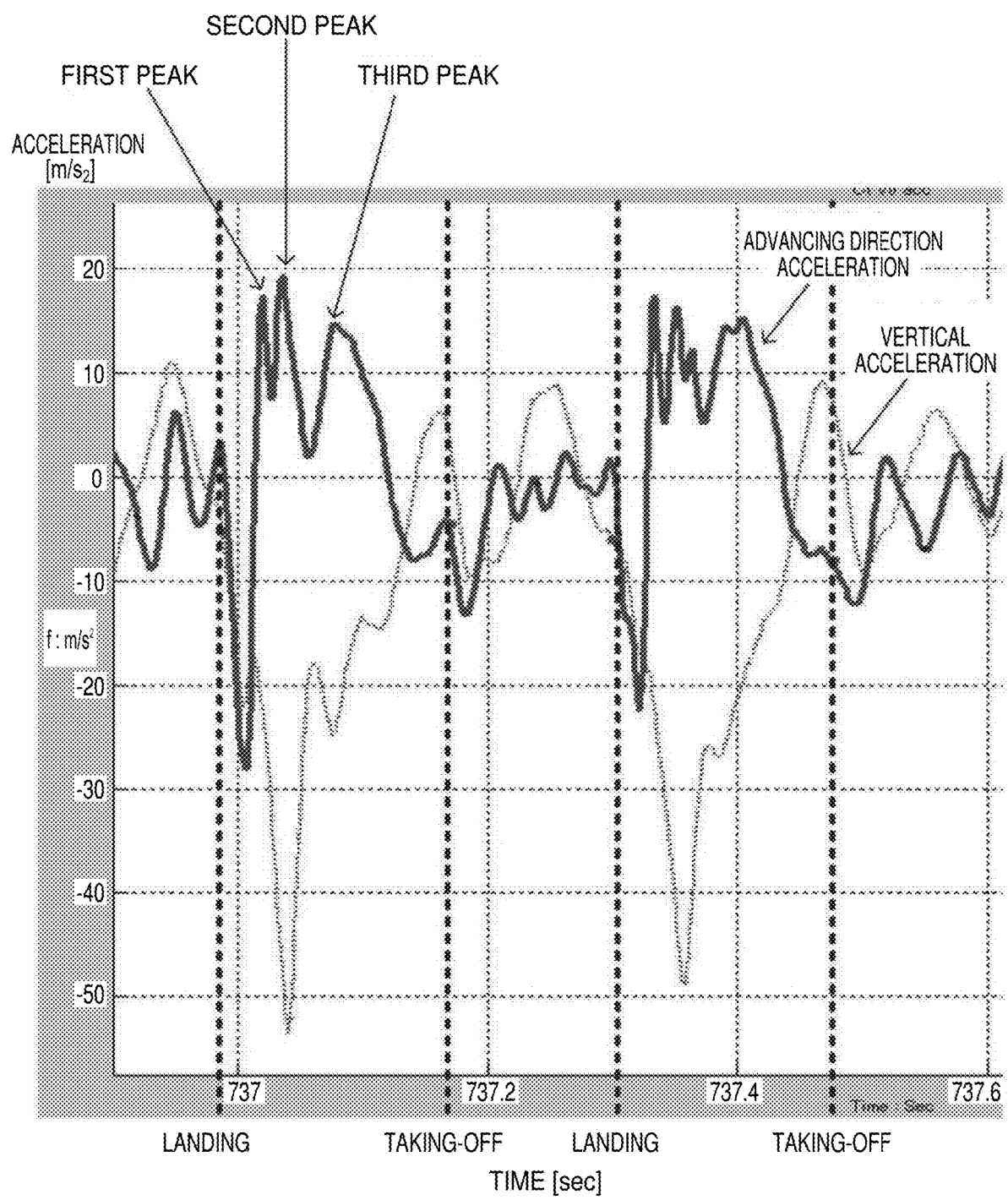
FIG. 12 is a diagram for explaining a first peak, a second peak, and a third peak, in which a transverse axis is a time axis, a longitudinal axis is an acceleration axis, and a temporal change curve of a vertical direction acceleration is displayed to overlap a temporal change curve of an advancing direction acceleration.

The first propulsion force is a propulsion force generated by the action (first action) using an inertial force and the gravity, and is, for example, a propulsion force using brake in landing ((1) of FIG. 22 which will be described later) as the first action. As illustrated in FIG. 12, the first propulsion force is expressed by the magnitude of a first peak (a height of the peak, an area of the peak, or the like) occurring in a temporal change curve of an advancing direction acceleration. A method of detecting the first peak will be described later.

Second Propulsion Force

The second propulsion force is a propulsion force generated by the action (second action) using rotation of at least a part of the body, and is, for example, a propulsion force using returning of the leg after landing ((2) of FIG. 22 which will be described later) as the second action. As illustrated in FIG. 12, the second propulsion force is expressed by the magnitude of a second peak (a height of the peak, an area of the peak, or the like) occurring in a temporal change curve of an advancing direction acceleration. A method of detecting the second peak will be described later.

Third Propulsion Force

The third propulsion force is a propulsion force generated by the action (third action) using muscle strength of the body, and is, for example, a propulsion force using stretching of the knee or stretching of the ankle ((3) of FIG. 22 which will be described later) as the third action. As illustrated in FIG. 12, the third propulsion force is expressed by the magnitude of a third peak (a height of the peak, an area of the peak, or the like) occurring in a temporal change curve of an advancing direction acceleration. A method of detecting the third peak will be described later.

1-8. Information of which User is Notified

In the motion analysis apparatus 2 according to the present embodiment, information output from the communication unit 40 includes information regarding a propulsion force caused by the right foot of the user and information regarding a propulsion force caused by the left foot of the user. According to the configuration, the user can separately recognize a propulsion force related to the left foot and a propulsion force related to the right foot. For example, the processor 20 of the present embodiment calculates a first propulsion force, a second propulsion force, and a third propulsion force related to the right foot of the user separately from a first propulsion force, a second propulsion force, and a third propulsion force related to the left foot of the user (refer to FIGS. 21 and 23 and the like which will be described later), and the communication unit 40 outputs the first propulsion force, the second propulsion force, and the third propulsion force related to the right foot of the user separately from the first propulsion force, the second propulsion force, and the third propulsion force related to the left foot of the user.

In the motion analysis apparatus 2 according to the present embodiment, the communication unit 40 outputs information regarding the brake within a section from landing to the next landing along with information regarding a propulsion force. According to the configuration, the user can recognize a propulsion force through comparison with the brake. For example, the processor 20 of the present embodiment separately calculates the first propulsion force, the second propulsion force, and the third propulsion force related to the right foot of the user, the first propulsion force, the second propulsion force, and the third propulsion force related to the left foot of the user, the brake of the right foot, and the brake of the left foot, and the communication unit 40 separately outputs the first propulsion force, the second propulsion force, and the third propulsion force related to the right foot of the user, the first propulsion force, the second propulsion force, and the third propulsion force related to the left foot of the user, the brake of the right foot, and the brake of the left foot. According to the configuration, the user can analyze the magnitude relationship between a propulsion force and the brake, or a temporal change in the magnitude relationship (refer to FIG. 26 or the like which will be described later).

1-9. First Peak Detection Process

Figure 13:
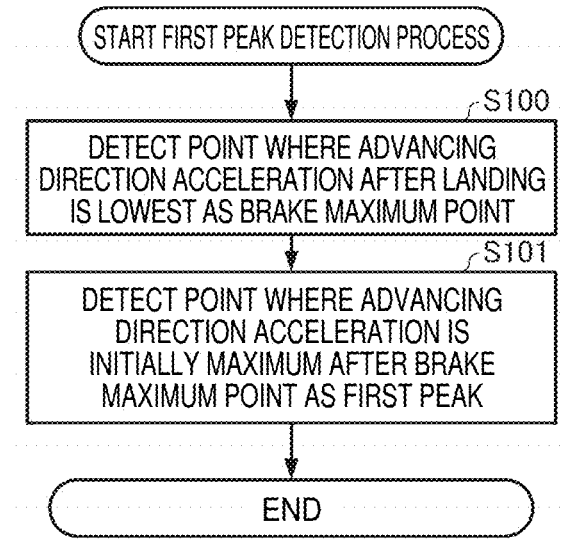
FIG. 13 is a flowchart illustrating a first peak detection process.

Hereinafter, a description will be made of a flow of a first peak detection process performed by the processor 20 with reference to FIG. 13.

First, the processor 20 refers to the section from landing to taking-off in the temporal change curve (FIG. 12) of the advancing direction acceleration, and detects a point where the advancing direction acceleration after the landing is lowest in the section as a brake maximum point (S100). A method of detecting a timing of landing and a timing of taking-off is as described above. The "temporal change curve" mentioned here is pieces of sensing data arranged in a time series (pieces of sensing data arranged in a sampling order) (the same applies hereinafter).

Next, the processor 20 detects, as the first peak, a point where the advancing direction acceleration is initially the maximum after the brake maximum point, and finishes the flow (S101).

The first peak detection process is performed, for example, on each of a section from landing of the right foot to taking-off thereof and a section from landing of the left foot to taking-off thereof. The first peak detection process is performed at each of the time when taking-off of the right foot is detected and the time when taking-off of the left foot is detected.

1-10. Second Peak Detection Process

Figure 14:
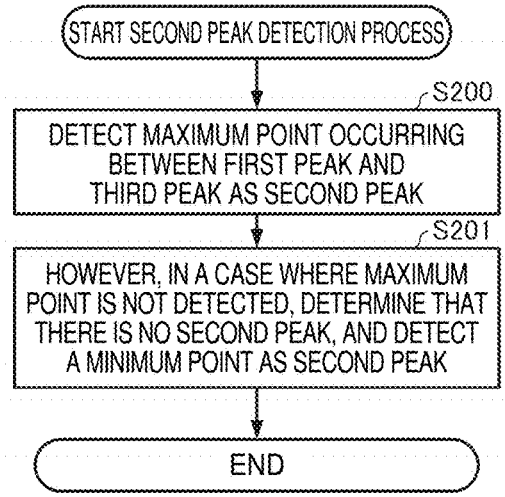
FIG. 14 is a flowchart illustrating a second peak detection process.

Hereinafter, a description will be made of a flow of a second peak detection process performed by the processor 20 with reference to FIG. 14.

First, the processor 20 detects, as the second peak, a maximum point occurring between the first peak and the third peak on the basis of the temporal change curve (FIG. 12) of the advancing direction acceleration (S200). A method of detecting the third peak will be described later.

However, in a case where a maximum point is not detected, the processor 20 determines that there is no second peak, and detects a minimum point as the second peak (S201).

The second peak detection process is performed, for example, on each of a section from landing of the right foot to taking-off thereof and a section from landing of the left foot to taking-off thereof. The second peak detection process is performed at each of the time when taking-off of the right foot is detected and the time when taking-off of the left foot is detected.

1-11. Third Peak Detection Process

Figure 15:
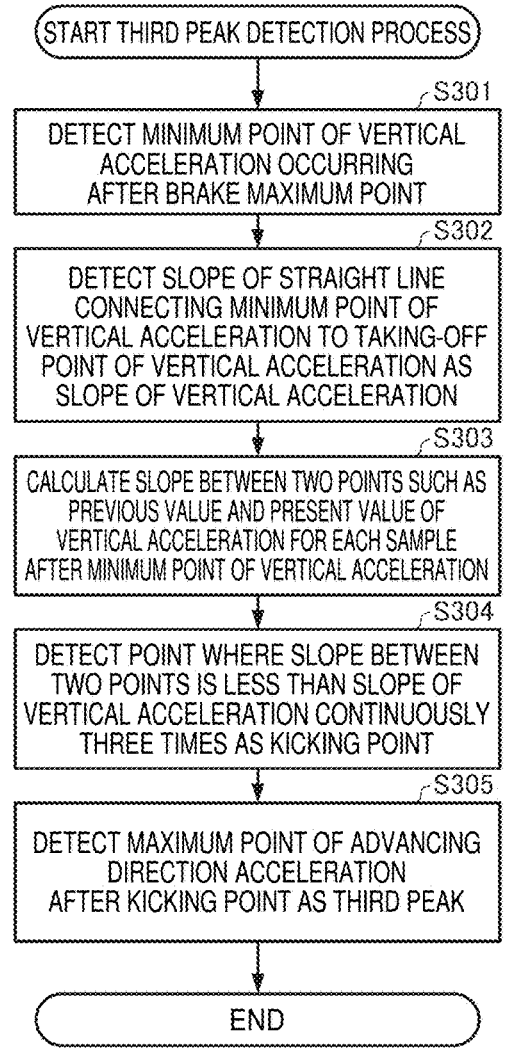
FIG. 15 is a flowchart illustrating a third peak detection process.
Figure 16:
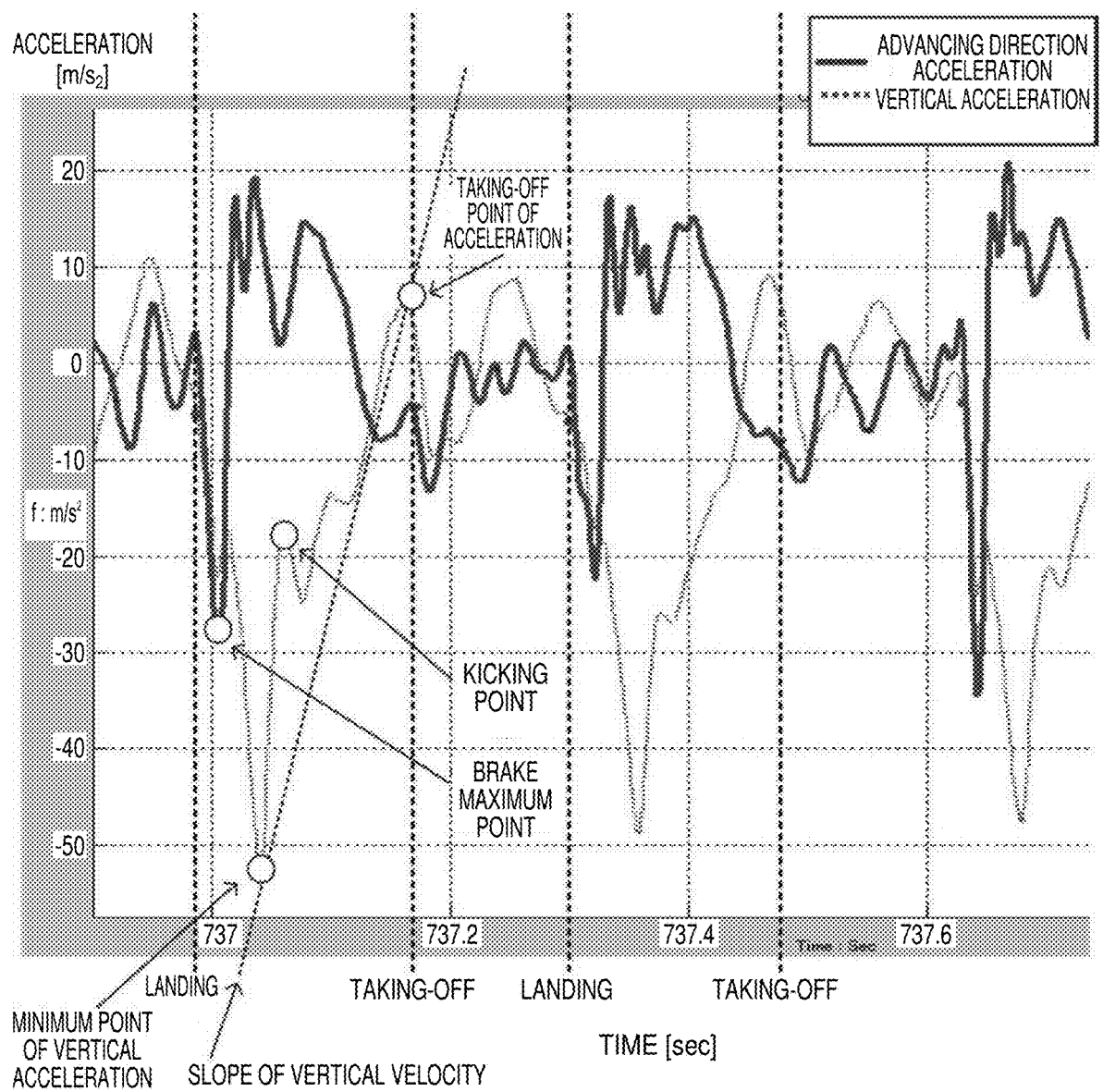
FIG. 16 is a diagram for explaining the third peak detection process, in which a transverse axis is a time axis, a longitudinal axis is an acceleration axis, and a temporal change curve of a vertical direction acceleration is displayed to overlap a temporal change curve of an advancing direction acceleration.

Hereinafter, a description will be made of a flow of a third peak detection process performed by the processor 20 with reference to FIGS. 15 and 16.

First, the processor 20 refers to a section from landing to taking-off in temporal change curves (FIG. 16) of an advancing direction acceleration and a vertical acceleration, and detects a minimum point of the vertical acceleration occurring after a brake maximum point in the section (S301).

Next, the processor 20 detects a slope of a straight line connecting the minimum point of the vertical acceleration to a taking-off point of the vertical acceleration as a slope of the vertical acceleration (S302).

Next, the processor 20 calculates a slope between two points such as the previous value and the present value of the vertical acceleration for each sample after the minimum point of the vertical acceleration (S303).

Next, the processor 20 detects a point where the slope between two points is less than the slope of the vertical acceleration continuously three times as a kicking point (S304).

Next, the processor 20 detects a maximum point of the advancing direction acceleration after the kicking point as the third peak (S305).

The third peak detection process is performed, for example, on each of a section from landing of the right foot to taking-off thereof and a section from landing of the left foot to taking-off thereof. The third peak detection process is performed at each of the time when taking-off of the right foot is detected and the time when taking-off of the left foot is detected.

1-12. Information Transmitted to and Received from System

As described above, the processor 20 of the motion analysis apparatus 2 calculates the first propulsion force, the second propulsion force, and the third propulsion force when landing of the right foot is detected during the user's running. The processor 20 calculates the first propulsion force, the second propulsion force, and the third propulsion force when landing of the left foot is detected during the user's running. The communication unit 40 of the motion analysis apparatus 2 sequentially transmits information (motion analysis information) regarding the calculated first propulsion force, second propulsion force, and third propulsion force, to the notification apparatus 3 and the information analysis apparatus 4.

On the other hand, the communication unit 140 of the notification apparatus 3 and the communication unit 440 of the information analysis apparatus 4 sequentially receive the motion analysis information 350 transmitted from the motion analysis apparatus 2 during the user's running. The processor 120 of the notification apparatus 3 sequentially notifies the user of the motion analysis information 350 (including the first propulsion force, the second propulsion force, and the third propulsion force) received by the communication unit 140 during the running, via at least one of the display 170 and the sound output unit 180.

The processor 420 of the information analysis apparatus 4 transmits running data (including changes in the first propulsion force, the second propulsion force, and the third propulsion force) including the motion analysis information 350 received by the communication unit 440 during the user's running, to the server 5 via the communication unit 460 at an appropriate timing after the running. Therefore, the running data (including changes in the first propulsion force, the second propulsion force, and the third propulsion force) of the user is accumulated in the server 5.

The information analysis apparatus 4 may sequentially notify the user of the motion analysis information 350 (including the first propulsion force, the second propulsion force, and the third propulsion force) received by the communication unit 440 from the motion analysis apparatus 2 during the running, via at least one of the display 470 and the sound output unit 480.

1-13. Propulsion Force Change Graph

Figure 17:
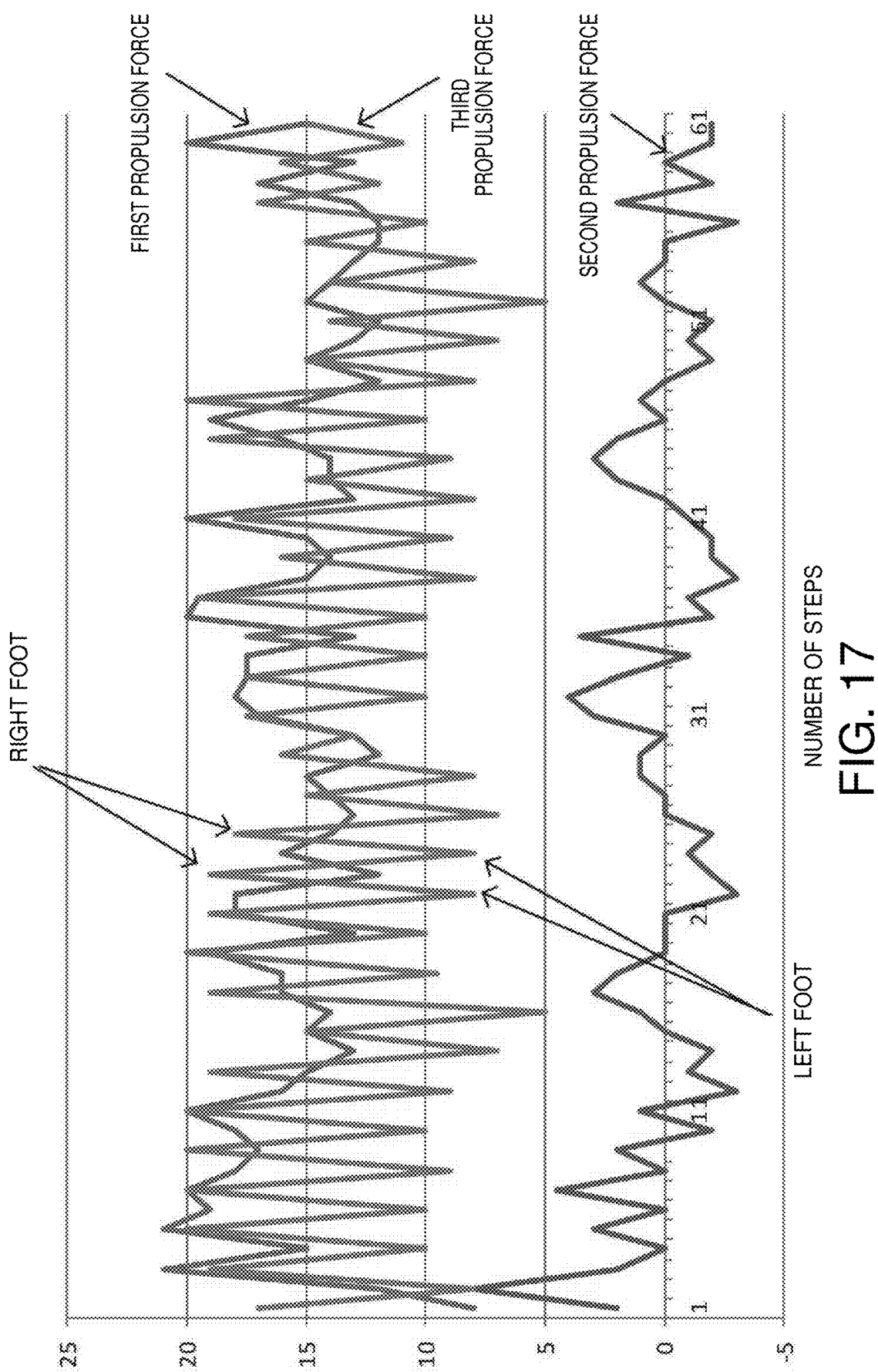
FIG. 17 is a diagram illustrating changes in a first propulsion force, a second propulsion force, and a third propulsion force, in which a transverse axis expresses the number of steps, a longitudinal axis expresses an acceleration (the magnitude of a peak), and data related to the right foot and data related to the left foot are alternately displayed.

FIG. 17 is a diagram illustrating changes in the first propulsion force, the second propulsion force, and the third propulsion force included in the running data. A transverse axis in FIG. 17 expresses the number of steps, and a longitudinal axis in FIG. 17 expresses an acceleration (corresponding to the magnitude of a peak). In FIG. 17, data related to the right foot and data related to the left foot are alternately displayed.

In the example illustrated in FIG. 17, (i) it can be seen that, since the second propulsion force is relatively weak, the user is poor at an action of obtaining a propulsion force due to returning of the leg after landing. (ii) Since the third propulsion force is relatively strong, it can be seen that the running is a run using a lot of muscle strength of the body. (iii) Since a left-and-right difference in the third propulsion force is great, it can be seen that a left-and-right balance in muscle strength for stretching the knee or the ankle is bad.

Therefore, the information analysis apparatus 4 of the present embodiment may evaluate (advise) in order to improve a running form of the user on the basis of the running data.

1-14. First Index

In the present embodiment, the processor 420 of the information analysis apparatus 4 calculates a first index for evaluating an action (first action) related to the first propulsion force, and uploads the first index to the server 5 as a kind of the running data.

Figure 18:
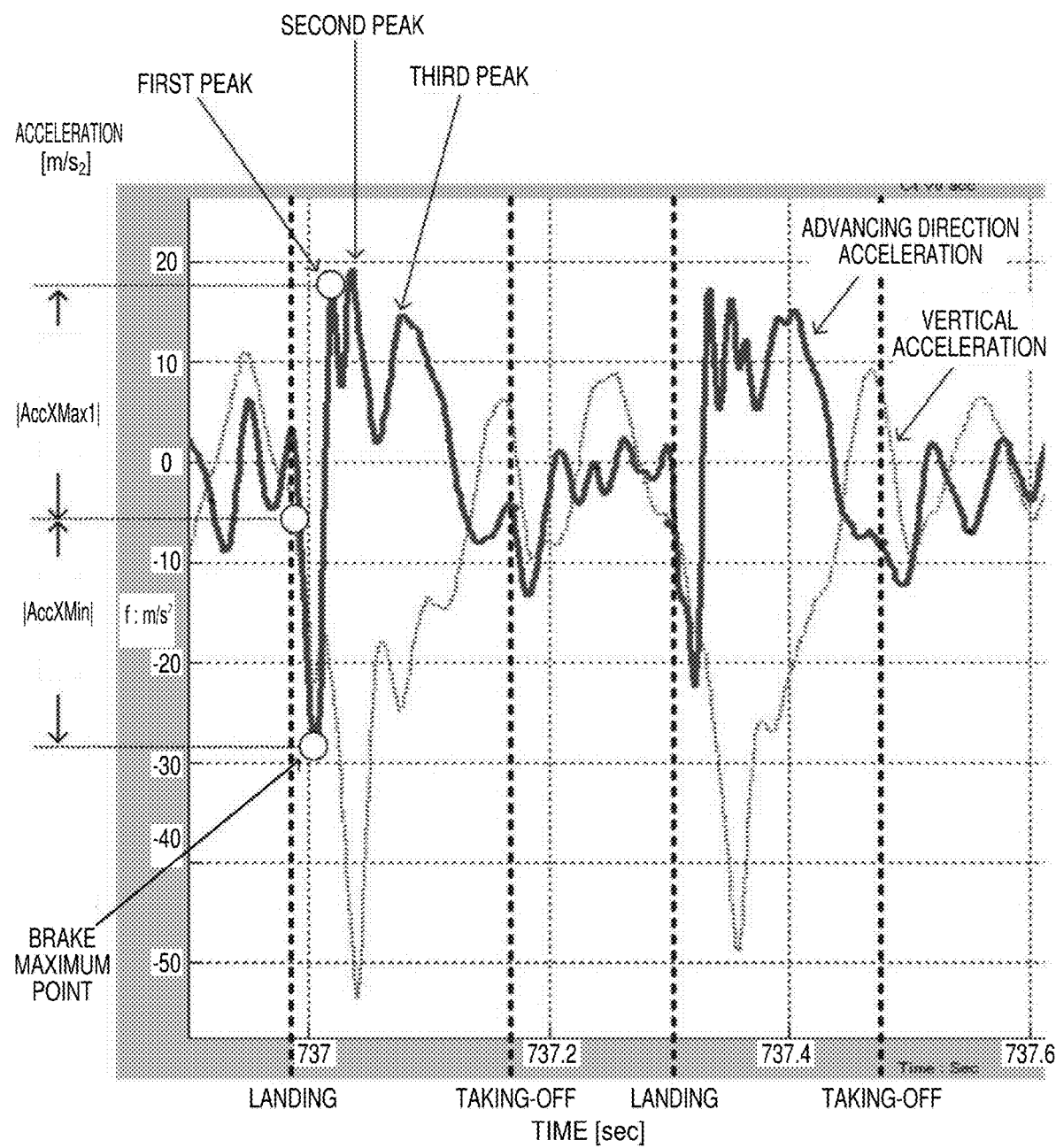
FIG. 18 is a diagram for explaining a first index, in which a transverse axis is a time axis, and a longitudinal axis is an acceleration axis.

FIG. 18 is a diagram for explaining the first index. The processor 20 calculates the first index (1st Index) according to the following equation.

$$\text{1st Index} = \text{Landing } Index_1 * \text{Landing } Index_2 \quad (7)$$
$$= \frac{AccX_{Max1}}{|AccX_{Min}|} * \frac{1}{1+|AccX_{Min}|}$$

In Equation (7), $AccX_{Min}$ indicates an advancing direction acceleration (deceleration amount) in a negative peak (brake maximum point) corresponding to the brake, and $AccX_{Max1}$ indicates a height of the first peak (a value of the advancing direction acceleration corresponding to the first peak). Values of $AccX_{Min}$ and $AccX_{Max1}$ may be obtained with, for example, a value of the advancing direction acceleration (in FIG. 18, a point indicated by a white dot mark) in landing as a reference. Alternatively, values of $AccX_{Min}$ and $AccX_{Max1}$ may be obtained with the advancing direction acceleration of zero as a reference. In a case where acceleration right after landing is greater than deceleration in the landing, the first index increases. In a case where deceleration in landing is small, the first index (1st Index) also increases.

Landing $Index_1$ in Equation (7) leads to Landing Index1>1 if the acceleration is greater than the brake, and leads to 0<Landing $Index_1$<1 if the acceleration is smaller than the brake. However, since the absolute magnitude of the denominator $AccX_{Min}$ of Landing $Index_1$ and the absolute magnitude of the numerator $AccX_{Max1}$ thereof are not reflected in the first index (1st Index), the first index (1st Index) have the same value in a case where $AccX_{Min}$=10 and $AccX_{Max1}$=10, and a case where $AccX_{Min}$=100, and $AccX_{Max1}$=100.

In Equation (7), Landing $Index_2$ leads to 0<Landing $Index_2$≤1. If $AccX_{Min}$ related to the brake is small, Landing $Index_2$ comes close to 1, and, if $AccX_{Min}$ is great, Landing $Index_2$ has a value infinitely close to 0.

It is possible to evaluate the quality of the first action of the user on the basis of the magnitude of the first index (1st Index). Specifically, if a value of the first index is great, it may be determined that the first action is favorable. The first index (1st Index) may be calculated for each step, may be calculated as an average value during running, and may be calculated for each of the left foot and the right foot.

1-15. Second Index

In the present embodiment, the processor 420 of the information analysis apparatus 4 calculates a second index for evaluating an action (second action) related to the second propulsion force, and uploads the second index to the server 5 as a kind of the running data.

Figure 19:
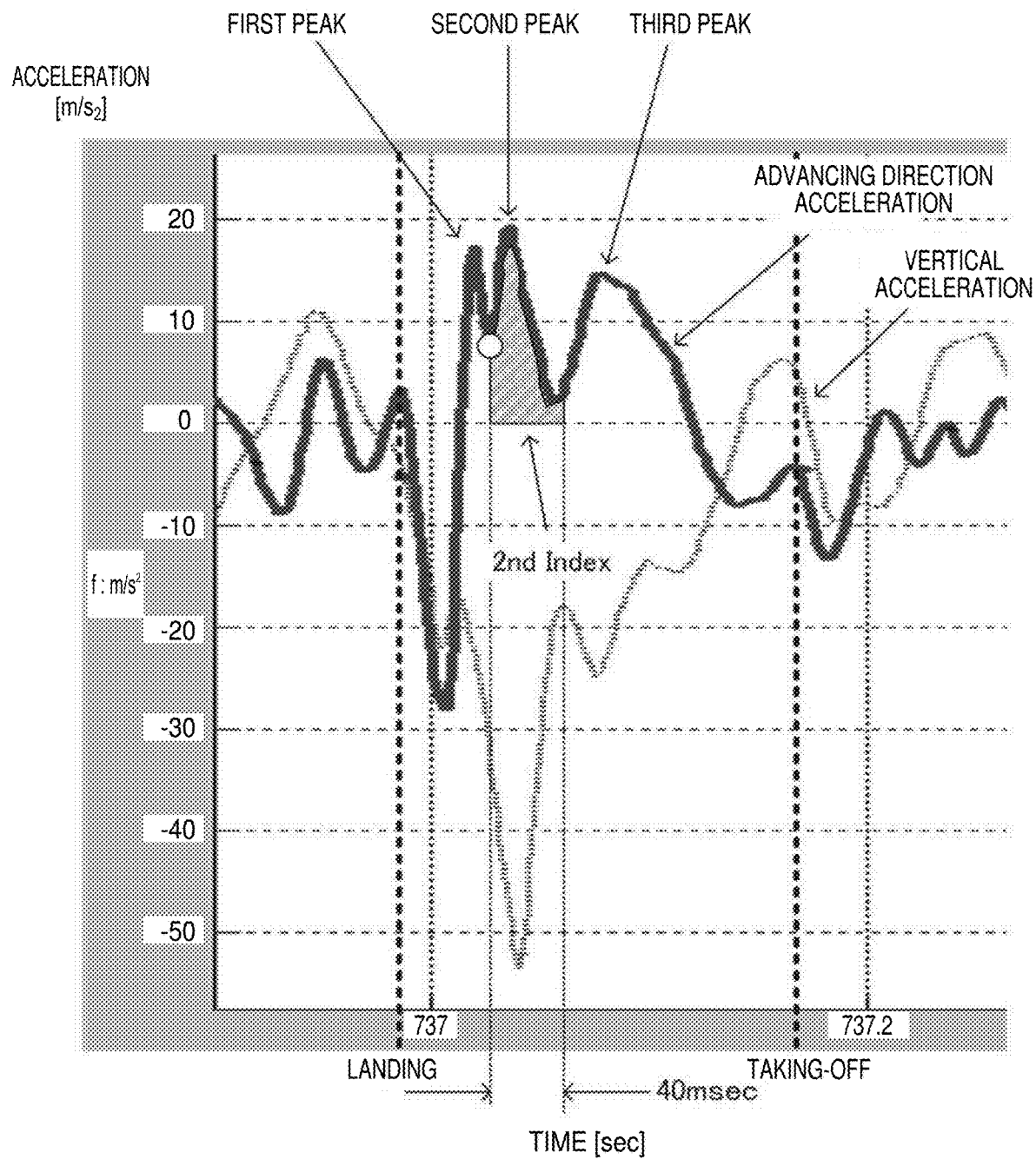
FIG. 19 is a diagram for explaining a second index, in which a transverse axis is a time axis, and a longitudinal axis is an acceleration axis.

FIG. 19 is a diagram for explaining the second index. The processor 20 calculates the second index (2nd Index) according to the following equation.

$$\text{2nd Index} = \int_{t_{Minimal}}^{t_{Minimal+20}} AccXdt \quad (8)$$

The second index (2nd Index) is obtained by integrating the advancing direction acceleration AccX over a predetermined period $t_{Minimal}$ to $t_{Minimal+20}$ after landing. The start time $t_{Minimal}$ of the integral period is, for example, a timing at which an advancing direction velocity (not illustrated) after landing is lowest. Alternatively, the start time $t_{Minimal}$ of the integral period is a minimum point (a white dot mark in FIG. 19) right after the first peak of the advancing direction acceleration. However, in a case where a minimum point right after the first peak cannot be detected, the time of mid-stance may be set as the start time $t_{Minimal}$. On the other hand, the end time $t_{Minimal+20}$ of the integral period is, for example, a timing after 40 ms (after twenty samples in a case where a sampling frequency is 500 Hz) from the start time $t_{Minimal}$ Of the integral period. The second index (2nd Index) corresponds to an area of a hatched region in FIG. 19 (however, in FIG. 19, a timing at which the advancing direction velocity (not illustrated) is lowest is set as the start time $t_{Minimal}$).

It is possible to evaluate the quality of the second action of the user on the basis of the magnitude of the second index. Specifically, if a value of the second index is great, it may be determined that the second action is favorable. The second index may be calculated for each step, may be calculated as an average value during running, and may be calculated for each of the left foot and the right foot.

1-16. Third Index

In the present embodiment, the processor 420 of the information analysis apparatus 4 calculates a third index for evaluating an action (third action) related to the third propulsion force, and uploads the third index to the server 5 as a kind of the running data.

Figure 20:
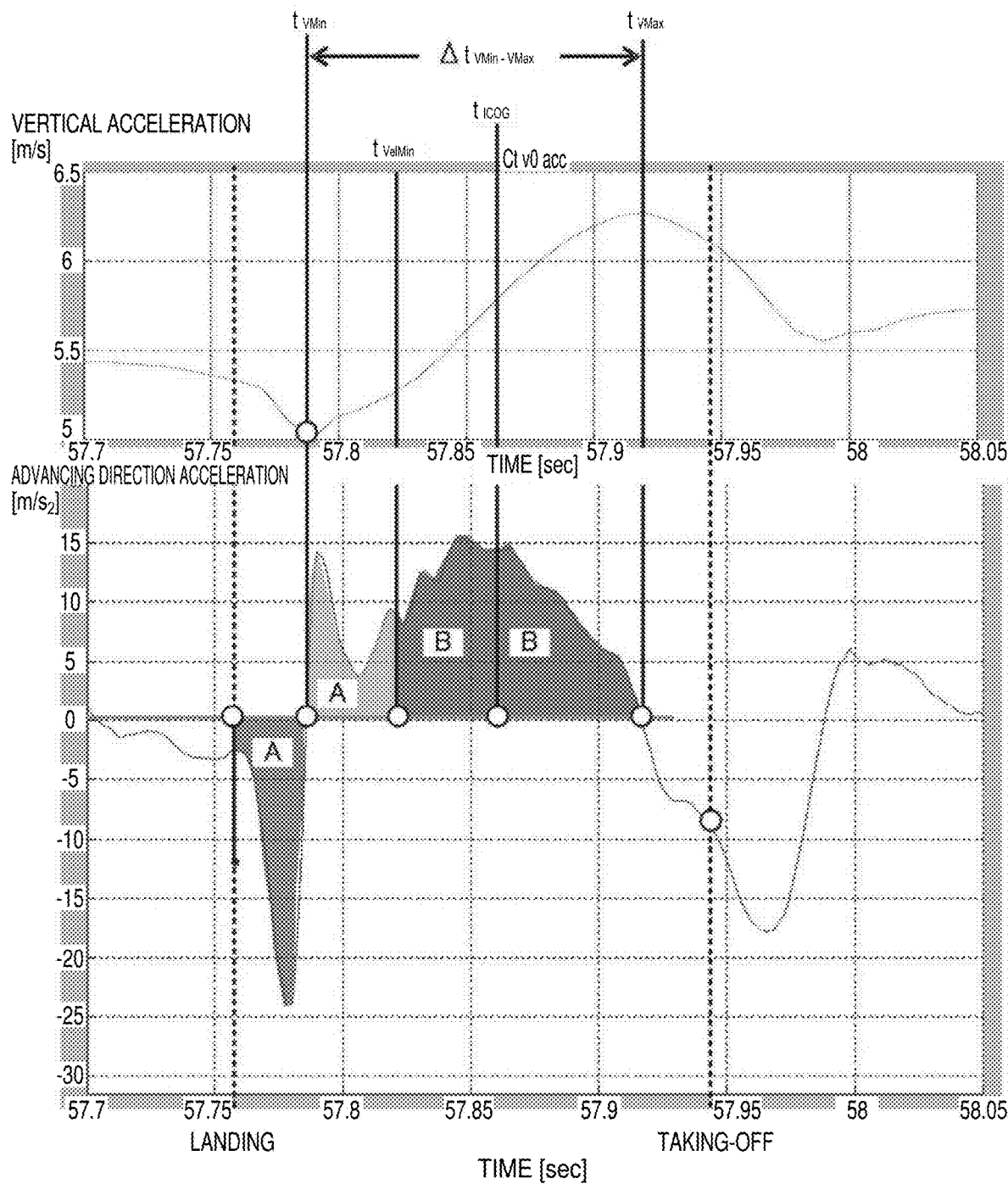
FIG. 20 is a diagram for explaining a third index, in which a lower part illustrates a temporal change curve of an advancing direction acceleration, an upper part illustrates a temporal change curve of a vertical direction acceleration, a transverse axis is a time axis, a longitudinal axis is an acceleration axis, and transverse axes of both of the curves are the same as each other.

FIG. 20 is a diagram for explaining the third index. The lower part in FIG. 20 illustrates a temporal change curve of the advancing direction acceleration, and the upper part in FIG. 20 illustrates a temporal change curve of the advancing direction velocity. Transverse axes (time axes) of both of the curves match each other.

The processor 20 calculates the third index (3rd Index) according to the following equation.

$$\text{3rd Index} = \frac{t_{ICOG} - t_{VMin}}{\Delta t_{VMin-VMax}} \quad (9)$$

Here, $t_{ICOG}$ in Equation (9) indicates a timing corresponding to the centroid of impulses 2B generated from a timing $t_{Velmin}$ at which a negative impulse A generated in landing is canceled out to a timing $t_{VMax}$ at which the advancing direction velocity is the maximum. Two areas indicated by the reference sign A in FIG. 20 are the same as each other, and indicate that the equivalent impulses are generated, and two areas indicated by the reference sign B in FIG. 20 are the same as each other, and indicate that the equivalent impulses are generated. The subscript "ICOG" of $t_{ICOG}$ stands for "impulse center of gravity".

It is possible to evaluate the quality of the third action of the user on the basis of the magnitude of the third index. Specifically, if a value of the third index is great, it may be determined that the third action is favorable. The third index may be calculated for each step, may be calculated as an average value during running, and may be calculated for each of the left foot and the right foot.

1-17. Display Screen of Notification Apparatus During Running

Figure 21:
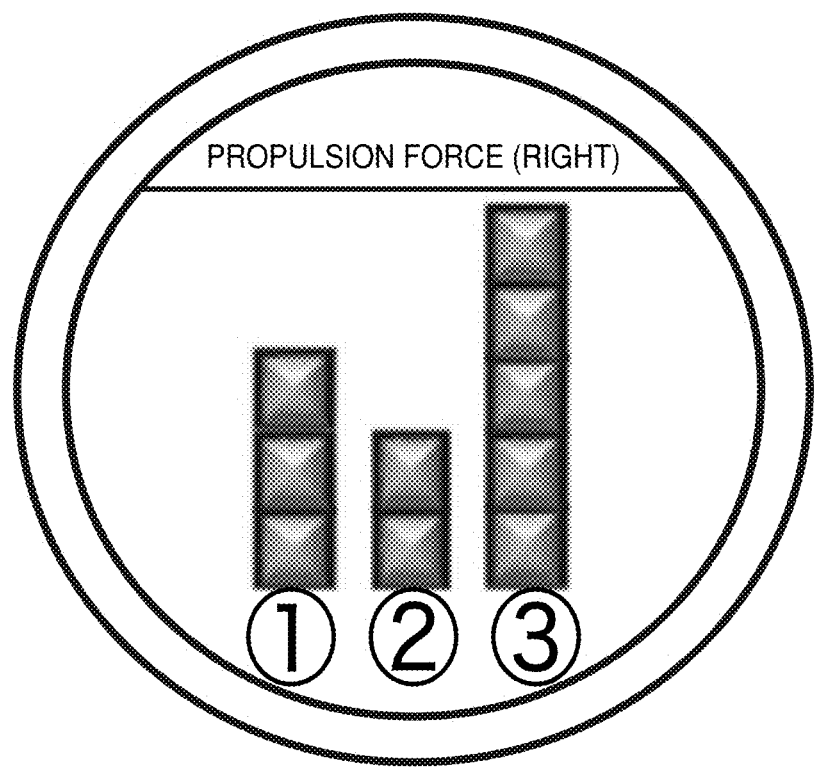
FIG. 21 is an example of a screen displayed on a display of the notification apparatus during the user's running.

FIG. 21 illustrates an example of a screen displayed on the display 170 of the notification apparatus 3 during the user's running. In FIG. 21, a case is assumed in which a contour of the display 170 of the notification apparatus 3 is circular. As illustrated in FIG. 21, for example, the first propulsion force ((1) of FIG. 21), the second propulsion force ((2) of FIG. 21), and the third propulsion force ((3) of FIG. 21) related to the right foot are displayed as bar graphs (block rows) on the display 170 of the notification apparatus 3. The blocks displayed on the left when viewed from the user indicate the first propulsion force, the blocks displayed at the center indicate the second propulsion force, and the blocks displayed on the right indicate the third propulsion force. The blocks of the first propulsion force, the blocks of the second propulsion force, and the blocks of the third propulsion force correspond to the generation order of the first action related to the first propulsion force, the second action related to the second propulsion force, and the third action related to the third propulsion force.

FIG. 22 is a diagram (an image representing silhouette of a human body) illustrating each action during the user's running. The first propulsion force ((1) in FIG. 21) is generated when the user's attitude is in a state illustrated in (1) of FIG. 22, the second propulsion force ((2) in FIG. 21) is generated when the user's attitude is in a state illustrated in (2) of FIG. 22, and the third propulsion force ((3) in FIG. 21) is generated when the user's attitude is in a state illustrated in (3) of FIG. 22. The notification apparatus 3 may display the image of silhouette as illustrated in FIG. 22 as an explanatory diagram of the first propulsion force, the second propulsion force, and the third propulsion force on the display 170. For example, the notification apparatus 3 may switch a display screen of the display 170 between the screen in FIG. 21 and the screen in FIG. 22. A screen switching timing is determined according to, for example, the user's predetermined operation or an elapsed time.

1-18. Display Screen of Information Analysis Apparatus During Running

Figure 23:
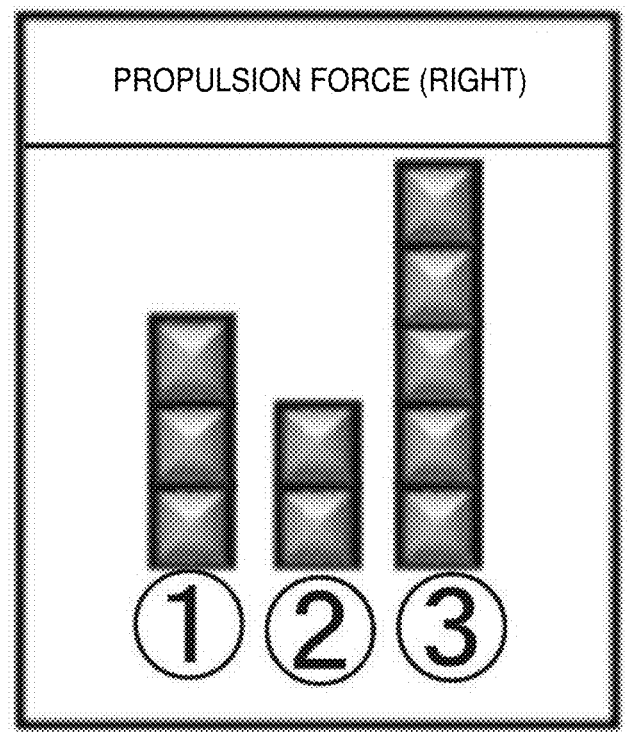
FIG. 23 is an example of a screen displayed on a display of the information analysis apparatus during the user's running.

FIG. 23 illustrates an example of a screen displayed on the display 470 of the information analysis apparatus 4 during the user's running. The screen illustrated in FIG. 23 is fundamentally the same as the screen (the screen of the notification apparatus 3) illustrated in FIG. 21, but a case is assumed in which a contour of the display 470 of the information analysis apparatus 4 is rectangular.

As illustrated in FIG. 23, for example, the first propulsion force ((1) of FIG. 23), the second propulsion force ((2) of FIG. 23), and the third propulsion force ((3) of FIG. 23) related to the right foot are displayed as bar graphs (block rows) on the display 470 of the information analysis apparatus 4. The blocks displayed on the left when viewed from the user indicate the first propulsion force, the blocks displayed at the center indicate the second propulsion force, and the blocks displayed on the right indicate the third propulsion force.

The information analysis apparatus 4 may display the image of silhouette as illustrated in FIG. 22 as an explanatory diagram of the first propulsion force, the second propulsion force, and the third propulsion force on the display 470. For example, the information analysis apparatus 4 may switch a display screen of the display 470 between the screen in FIG. 23 and the screen in FIG. 22. A screen switching timing is determined according to, for example, the user's predetermined operation or an elapsed time.

1-19. Voice Notification in Information Analysis Apparatus During Running

Figure 24:
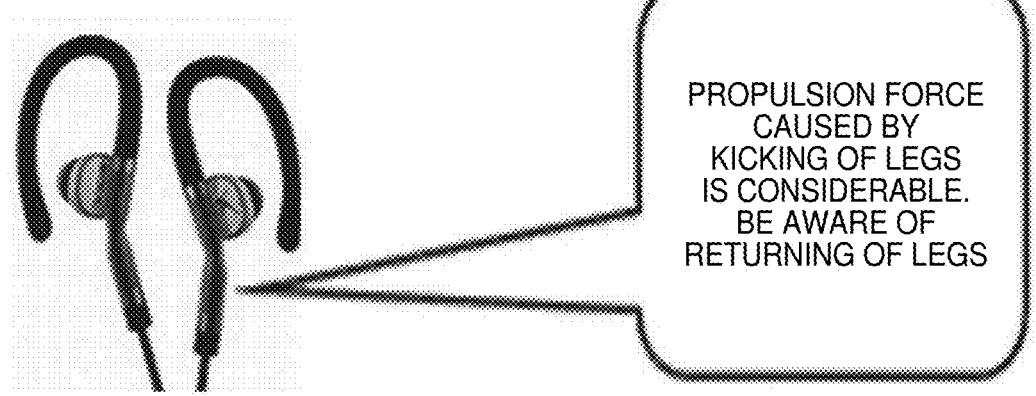
FIG. 24 illustrates an example of a voice output from a sound output unit during the user's running.

FIG. 24 illustrates an example of a voice output from the sound output unit 480 of the information analysis apparatus during the user's running. The processor 420 of the information analysis apparatus 4 performs evaluation (for example, calculation of the first index, the second index, and the third index described above) related to the first propulsion force, the second propulsion force, and the third propulsion force during the user's running. As illustrated in FIG. 24, the sound output unit 480 of the information analysis apparatus 4 may output voices indicating a result of the evaluation, for example, the content that "a propulsion force caused by kicking of the legs is considerable; and be aware of returning of the legs". Since it is hard for the user to view the screen of the information analysis apparatus 4 during running, the user is notified of the evaluation result in voices, and thus it is possible to suppress the influence on a running form due to checking. A process related to evaluation will be described later. FIG. 24 illustrates an image of a headphone which outputs voices to both ears of the user on the left part. The headphone is connected to the sound output unit 480 in a wireless or wired manner. Details of a process (type diagnosis) related to evaluation in the processor 420 will be described later (a relationship between the type of power ratio of the user and advice to the user is as illustrated in FIGS. 27 and 28).

1-20. Second Display Screen of Information Analysis Apparatus after Running

Figure 25:
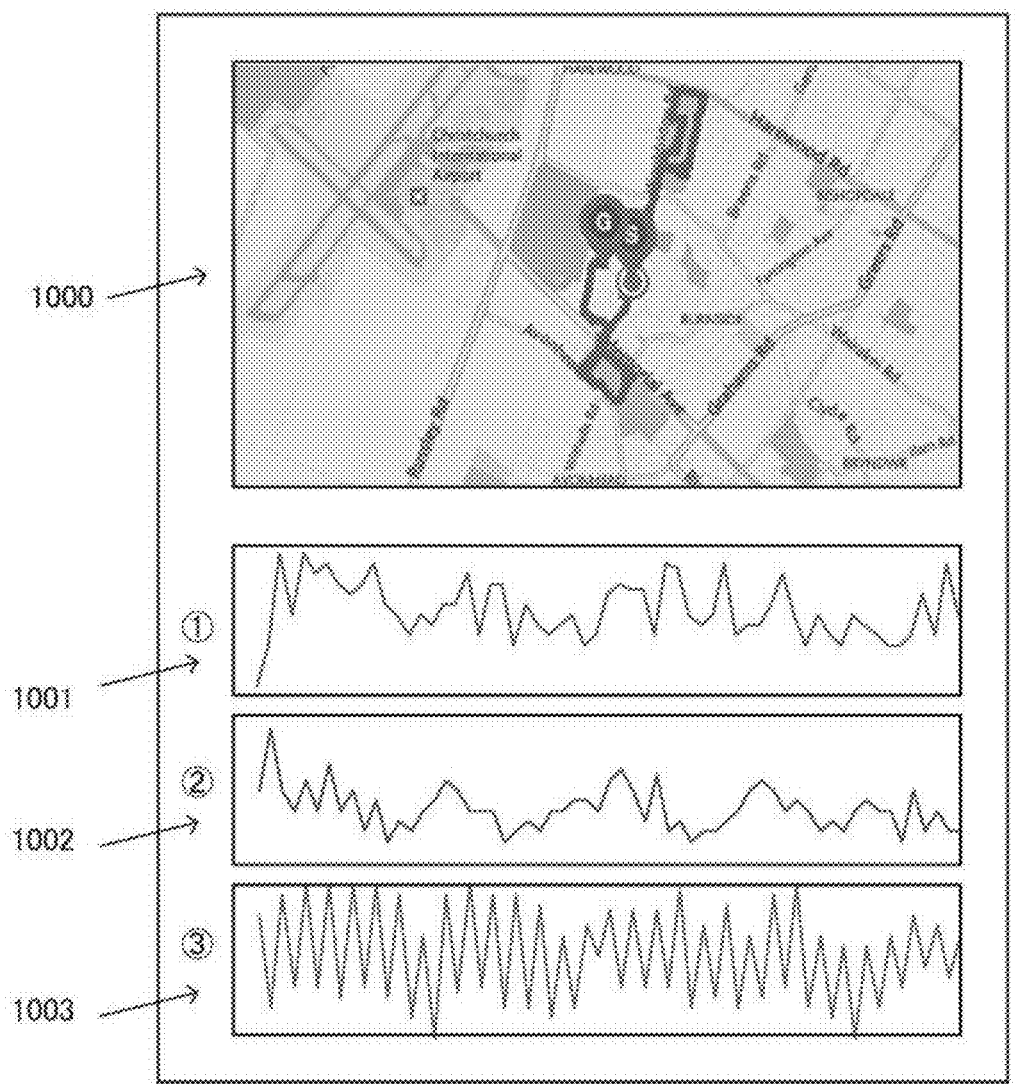
FIG. 25 is an example of a screen displayed on the display of the information analysis apparatus during the user's running.

FIG. 25 illustrates an example of a screen displayed on the display 470 of the information analysis apparatus 4 after the user's running. The screen is displayed on the basis of information received by the information analysis apparatus 4 from the motion analysis apparatus 2 during the user's running, or information downloaded by the information analysis apparatus 4 from the server 5 after the user's running.

As illustrated in FIG. 25, the display 470 of the information analysis apparatus 4 displays changes in the first propulsion force, the second propulsion force, and the third propulsion force included in the running data, for example, as graphs. The reference numeral 1001 in FIG. 25 indicates an example of a graph indicating a change in the first propulsion force, the reference numeral 1002 in FIG. 25 indicates an example of a graph indicating a change in the second propulsion force, and the reference numeral 1003 in FIG. 25 indicates an example of a graph indicating a change in the third propulsion force. In the example illustrated in FIG. 25, a map 1000 representing a route along which the user has traveled is displayed together with the graphs 1001, 1002 and 1003. The reference sign "G" in the map 1000 indicates an end point of the route along which the user has traveled, and the reference sign "S" indicates a start point of the route. The route along which the user has traveled is a path of a position of the user during running. A position of the user is calculated on the basis of the GPS data. The map in FIG. 25 is a map of an area including the route along which the user has traveled, and is downloaded to the information analysis apparatus 4 along with the running data from the world map preserved in the server 5 in advance.

1-21. Display Screen of Information Analysis Apparatus after Running

Figure 26:
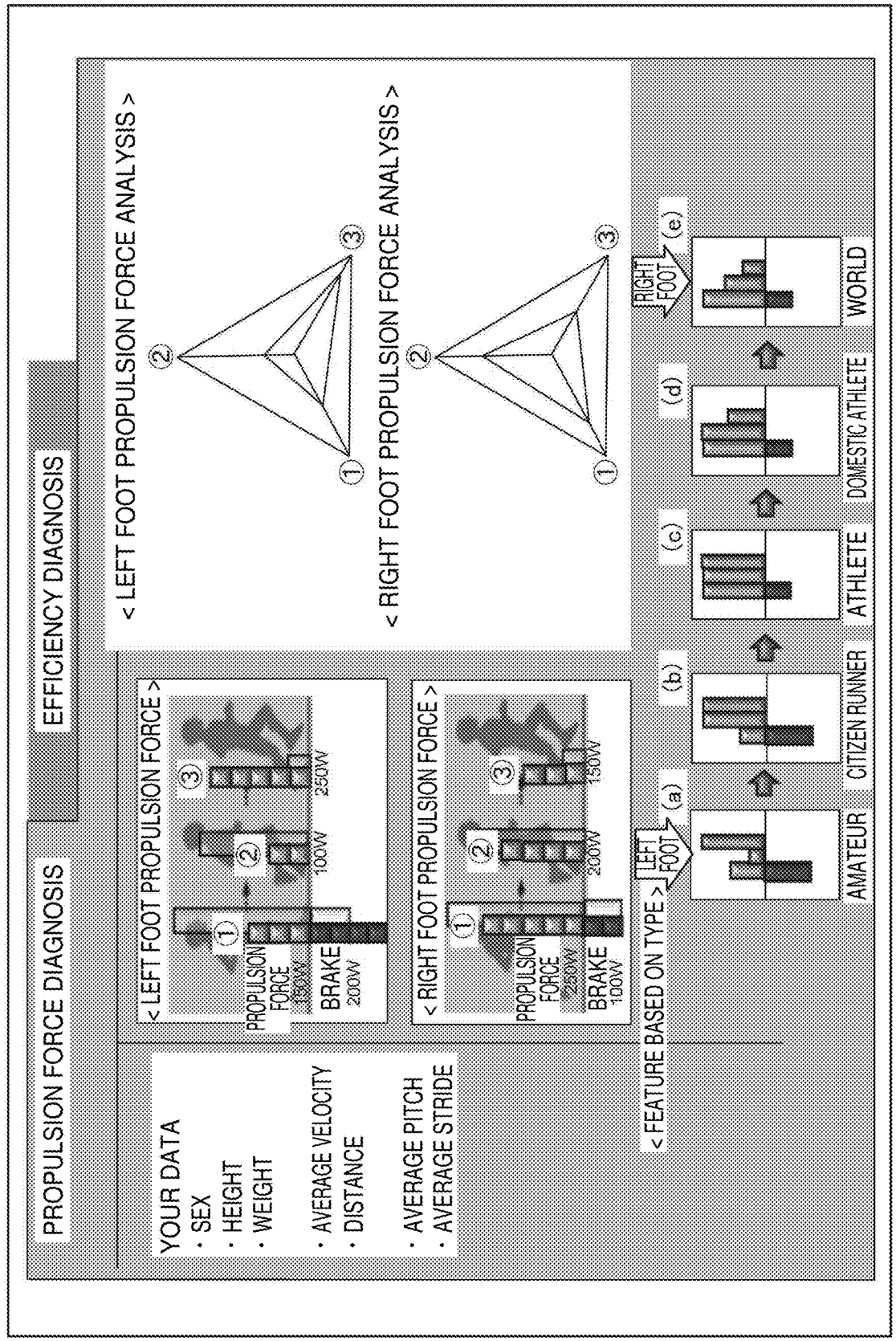
FIG. 26 is another example of a screen displayed on the display of the information analysis apparatus during the user's running.

FIG. 26 illustrates another example of a screen displayed on the display 470 of the information analysis apparatus 4 after the user's running. The screen is displayed on the basis of information received by the information analysis apparatus 4 from the motion analysis apparatus 2 during the user's running, or information downloaded by the information analysis apparatus 4 from the server 5 after the user's running.

The display 470 of the information analysis apparatus 4 displays a propulsion force diagnosis screen as illustrated in FIG. 26. The following items (i) to (vi) are displayed on the propulsion force diagnosis screen in FIG. 26. However, a layout of each of the items (i) to (vi) is not limited to the example illustrated in FIG. 26, and display of at least one of the items (i) to (vi) may be omitted. Hereinafter, the items (i) to (vi) will be described.

(i) User Data Item (Left Part in the Figure):

The user data item includes the user's sex, height, weight, average velocity, distance, average pitch, and average stride. Among the pieces of user data, data (the sex, the height, and the weight) which cannot be automatically input by the system is manually input by the user via the operation unit 450 of the information analysis apparatus 4.

(ii) Left Foot Propulsion Force Item (Upper Center in the Figure)

The first propulsion force, the second propulsion force, and the third propulsion force related to the left foot are displayed as bar graphs (block rows). However, blocks indicating brake amounts are also displayed along with the graphs. A timing at which the brake occurs is right before a timing at which the first propulsion force is generated, and thus the block indicating the brake amount is disposed in the same line as that of the block indicating the first propulsion force ((1) of FIG. 26). However, the brake corresponds to a negative propulsion force, and is thus expressed as a block extending toward an opposite side to the block of the first propulsion force.

(iii) Right Foot Propulsion Force Item (Intermediate Center in the Figure)

The first propulsion force, the second propulsion force, and the third propulsion force related to the right foot are displayed as bar graphs (block rows). However, blocks indicating brake amounts are also displayed along with the graphs. A timing at which the brake occurs is right before a timing at which the first propulsion force is generated, and thus the block indicating the brake amount is disposed in the same line as that of the block indicating the first propulsion force ((1) of FIG. 26). However, the brake corresponds to a negative propulsion force, and is thus expressed as a block extending toward an opposite side to the block of the first propulsion force.

(iv) Radar Chart of Left Foot Propulsion Force (Upper Right Part in the Figure)

The radar chart of a left foot propulsion force is a radar chart indicating a balance among the first index, the second index, and the third index related to the left foot. A first axis of the radar chart is an axis expressing an average value of the first index of the left foot during running, a second axis of the radar chart is an axis expressing an average value of the second index of the left foot during running, and a third axis of the radar chart is an axis expressing an average value of the third index of the left foot during running (however, it is assumed that the third index becomes larger as the third index comes closer to the origin of the third axis). As a triangle connecting values of the respective axes of the radar chart comes closer to an equilateral triangle, this indicates that a balance among the respective actions (the first action related to the first propulsion force, the second action related to the second propulsion force, and the third action related to the third propulsion force) of the left foot contributing to a propulsion force becomes better, and, a larger area of the triangle indicates a higher propulsion force of the left foot.

(v) Radar Chart of Right Foot Propulsion Force (Intermediate Right Part in the Figure)

The radar chart of a left foot propulsion force is a radar chart indicating a balance among the first index, the second index, and the third index related to the right foot. A first axis of the radar chart is an axis expressing an average value of the first index of the right foot during running, a second axis of the radar chart is an axis expressing an average value of the second index of the right foot during running, and a third axis of the radar chart is an axis expressing an average value of the third index of the right foot during running (however, it is assumed that the third index becomes larger as the third index comes closer to the origin of the third axis).

As a triangle connecting values of the respective axes of the radar chart comes closer to an equilateral triangle, this indicates that a balance of each action (the first action related to the first propulsion force, the second action related to the second propulsion force, and the third action related to the third propulsion force) of the right foot contributing to a propulsion force becomes better, and, a larger area of the triangle indicates a higher propulsion force of the right foot.

(vi) Item (Lower Part in the Figure) of Type Diagnosis Result of Left Foot and Right Foot This item indicates the type of right foot related to a propulsion force and the type of left foot related to a propulsion force. Herein, the item indicates the type to which a balance (hereinafter, referred to as a "power ratio") among four items such as the first propulsion force, the second propulsion force, the third propulsion force, and a brake amount of the user belongs. Here, the type of power ratio includes five types such as (a) an "amateur" type, (b) a "citizen runner" type, (c) an "athlete" type, (d) a "domestic athlete", and (e) a "world athlete" type. An operator or a manufacturer of the system of the present embodiment calculates (a) an average power ratio of amateurs, (b) an average power ratio of citizen runners, (c) an average power ratio of an athlete group, (d) an average power ratio of domestic athletes, and (e) an average power ratio of a world athlete group in advance on the basis of statistical data, and stores the values in the storage unit 430 of the information analysis apparatus 4 in advance. The processor 420 of the information analysis apparatus 4 calculates correlations among the first propulsion force, the second propulsion force, the third propulsion force, and the brake amount included in the running data of the user, and the five power ratios stored in the storage unit 430, and diagnoses a type corresponding to a power ratio having the highest correlation as the type of power ratio of the user. The example illustrated in FIG. 26 shows a case where a power ratio of the left foot of the user belongs to (a) the "amateur" type, and a power ratio of the right foot of the user belongs to (e) the "world athlete" type. In the example illustrated in FIG. 26, (a) since the "amateur" type, (b) the "citizen runner" type, (c) the "athlete" type, (d) the "domestic athlete", and (e) the "world athlete" type are arranged in this order from the left in FIG. 26, an arrow mark located further toward the right part on the screen indicates that a running form of the user becomes more excellent.

1-22. Advice Screen

FIGS. 27 and 28 illustrate other examples (examples of evaluation results) of screens displayed on the display 470 of the information analysis apparatus 4 after the user's running. FIGS. 27 and 28 illustrate examples in which advice is displayed as an evaluation result. In the examples illustrated in FIGS. 27 and 28, five advices corresponding to the five types are all displayed, but only advice related to any one of the types corresponding to the user may be displayed.

In FIGS. 27 and 28, for example, the following advices related to the five types are displayed. In FIGS. 27 and 28, a bar graph (block rows) of a power ratio corresponding to each type is displayed as an icon indicating each type.

(a) Advice Related to "Amateur" Type:

"You ran in the way of slow turnover of the legs". "The way is a running type causing the legs to be tired in the second half of marathon". "Let's perform exercise not causing slow turnover of the legs". "Exercise such as scissors or marching is the best".

(b) Advice Related to "Citizen Runner" Type

"In your run type, the brake is considerable, and a propulsion force cannot be obtained due to the brake". "There is a probability of overstride". "Note injuries of the waist, the knees, the thighs, and the like". "Perform exercise of being aware of directly-below landing in order to improve overstride". "Exercise such as bounding is the best".

(c) Advice Related to "Athlete" Type:

"In your run type, a propulsion force due to kicking of the legs is considerable." "Perform exercise of using the ankles in a fixed state assuming that the legs are rods". "You will be able to be conscious of a propulsion force by checking the propulsion force due to kicking of the legs in real time during running".

(d) Advice Related to "Domestic Athlete" Type:

"You have a propulsion force of a development agency level. An efficient propulsion force is obtained". "Try to further improve a propulsion force due to the brake".

(e) Advice Related to "World Athlete" Type:

"You have a propulsion force of a world level. A quite efficient propulsion force is obtained". "Perform exercise such that the same power ratio is obtained even if the speed is increased".

1-23. Application Examples of System

The user can perform exercise while checking an index of which the notification apparatus 3 or the information analysis apparatus 4 notifies the user during running. Feedback can be performed by setting a target value. For example, the user may input a target type in the notification apparatus 3 or the information analysis apparatus 4, and the notification apparatus 3 or the information analysis apparatus 4 may notify the user of whether or not the user's running corresponds to the target type during running.

After running, the user activates an application of the information analysis apparatus 4, downloads and checks running data (or information regarding the running data) of the user uploaded to the server 5, and can thus recognize a weak point of the user. Consequently, the user can set the next target value.

After running, the user can upload running data (the first propulsion force, the second propulsion force, the third propulsion force, the first index, the second index, the third index, and the like) of the user to the server 5, and can thus share the running data (the first propulsion force, the second propulsion force, the third propulsion force, the first index, the second index, the third index, and the like) with other people by using a social network service (SNS). For example, the user may share the running data index values (the first propulsion force, the second propulsion force, the third propulsion force, the first index, the second index, the third index, and the like) with an online coach, and may be provided with an optimal exercise menu from the online coach. The online coach may be a real person, and may be a computer of any server (virtual person) connected to a network.

2. Advantageous Effects of Embodiment

In the related art, it is considered that running forms are diversified, and analysis of a form unified into runners with different body types, races, and levels is difficult. However, in the system of the present embodiment, since a propulsion force is analyzed in detail and visualized with meaning, an action lacking in running of a user becomes clear, and thus anyone can clarify problem points. Specifically, in the system of the present embodiment, a propulsion force in one step which is important to improve running velocity is analyzed for each action, the presence or absence, the magnitude, and a temporal change of each propulsion force are visualized (or made audible), and thus a problem in any action is clarified. By clarifying the problem, an exercise method is clarified, and furthermore it is possible to understand whether or not the exercise exhibits the effect by repeating the same analysis, and thus it becomes possible to get proficiency efficiently. In other words, features and problems of running of a user are visualized in detail such that improvement points of the running become clear, and thus it is possible to perform high quality exercise efficiently. Effects of the exercise are visualized, and this leads to improvement in motivation.

3. Modification Examples

The invention is not limited to the embodiment, and may be variously modified within the scope of the invention. Hereinafter, modification examples will be described. The same constituent elements as those in the respective embodiments are given the same reference numerals, and repeated description will be omitted.

3-1. Unit of Propulsion Force

In the embodiment, "acceleration" is used as the unit expressing a propulsion force, but force (obtained by multiplying mass by acceleration), power (corresponding to an inner vector between a force vector and a velocity vector), work, or a combination of two or more thereof may be used.

In the embodiment, a propulsion force in an advancing direction may be used, but a propulsion force in a front-and-rear direction, a leftward-and-rightward direction, an upward-and-downward direction, or a combination of two or more thereof may be used.

3-2. Methods of Calculating Propulsion Force

In the embodiment, a timing (landing or taking-off) is detected on the basis of features of a motion action (running), and various propulsion forces are calculated by using the timing. In the embodiment, a feature or a time of a motion action (running) is divided into sections, and a peak, an integrated value, an average value, or the like in each of the sections may be calculated as a propulsion force having the influence on the section. A propulsion force may be estimated on the basis of a pattern of a temporal change (waveform) in sensing data. In the embodiment, relative values may be used as the first propulsion force, the second propulsion force, and the third propulsion force may be used instead of absolute values. It may be determined that there is a problem in an action related to a corresponding propulsion force by determining the presence or absence, the magnitude, and a temporal change of each propulsion force.

3-3. Distance Section Display of Running Route

In the motion analysis apparatus 2 according to the present embodiment, the communication unit 40 may output information regarding a propulsion force at each predetermined distance in a movement path of a user. According to the configuration, the user can recognize a propulsion force at each distance, and can thus compare, for example, propulsion forces between a first half and a second half of a movement path, or analyze a relationship between a movement distance and a propulsion force. For example, the processor 20 of the motion analysis apparatus 2 may calculate an average value of the first propulsion force, an average value of the second propulsion force, and an average value of the third propulsion force in each section obtained by dividing a running route with an equal distance, and the communication unit 40 may output the average values in each section to the notification apparatus 3. The display 170 of the notification apparatus 3 may display the received average values in each section.

For example, the processor 420 of the information analysis apparatus 4 may calculate an average value of the first propulsion force, an average value of the second propulsion force, and an average value of the third propulsion force in each section obtained by dividing a running route with an equal distance, and the communication unit 460 may transmit the average values in each section to the server 5 as a kind of running data. The communication unit 460 of the information analysis apparatus 4 may receive the running data from the server 5, and the display 470 of the information analysis apparatus 4 may display the average values in each section included in the received running data.

3-4. Time Section Display of Running Route

In the motion analysis apparatus 2 according to the present embodiment, the communication unit 40 may output information regarding a propulsion force for each time within a movement period of a user. According to the configuration, the user can recognize a propulsion force for each time, and can thus compare, for example, propulsion forces between a first half and a second half of a movement period, or analyze a relationship between a movement time and a propulsion force. For example, the processor 20 of the motion analysis apparatus 2 may calculate an average value of the first propulsion force, an average value of the second propulsion force, and an average value of the third propulsion force in each section obtained by dividing a running route with an equal time, and the communication unit 40 may output the average values in each section to the notification apparatus 3. The display 170 of the notification apparatus 3 may display the received average values in each section.

For example, the processor 420 of the information analysis apparatus 4 may calculate an average value of the first propulsion force, an average value of the second propulsion force, and an average value of the third propulsion force in each section obtained by dividing a running route with an equal time, and the communication unit 460 may transmit the average values in each section to the server 5 as a kind of running data. The communication unit 460 of the information analysis apparatus 4 may receive the running data from the server 5, and the display 470 of the information analysis apparatus 4 may display the average values in each section included in the received running data.

3-5. Other Information Presentation

In the system of the present embodiment, not only the first propulsion force, the second propulsion force, the third propulsion force, the first index, the second index, and the third index, but also the motion analysis information 350 (the input information 351, the basic information 352, the first analysis information 353, the second analysis information 354, and the left-right difference ratio 355) or at least one piece of information included in running data may be presented to a user. The presentation to a user may be performed via the notification apparatus 3, and may be performed via the information analysis apparatus 4. Regarding a presentation aspect, the presentation may be performed by using sound output, and may be performed by using image output.

3-6. Sensor

In the embodiment, the acceleration sensor 12 and the angular velocity sensor 14 are integrally formed as the inertial measurement unit 10 and are built into the motion analysis apparatus 2, but the acceleration sensor 12 and the angular velocity sensor 14 may not be integrally formed. Alternatively, the acceleration sensor 12 and the angular velocity sensor 14 may not be built into the motion analysis apparatus 2, and may be directly mounted on the user. In either case, for example, a sensor coordinate system of one sensor may be set to the b frame of the embodiments, the other sensor coordinate system may be converted into the b frame, and the embodiments may be applied thereto.

In the embodiment, a part of which the sensor (the motion analysis apparatus 2 (the IMU 10)) is mounted on the user has been described to be the waist, but the sensor may be mounted on parts other than the waist. A preferable mounting part is the user's trunk (parts other than the limbs). However, a mounting part is not limited to the trunk, and may be mounted on, for example, the user's head or leg other than the arms. The number of sensors is not limited to one, and additional sensors may be mounted on other parts of the body. For example, the sensors may be mounted on the waist and the leg, or the waist and the arm.

3-7. Inertial Navigation Calculation

In the embodiment, the integral processing portion 220 calculates a velocity, a position, an attitude angle, and a distance of the e frame, and the coordinate conversion portion 250 coordinate-converts the parameters into a velocity, a position, an attitude angle, and a distance of the m frame, but the integral processing portion 220 may calculate a velocity, a position, an attitude angle, and a distance of the m frame. In this case, the motion analysis unit 24 preferably performs a motion analysis process by using the velocity, the position, the attitude angle, and the distance of the m frame calculated by the integral processing portion 220, and thus coordinate conversion of a velocity, a position, an attitude angle, and a distance in the coordinate conversion portion 250 is not necessary. The error estimation portion 230 may estimate an error by using the extended Karman filter on the basis of the velocity, the position, and the attitude angle of the m frame.

3-8. Satellite System

In the embodiment, the inertial navigation calculation unit 22 performs a part of the inertial navigation calculation by using a signal from a GPS satellite, but may use a signal from a positioning satellite of a global navigation satellite system (GNSS) other than the GPS, or a positioning satellite other than the GNSS. For example, one, or two or more satellite positioning systems such as a wide area augmentation system (WAAS), a quasi zenith satellite system (QZSS), a global navigation satellite system (GLONASS), GALILEO, a Beidou navigation satellite system (BeiDou) may be used. An indoor messaging system (IMES) may also be used.

3-9. Other Detection Methods

In the embodiment, the running detection section 242 detects a running cycle at a timing at which a vertical acceleration (z axis acceleration) of the user becomes the maximum value which is equal to or greater than a threshold value, but the detection of a running cycle is not limited thereto, and, for example, a running cycle may be detected at a timing at which the vertical acceleration (z axis acceleration) changes from a positive value to a negative value (or a timing changes from a negative value to a positive value). Alternatively, the running detection section 242 may integrate the vertical acceleration (z axis acceleration) so as to calculate a vertical velocity (z axis velocity), and may detect a running cycle by using the calculated vertical velocity (z axis velocity). In this case, the running detection section 242 may detect a running cycle at a timing at which, for example, the velocity crosses a threshold value around a median value between the maximum value and the minimum value by increasing or decreasing a value. For example, the running detection section 242 may calculate a combined acceleration of the x axis, y axis and z axis accelerations and may detect a running cycle by using the calculated combined acceleration. In this case, the running detection section 242 may detect a running cycle at a timing at which, for example, the combined acceleration crosses a threshold value around a median value between the maximum value and the minimum value by increasing or decreasing a value.

3-10. Error Estimation

In the embodiment, the error estimation portion 230 uses a velocity, an attitude angle, an acceleration, an angular velocity, and a position as indexes or state variables indicating a user's state, and estimates errors of the indexes or the state variables by using the extended Karman filter, but may estimate the errors thereof by using some of the velocity, the attitude angle, the acceleration, the angular velocity, and the position as indexes or state variables indicating a user's state. Alternatively, the error estimation portion 230 may estimate the errors thereof by using parameters (for example, a movement distance) other than the velocity, the attitude angle, the acceleration, the angular velocity, and the position as indexes or state variables indicating a user's state.

In the embodiment, the extended Karman filter is used to estimate an error in the error estimation portion 230, but other estimation filters such as a particle filter or H∞ (H infinity) may be used.

3-11. Use of Biological Information

For example, the motion analysis apparatus 2 may generate the motion analysis information 350 (motion index) by using biological information of a user. The biological information may include, for example, a skin temperature, a central part temperature, oxygen consumption, variation between heart beats, a heart rate, a pulse rate, a respiratory rate, heat flow, galvanic skin response, electromyography (EMG), electroencephalogram (EEG), electro-oculogram (EOG), blood pressure, and activity. The motion analysis apparatus 2 may be provided with a device which measures biological information, or the motion analysis apparatus 2 may receive biological information which is measured by a measurement device. For example, the user may wear a wrist watch type pulsimeter, or may wind a heart rate sensor on the chest with a belt so as to perform running, and the motion analysis apparatus 2 may calculate a heart rate during the user's running as the first item of the motion analysis information by using a value measured by the pulsimeter or the heart rate sensor.

3-12. Sensor Attachment Location

In the embodiment, the motion analysis apparatus 2 is mounted on the user but is not limited thereto. For example, an inertial measurement unit (inertial sensor) or the GPS unit 50 may be mounted on the user's body or the like, the inertial measurement unit (inertial sensor) or the GPS unit may transmit a detection result to a portable information apparatus such as a smart phone, an installation type information apparatus such as a personal computer, or the server 5 via a network, and such an apparatus may analyze a motion of the user by using the received detection result. Alternatively, an inertial measurement unit (inertial sensor) or the GPS unit 50 which is mounted on the user's body or the like may record a detection result on a recording medium such as a memory card, and an information apparatus such as a smart phone or a personal computer may read the detection result from the recording medium and may perform a motion analysis process.

3-13. Function Sharing

In the embodiment, some or all of the functions of the motion analysis apparatus 2 may be installed in at least one of the notification apparatus 3 and the information analysis apparatus 4.

In the embodiment, some of the functions of the motion analysis apparatus 2 may be installed in the server 5.

In the embodiment, some or all of the functions of the notification apparatus 3 may be installed in at least one of the motion analysis apparatus 2, the information analysis apparatus 4, and the server 5.

In the embodiment, some or all of the functions of the information analysis apparatus 4 may be installed in at least one of the motion analysis apparatus 2, the notification apparatus 3, and the server 5.

In the embodiment, some or all of the functions of the server 5 may be installed in at least one of the motion analysis apparatus 2, the notification apparatus 3, and the information analysis apparatus 4.

In the embodiment, the motion analysis apparatus 2 performs a process of generating the motion analysis information (motion index), but the motion analysis apparatus 2 may transmit data measured by the inertial measurement unit 10 or a result (calculation data) of the inertial navigation calculation to the server 5, and the server 5 may perform a process of generating the motion analysis information 350 (motion index) (may function as the motion analysis apparatus) by using the measured data or the calculation data and may store the motion analysis information in the database.

For example, in the embodiment, the information analysis apparatus 4 performs an evaluation process, but the server 5 may perform an evaluation process (functions as the information analysis apparatus), and the server 5 may transmit an evaluation result to a display device via a network.

In the embodiment, the running data (motion analysis information) of the user is stored in the database of the server 5, but may be stored in a database built into the storage unit 430 of the information analysis apparatus 4. In other words, the server 5 may be omitted.

3-14. Other Sports

In the embodiment, motion in human running is an analysis target, but the invention is not limited thereto, and motion in walking may be an analysis target. The invention is also applicable to motion analysis in walking or running of a moving object such as an animal or a walking robot. The invention is not limited to running, and is applicable to various motions such as climbing, trail running, skiing (including cross-country and ski jumping), snowboarding, swimming, bicycling, skating, golf, tennis, baseball, and rehabilitation.

3-15. Aspects of Notification Process

In the embodiment, the notification apparatus 3 is a wristwatch type apparatus, but is not limited thereto, and may be a portable apparatus (head mounted display (HMD)) other than the wristwatch type mounted on the user, an apparatus (which may be the motion analysis apparatus 2) mounted on the user's waist, or a portable apparatus (a smart phone or the like) which is not a mounting type apparatus. In a case where the notification apparatus 3 is a head mounted display (HMD), the display 170 thereof provides sufficiently better visibility than the display of the wrist watch type notification apparatus 3, and thus running is unlikely to be disturbed even if the user views the display. Therefore, for example, the display may display the present location of the user or information regarding changes in target hitherto, and may display videos in which a virtual runner created on the basis of time (time set by the user, a record of the user, a record of a celebrity, a world record, or the like) performs running.

3-16. Others

The above-described embodiment and modification examples are only examples, and the invention is not limited thereto. For example, the embodiment and the modification examples may be combined with each other as appropriate.

The invention includes the substantially same configuration (for example, a configuration having the same function, method, and result, or a configuration having the same object and effect) as the configuration described in the embodiment. The invention includes a configuration in which a non-essential part of the configuration described in the embodiment is replaced. The invention includes a configuration which achieves the same operation and effect or a configuration which can achieve the same object as the configuration described in the embodiment. The invention includes a configuration in which a well-known technique is added to the configuration described in the embodiment.

The entire disclosure of Japanese Patent Application No. 2017-022017 filed Feb. 9, 2017 is expressly incorporated by reference herein.

What is claimed is:

1. A motion analysis apparatus for use with a user, the motion analysis apparatus comprising:
    an inertial sensor configured to capture a detection result correlating to a motion of the user when walking or running, the detection result containing information regarding several actions occurring during one cycle of walking or running;
    a processor, housed separately from the inertial sensor, configured to analyze motion information in walking or running of the user by using the detection result from the inertial sensor to separately calculate a propulsion force for each action including: (i) a braking action, (ii) an action involving returning the leg, (iii) an action of stretching the leg or ankle, which occurs during the one cycle of walking or running; and
    a display configured to: (a) display information regarding the calculated propulsion force for each action occurring during the one cycle of walking or running, and (b) provide advice based on the calculated propulsion force for each action occurring during the one cycle of walking or running.

2. The motion analysis apparatus according to claim 1, wherein the one cycle is a section from a first landing to a second landing in a motion related to the walking or the running.

3. The motion analysis apparatus according to claim 1, wherein an action of the user includes at least one of (i) an action using at least one of an inertial force and gravity, (ii) an action using rotation of at least a part of a body of the user, and (iii) an action using muscle strength of the body of the user.

4. The motion analysis apparatus according to claim 1, wherein the display displays information regarding the propulsion force caused by a right foot of the user, and information regarding a propulsion force caused by a left foot of the user.

5. The motion analysis apparatus according to claim 1, wherein the display displays information regarding the braking action within the one cycle along with the information regarding the propulsion force.

6. The motion analysis apparatus according to claim 1, wherein the display displays information regarding the propulsion force at each predetermined distance within a movement path of the user.

7. The motion analysis apparatus according to claim 1, wherein the display displays information regarding the propulsion force for each predetermined time within a movement period of the user.

8. A motion analysis system comprising:
    the motion analysis apparatus according to claim 1; and
    the inertial sensor.

9. A motion analysis system comprising:
    the motion analysis apparatus according to claim 2; and
    the inertial sensor.

10. A motion analysis system comprising:
    the motion analysis apparatus according to claim 3; and
    the inertial sensor.

11. A motion analysis system comprising:
    the motion analysis apparatus according to claim 4; and
    the inertial sensor.

12. A motion analysis system comprising:
    the motion analysis apparatus according to claim 5; and
    the inertial sensor.

13. A motion analysis system comprising:
    the motion analysis apparatus according to claim 6; and
    the inertial sensor.

14. A motion analysis system comprising:
    the motion analysis apparatus according to claim 7; and
    the inertial sensor.

15. A motion analysis method for use with a user, the motion analysis method comprising:
    capturing, by an inertial sensor, a detection result correlating to a motion of the user when walking or running, the detection result containing information regarding several actions occurring during one cycle of walking or running;
    analyzing, by a processor that is housed separately from the inertial sensor, motion information in walking or running of the user by using the detection result from the inertial sensor to separately calculate a propulsion force for each action including: (i) a braking action, (ii) an action involving returning the leg, (iii) an action of stretching the leg or ankle, which occurs during the one cycle of walking or running;
    displaying, by a display, information regarding the calculated propulsion force for each action occurring during the one cycle of walking or running; and
    providing, by the display, advice based on the calculated propulsion force for each action occurring during the one cycle of walking or running.

16. A non-transitory computer readable medium storing a program for use with a user and a motion analysis system having an inertial sensor and a processor, the program causing the inertial sensor and the processor to perform steps comprising:
    capturing, by the inertial sensor, a detection result correlating to a motion of the user when walking or running, the detection result containing information regarding several actions occurring during one cycle of walking or running;
    analyzing, by the processor that is housed separately from the inertial sensor, motion information in walking or running of the user by using the detection result from the inertial sensor to separately calculate a propulsion force for each action including: (i) a braking action, (ii) an action involving returning the leg, (iii) an action of stretching the leg or ankle, which occurs during the one cycle of walking or running;

displaying, by a display, information regarding the propulsion force for each action occurring during the one cycle of walking or running; and providing, by the display, advice based on the calculated propulsion force for each action occurring during the one cycle of walking or running.

\* \* \* \* \*